United States Patent
Choi et al.

(10) Patent No.: US 9,340,521 B2
(45) Date of Patent: *May 17, 2016

(54) METHOD FOR DUAL INHIBITION OF SGLT1 AND SGLT2 USING DIPHENYLMETHANE DERIVATIVES

(71) Applicant: GREEN CROSS CORPORATION, Yongin-si, Gyeonggi-do (KR)

(72) Inventors: Soongyu Choi, Yongin-si (KR); Jae Eun Kim, Yongin-si (KR); Kwang-Seop Song, Yongin-si (KR); Suk Ho Lee, Yongin-si (KR); Kisoo Park, Yongin-si (KR); Hee Jeong Seo, Yongin-si (KR); Min Ju Kim, Yongin-si (KR); Eun-Jung Park, Yongin-si (KR); So Ok Park, Yongin-si (KR); Younggyu Kong, Yongin-si (KR); Hyunku Kang, Yongin-si (KR); Ickhwan Son, Yongin-si (KR); Myung Eun Jung, Yongin-si (KR); Man-Young Cha, Yongin-si (KR); Hyun Jung Kim, Yongin-si (KR); Jun Sung Lee, Yongin-si (KR); Mi-Soon Kim, Yongin-si (KR); Min Woo Lee, Yongin-si (KR); Kinam Lee, Yongin-si (KR)

(73) Assignee: GREEN CROSS CORPORATION, Yongin-si (KR)

( * ) Notice: Subject to any disclaimer, the term of this patent is extended or adjusted under 35 U.S.C. 154(b) by 266 days.

This patent is subject to a terminal disclaimer.

(21) Appl. No.: 13/845,466

(22) Filed: Mar. 18, 2013

(65) Prior Publication Data

US 2014/0274918 A1    Sep. 18, 2014

(51) Int. Cl.
| C07D 309/10 | (2006.01) |
| C07D 407/04 | (2006.01) |
| C07D 409/04 | (2006.01) |
| C07D 409/14 | (2006.01) |

(52) U.S. Cl.
CPC .......... C07D 309/10 (2013.01); C07D 407/04 (2013.01); C07D 409/04 (2013.01); C07D 409/14 (2013.01)

(58) Field of Classification Search
CPC .. C07D 309/10; C07D 407/04; C07D 409/04; C07D 409/14
See application file for complete search history.

(56) References Cited

U.S. PATENT DOCUMENTS

2011/0028414 A1* 2/2011 Tsaklakidis et al. ............ 514/25

FOREIGN PATENT DOCUMENTS

| WO | WO 2012041898 A1 * | 5/2012 | ............. A61K 31/70 |
| WO | WO 2012165914 A2 * | 12/2012 | ............. A61K 31/357 |

* cited by examiner

*Primary Examiner* — Jonathan S Lau
(74) *Attorney, Agent, or Firm* — Sughrue Mion, PLLC

(57) ABSTRACT

The present invention relates to a method for dual inhibition of sodium-dependent glucose cotransporter 1 (SGLT1) and sodium-dependent glucose cotransporter 2 (SGLT2) present in the intestine and kidney by using the compound of formula I or a pharmaceutically acceptable salt or a prodrug thereof:

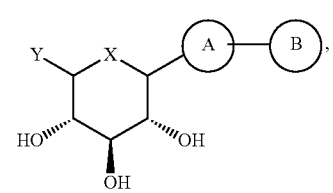

wherein ring A, ring B, X and Y have the same meanings as defined in the specification.

5 Claims, No Drawings

METHOD FOR DUAL INHIBITION OF SGLT1 AND SGLT2 USING DIPHENYLMETHANE DERIVATIVES

FIELD OF THE INVENTION

The present invention relates to a method for dual inhibition of sodium-dependent glucose cotransporter 1 (SGLT1) and sodium-dependent glucose cotransporter 2 (SGLT2) present in the intestine and kidney by using compounds with a diphenylmethane moiety.

BACKGROUND OF THE INVENTION

The prevalence of diabetes has become an increasing concern to the world's population. An estimated 285 million people, corresponding to 6.4% of the world's adult population, will live with diabetes in 2010. The number is expected to grow to 438 million by 2030, corresponding to 7.8% of the adult population. Diabetes is characterized by a chronic metabolic disorder that is caused by failure of the body to produce insulin and/or an inability of the body to respond adequately to circulating insulin. Secreted by the pancreas, insulin increases the ability of tissue to absorb blood glucose. Accordingly, disruption of insulin function results in the high level of blood glucose that is commonly associated with diabetic patients. There are two generally recognized form of diabetes: Type 1 diabetes, or insulin-dependent diabetes mellitus (IDDM), is characterized as an autoimmune disease involving pancreatic β-cells, while type 2 diabetes, or noninsulin-dependent diabetes mellitus (NIDDM), is characterized by β-cell dysfunction and insulin resistance. Type 2 diabetes is the most prevalent abnormality of glucose homeostasis, accounting for approximately 90-95% of all cases of diabetes. The diabetes has been widespread throughout the whole world due to ageing populations and rapid cultural changes such as increasing urbanization, dietary change, decreased physical activity and other unhealthy behavioral patterns.

The burden of diabetes is driven by vascular complications such as cardiovascular disease, stroke, nephropathy, retinopathy, renal failure, and lower limb infection and gangrene. Although these complications result from multiple metanolic disorders, hyperglycemia is considered as the main cause of both the vascular consequences of the disease and the progressive nature of diabetes itself. Most harmful of all is that high glucose levels aggravate insulin resistance, impair β-cell function and finally contribute to β-cell apoptosis. The loss of β-cell function deteriorates hyperglycemia, resulting in a vicious cycle that culminates in the abject destruction of the β-cells. The United Kingdom Prevention of Diabetes Study (UKPDS) showed that incremental reductions in glycosylated hemoglobin (HbA1C) lowered the risk of diabetes-related events [Stratton, I. M. et al. Br. Med. J. 2000, 321, 405-412]. Thus, it is recommended that patients with type 2 diabetes should reduce HbA1C values to 7% and less.

The most important strategy for treatment of type 2 diabetes involves lifestyle interventions that promote body weight loss, leading to an improvement in glycemic control. In case lifestyle interventions are not enough for the management of diabetes, an extensive range of antidiabetic drugs might be considered for the treatment of the condition (monotherapies and combination therapies). These therapies target the liver to reduce glucose output, small intestine to decrease glucose absorption, adipose deposits or muscle to elevate glucose cellular uptake or to promote glucose metabolism, serum proteases to prolong incretin action, and the pancreas to enhance insulin release. Despite the wide range of antihyperglycemic agent, it is difficult for many patients to achieve HbA1C target level. In a study reviewing diabetic patients for control of vascular risk factors, only 37.0% of participants achieved the target goal of HbA1C level of less than 7.0% [Saydah, S. H. et al. J. Am. Med. Assoc. 2004, 291, 335-342]. In addition, current therapies have limited durability and/or are associated with significant side effects such as gastrointestinal intolerance, hypoglycemia, weight gain, lactic acidosis and edema. Thus, significant unmet medical needs still remain for the treatment of diabetes. In particular, safer, better tolerated medications which provide increased efficacy and long-term durability are desired.

The obvious need for new approaches to treat patients with uncontrolled type 2 diabetes has promoted continuous exploration of alternative targets in organs involved in maintenance of glucose homeostasis. In the context of type 2 diabetes, renal glucose reabsorption contributes to plasma glucose levels and the concomitant microvascular complications. Evaluation of molecular targets available in the kidney (a major unexploited contributor to glucose homeostasis) stimulated interest in the development of a new class of antihyperglycemic agents that promote urinary glucose excretion. Inhibitors of the SGLT2 prevent renal glucose reabsorption from the glomerular filtrate and provide an insulin-independent way of controlling hyperglycemia.

Sodium-dependent glucose cotransporters (SGLTs) couple the transport of glucose against a concentration gradient with the simultaneous transport of $Na^+$ down a concentration gradient. Two important SGLT isoforms have been cloned and identified as SGLT1 and SGLT2. SGLT1 is located in the gut, kidney, and heart where its expression regulates cardiac glucose transport. SGLT1 is a high-affinity, low-capacity transporter and therefore accounts for only a small fraction of renal glucose reabsorption. In contrast, SGLT2 is a low-affinity, high-capacity transporter located exclusively at the apical domain of the epithelial cells in the early proximal convoluted tubule. In healthy individuals, greater than 99% of the plasma glucose that filtered in the kidney glomerulus is reabsorbed, resulting in less than 1% of the total filtered glucose being excreted in urine. It is estimated that 90% of renal glucose reabsorption is facilitated by SGLT2; the remaining 10% is likely mediated by SGLT1 in the late proximal straight tubule. Genetic mutations in SGLT2 lead to increased renal glucose excretion of as much as 140 g/day depending on the mutation with no apparent adverse effects on carbohydrate metabolism. Since SGLT2 appears to be responsible for the majority of renal glucose reabsorption based on human mutation studies, it has become a target of therapeutic interest [Lee, J. et al. Bioorg. Med. Chem. 2010, 18, 2178-2194; van den Heuvel, L. P. et al. Hum. Genet. 2020, 111, 544-547].

Phlorizin was isolated from the root bark of the apple tree and evaluated as the first SGLT inhibitor. Despite antidiabetic potency of phlorizin, its metabolic instability due to β-glucosidase cleavage in the intestinal tract has prevented its development as a drug for the treatment of diabetes. Subsequently, T-1095, by Tanabe Seiyaku, was reported as the first orally absorbable SGLT2 inhibitor, overcoming the disadvantage of phlorizin. T-1095 was absorbed in the intestine and converted to an active form, T-1095A. Following the discovery of T-1095, O-aryl glucosides such as sergliflozin and remogliflozin advanced furthest in clinical trials. Again, concern regarding gut β-glucosidase-mediated degradation, resulted in developing sergliflozin A and remogliflozin A being administered as the ethyl carbonate prodrugs sergliflozin and remogliflozin, respectively. Subsequent endeavors to identify SGLT2 inhibitors suitable for oral administration without the need for a prodrug led to the discovery of C-aryl glucoside-derived SGLT2 inhibitors. C-aryl glucoside appears to have drug-like properties with enhanced chemical stability of the glucosidic bond. Extensive SAR studies by Bristol-Myers Squibb identified dapagliflozin, a potent, selective SGLT2 inhibitor for the treatment of type 2 diabetes. At present, dapagliflozin is the most advanced SGLT2 inhibitor in clinical trials and is believed to be the first SGLT2 inhibitor to go to market [Meng, W. et al. *J. Med. Chem.* 2008, 51, 1145-1149]. On the other hand, Mitsubishi Tanabe Pharma, in collaboration with Johnson & Johnson, is developing canagliflozin, another novel C-aryl glucoside-derived SGLT2 inhibitor [Tanabe Seiyaku, WO2008013321].

Considering the important impact of diabetes on public health and unmet medical needs of current therapy, it is no surprise that SGLT2 inhibitors are currently interesting topics of studies, which were published in the following review articles [Washburn, W. N. *Expert Opin. Ther. Patents,* 2009, 19, 1485-1499; Washburn, W. N. *J. Med. Chem.* 2009, 52, 1785-1794].

It is known that SGLT1 plays a role in active transportation of glucose or galactose in the small intestine and glucose reabosorption in kidney (*Am. J. Clin. Nutr.* 1994, 59 (3), 690S-698S). These findings suggest that SGLT1 inhibition could provide good effects on hyperglycemia by delaying sugar absorption in small intestine and inhibiting glucose reabsorption in kidney. Accordingly, dual inhibitor of SGLT1 and SGLT2 can be a novel type of therapeutic agent for treatment of diabetes and other metabolic disease.

SUMMARY OF THE INVENTION

It is an object of the present invention to provide a method for dual inhibition of sodium-dependent glucose cotransporter 1 (SGLT1) and sodium-dependent glucose cotransporter 2 (SGLT2) in a mammal, which comprises administering the compound of formula I or a pharmaceutically acceptable salt or a prodrug thereof to the mammal.

DETAILED DESCRIPTION OF THE INVENTION

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —$OR_aR_b$, wherein $R_a$ is alkyl and $R_b$ is aryl as defined above.

As used herein the term "aryloxy" refers to the group —$OR_b$, wherein $R_b$ is aryl as defined above.

As used herein, the term "mercapto" refers to the group —SH.

As used herein, the term "sulfanyl" refers to the group —$SR_c$, wherein $R_c$ is substituted alkyl, substituted carbocycle, aryl, heteroaryl or heterocyclic, as defined above.

As used herein, the term "sulfinyl" refers to the group —S—(O)$R_c$, wherein $R_c$ is substituted alkyl, substituted carbocycle, aryl, heteroaryl or heterocyclic, as defined above.

As used herein, the term "sulfonyl" refers to the group —$S(O)_2R_c$, wherein $R_c$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_c$ wherein $R_c$ is substituted alkyl, substituted carbocycle, aryl, heteroaryl or heterocyclic, as defined above.

As used herein, the term "carboxyamide" refers to the group —$NHC(O)R_c$ wherein $R_c$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted by substituted alkyl, substituted carbocycle, aryl, heteroaryl or heterocyclic, as defined above.

As used herein, the term "ureido" refers to the group —$NHC(O)NHR_d$ wherein $R_d$ is hydrogen, alkyl, carbocycle or aryl as defined above.

As used herein, the term "guanidino" refers to the group —$NHC(=NH)NH_2$.

As used herein, the term "acyl" refers to the group —C(O)$R_e$, wherein $R_e$ is alkyl, carbocycle, or heterocyclic as defined herein.

As used herein, the term "aroyl" refers to the group —C(O)$R_b$, wherein $R_b$ is aryl as defined herein.

As used herein, the term "heteroaroyl" refers to the group —C(O)$R_f$, wherein $R_f$ is heteroaryl as defined herein.

As used herein, the term "acyloxy" refers to the group —OC(O)$R_e$, wherein $R_e$ is alkyl, carbocycle, or heterocyclic as defined herein.

As used herein, the term "aroyloxy" refers to the group —OC(O)$R_b$, wherein $R_b$ is aryl as defined herein.

As used herein, the term "heteroaroyloxy" refers to the group —OC(O)$R_f$, wherein $R_f$ is heteroaryl as defined herein.

It is to be understood that the present invention also includes a pharmaceutically acceptable salt and an addition salt of the inventive compound, such as a hydrochloride, hydrobromide or trifluoroacetate addition salt and a sodium, potassium and magnesium salt.

The compounds used in the method of the present invention may contain one or more asymmetric carbon atoms and may exist in racemic and optically active forms. All of these compounds and diastereomers are incorporated within the scope of the compounds used in the method of the present invention.

The present invention provides a method for dual inhibition of SGLT1 and SGLT2 in a mammal, which comprises administering the compound of formula I or a pharmaceutically acceptable salt or a prodrug thereof to the mammal:

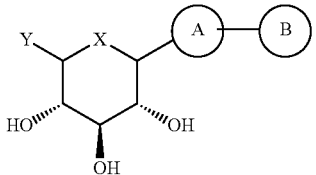

wherein,
X is oxygen or sulfur;
Y is $C_{1-7}$ alkyl, $C_{2-7}$ alkenyl, $C_{2-7}$ alkynyl, $C_{1-7}$ alkoxy, $C_{1-7}$ alkoxy-$C_{1-7}$ alkyl, $C_{1-7}$ alkylsulfinyl, $C_{1-7}$ alkylsulfonyl, or $C_{1-7}$ alkylthio;
ring A is

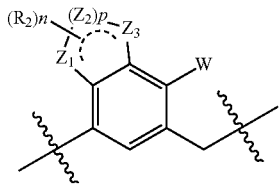

said $R_1$ and W being each independently hydroxy, $C_{1-7}$ alkyl, or $C_{1-7}$ alkoxy,
said n being an integer of 0 to 3,
said $Z_1$, $Z_2$, and $Z_3$ being each independently —$CH_2$—, —CH=, —(CO)—, —O—, —S—, —NH—, or —N=, and
said p being an integer of 1 to 3;
ring B is

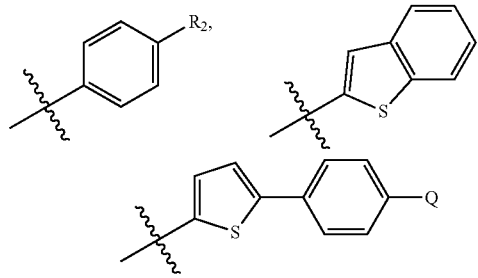

wherein,
said Q is halogen, and
said —$R_2$ being selected from the group consisting of hydrogen, halogen, hydroxy, mercapto, cyano, nitro, amino, carboxy, oxo, $C_{1-7}$ alkyl, $C_{1-7}$ alkylthio, $C_{2-7}$ alkenyl, $C_{2-7}$ alkynyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{3-7}$ cycloalkylthio, $C_{5-10}$ cycloalkenyl, $C_{3-10}$ cycloalkyloxy, $C_{3-10}$ cycloalkyloxy-$C_{1-7}$ alkoxy, phenyl-$C_{1-7}$ alkyl, $C_{1-7}$ alkylthio-phenyl, phenyl-$C_{1-7}$ alkoxy, mono- or di-$C_{1-7}$ alkylamino, mono- or di-$C_{1-7}$ alkylamino-$C_{1-7}$ alkyl, $C_{1-7}$ alkanoyl, $C_{1-7}$ alkanoylamino, $C_{1-7}$ alkylcarbonyl, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfinyl, $C_{6-14}$ arylsulfanyl, $C_{6-14}$ arylsulfonyl, $C_{6-14}$ aryl, 5 to 13-membered heteroaryl, 5 to 10-membered heterocycloalkyl, 5 to 10-membered heterocycloalkyl-$C_{1-7}$ alkyl, or 5 to 10-membered heterocycloalkyl-$C_{1-7}$ alkoxy
said alkyl, alkenyl, alkynyl, or alkoxy is optionally substituted with at least one substituent selected from the group consisting of halogen, hydroxy, cyano, nitro, amino, mercapto, $C_{1-7}$ alkyl, and $C_{2-7}$ alkynyl; and
said cycloalkyl, cycloalkenyl, aryl, heteroaryl, or heterocycloalkyl is optionally substituted with at least one substituent selected from the group consisting of halogen, hydroxy, cyano, nitro, amino, mercapto, $C_{1-4}$ alkyl, and $C_{1-4}$ alkoxy.

In one embodiment of the present invention, ring A may be selected from the group consisting of:

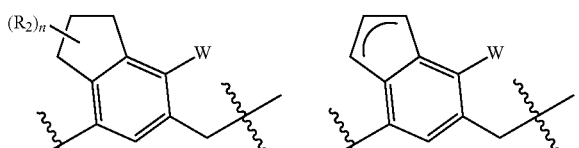

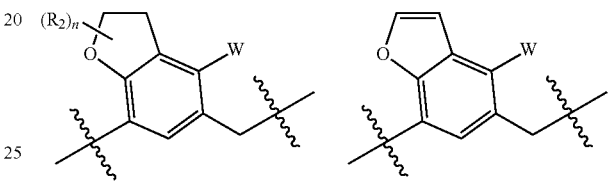

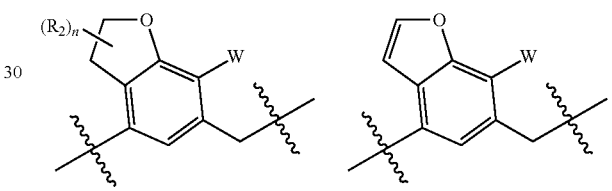

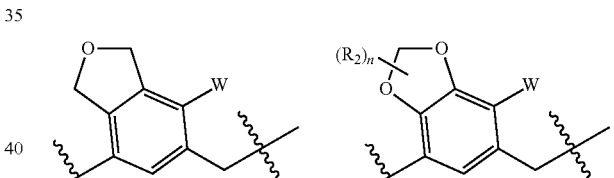

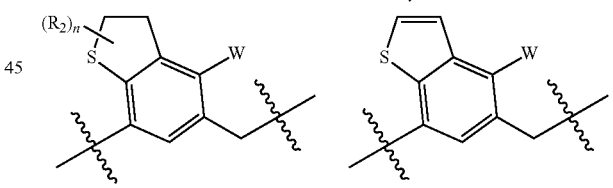

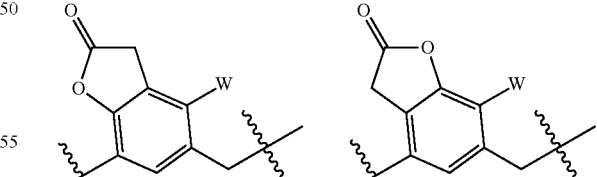

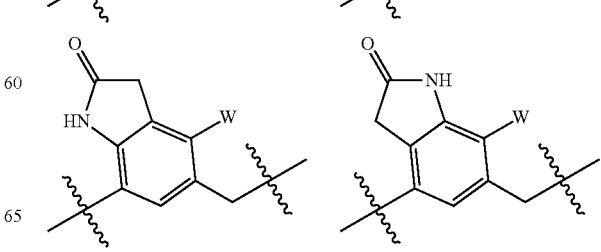

-continued
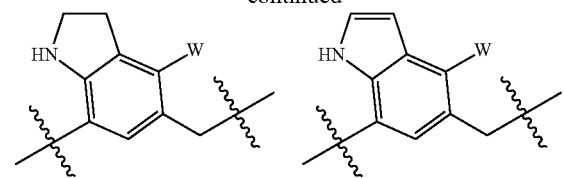
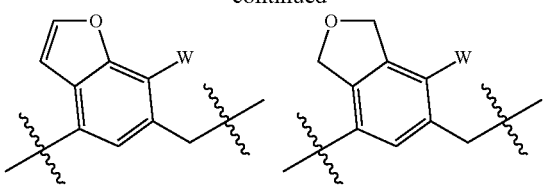
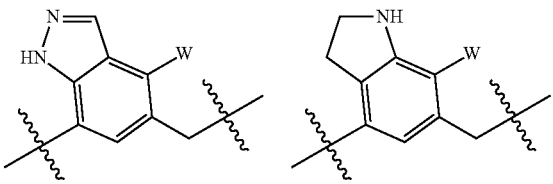
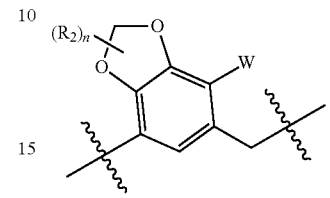
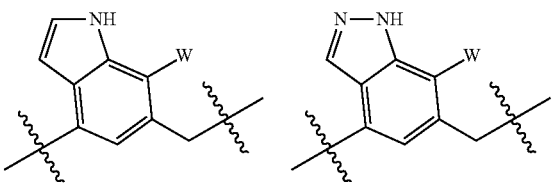
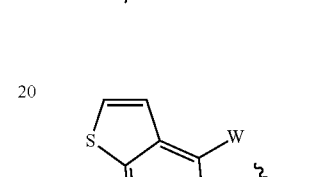
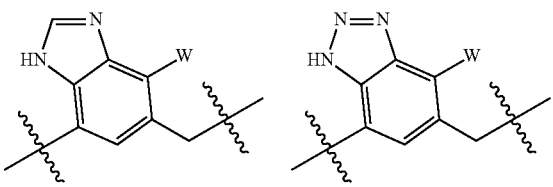
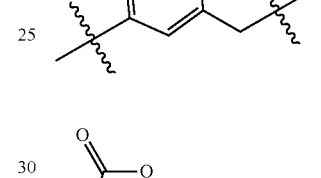
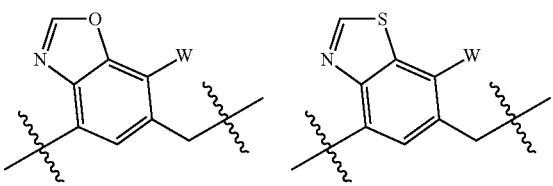
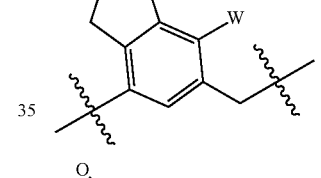
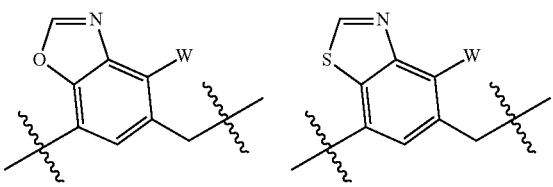
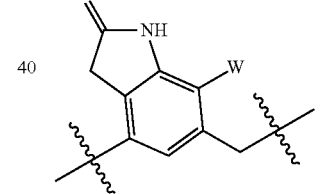
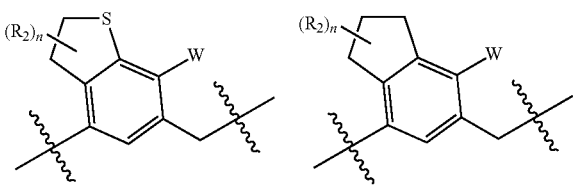
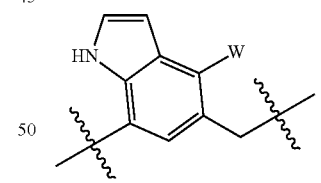
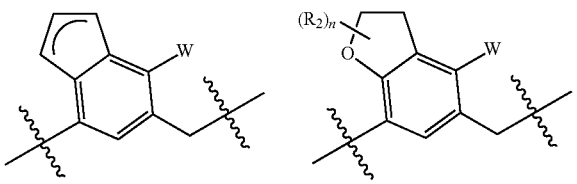
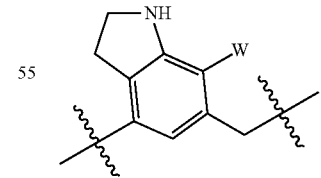
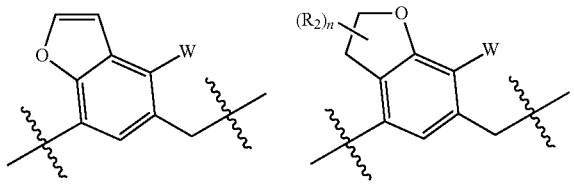
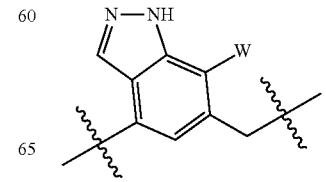

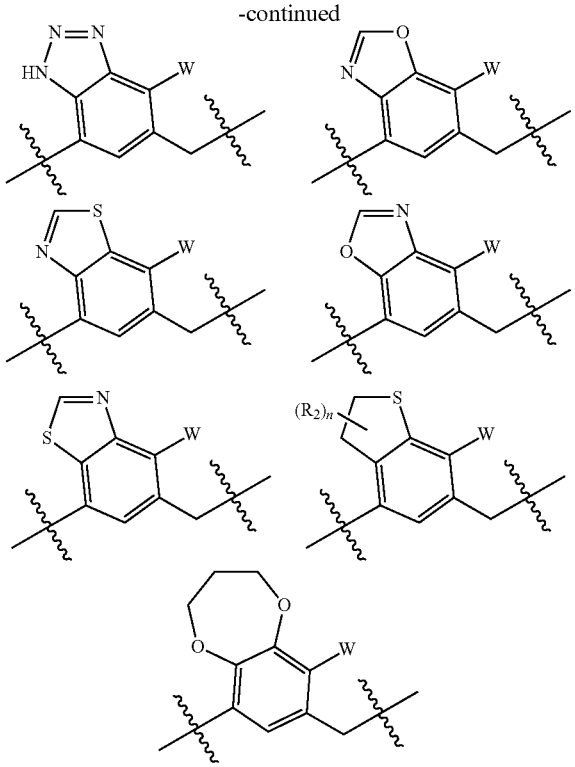

In another embodiment of the present invention, ring B may be selected from the group consisting of:

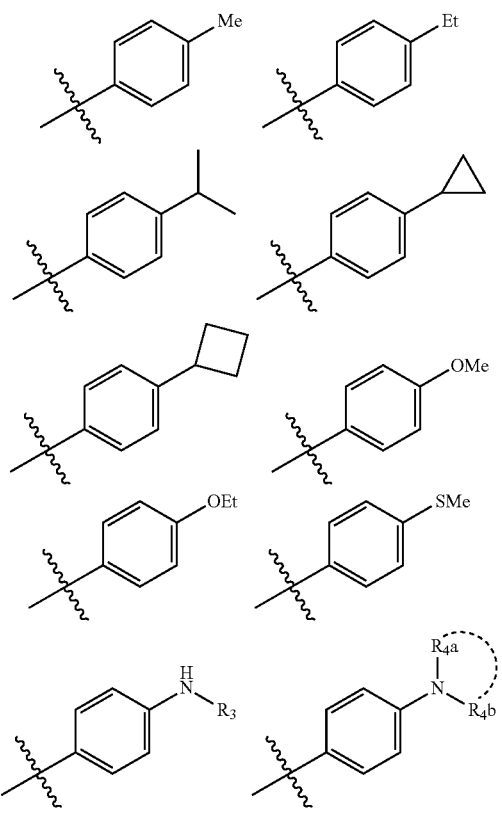

in which $R_3$ is hydrogen, or $C_{1-7}$ alkyl, and $R_{4a}$ and $R_{4b}$ are each independently $C_{1-7}$ alkyl, or $R_{4a}$ and $R_{4b}$ are connected to form a 5 to 10-membered heterocycloalkyl.

In a preferred embodiment of the present invention, ring A is a benzene, indane, indene, dihydrobenzofuran, dihydroisobenzofuran, benzofuran, dihydrobenzothiophene, benzothiophene, tetrahydronaphthalene, dihydronaphthalene, chroman, chromene, isochroman, isochromene, benzodioxole, benzodioxane, benzooxazine, tetrahydroquinoline, tetrahydroquinoxaline, tetrahydroisoquinoline, indazole, indole, indoline, benzoimidazole, benzooxazole, benzothiazole, benzotriazole, quinazoline, quinoxaline, cinnoline, phthalazine, or benzotriazine ring, which is optionally substituted with a substituent as defined herein.

In a preferred embodiment of the present invention, ring B is a benzene ring which is optionally substituted with a substituent as defined herein.

The compounds of formula I may be selected from the group consisting of:

(1) (2S,3R,4R,5S,6R)-2-(7-bromo-6-(4-methoxybenzyl)-2,3-dihydro-1H-inden-4-yl)-6-(hydroxymethyl)tetrahydro-2H-pyran-3,4,5-triol;

(2) (2S,3R,4R,5S,6R)-2-(7-bromo-6-(4-ethoxybenzyl)-2,3-dihydro-1H-inden-4-yl)-6-(hydroxymethyl)tetrahydro-2H-pyran-3,4,5-triol;

(3) (2S,3R,4R,5S,6R)-2-(7-bromo-6-(4-ethylbenzyl)-2,3-dihydro-1H-inden-4-yl)-6-(hydroxymethyl)tetrahydro-2H-pyran-3,4,5-triol;

(4) (2S,3R,4R,5S,6R)-2-(7-chloro-6-(4-methoxybenzyl)-2,3-dihydro-1H-inden-4-yl)-6-(hydroxymethyl)tetrahydro-2H-pyran-3,4,5-triol;

(5) (2R,3S,4R,5R,6S)-2-(hydroxymethyl)-6-(6-(4-methoxybenzyl)-7-methyl-2,3-dihydro-1H-inden-4-yl)tetrahydro-2H-pyran-3,4,5-triol;

(6) (2S,3R,4R,5S,6R)-2-(7-chloro-6-(4-ethoxybenzyl)-2,3-dihydro-1H-inden-4-yl)-6-(hydroxymethyl)tetrahydro-2H-pyran-3,4,5-triol;

(7) (2S,3R,4R,5S,6R)-2-(6-(4-ethoxybenzyl)-7-methyl-2,3-dihydro-1H-inden-4-yl)-6-(hydroxymethyl)tetrahydro-2H-pyran-3,4,5-triol;

(8) (2S,3R,4R,5S,6R)-2-(4-chloro-5-(4-ethylbenzyl)-2,3-dihydrobenzofuran-7-yl)-6-(hydroxymethyl)tetrahydro-2H-pyran-3,4,5-triol;

(9) (2S,3R,4R,5S,6R)-2-(5-chloro-6-(4-ethoxybenzyl)chroman-8-yl)-6-(hydroxymethyl)tetrahydro-2H-pyran-3,4,5-triol;

(10) (2S,3R,4R,5S,6R)-2-(5-chloro-6-(4-methoxybenzyl)chroman-8-yl)-6-(hydroxymethyl)tetrahydro-2H-pyran-3,4,5-triol;

(11) (2S,3R,4R,5S,6R)-2-(5-chloro-6-(4-ethylbenzyl)chroman-8-yl)-6-(hydroxymethyl)tetrahydro-2H-pyran-3,4,5-triol;

(12) (2S,3R,4R,5S,6R)-2-(4-chloro-5-(4-methoxybenzyl)-2,3-dihydrobenzofuran-7-yl)-6-(hydroxymethyl)tetrahydro-2H-pyran-3,4,5-triol;

(13) (2S,3R,4R,5S,6R)-2-(4-chloro-5-(4-ethoxybenzyl)-2,3-dihydrobenzofuran-7-yl)-6-(hydroxymethyl)tetrahydro-2H-pyran-3,4,5-triol;

(14) (2S,3R,4R,5S,6R)-2-(8-chloro-7-(4-ethylbenzyl)chroman-5-yl)-6-(hydroxymethyl)tetrahydro-2H-pyran-3,4,5-triol;

(15) (2S,3R,4R,5S,6R)-2-(8-chloro-7-(4-methoxybenzyl)-2,3-dihydrobenzo[b][1,4]dioxin-5-yl)-6-(hydroxymethyl)tetrahydro-2H-pyran-3,4,5-triol;

(16) (2S,3R,4R,5S,6R)-2-(8-chloro-7-(4-ethylbenzyl)-2,3-dihydrobenzo[b][1,4]dioxin-5-yl)-6-(hydroxymethyl)tetrahydro-2H-pyran-3,4,5-triol;

(17) (2S,3R,4R,5S,6R)-2-(4-chloro-5-(4-cyclopropylbenzyl)-2,3-dihydrobenzofuran-7-yl)-6-(hydroxymethyl)tetrahydro-2H-pyran-3,4,5-triol;

(18) (2S,3R,4R,5S,6R)-2-(5-chloro-6-(4-cyclopropylbenzyl)chroman-8-yl)-6-(hydroxymethyl)tetrahydro-2H-pyran-3,4,5-triol;

(19) (2S,3R,4R,5S,6R)-2-(4-chloro-5-(4-ethylbenzyl)-2-methyl-2,3-dihydrobenzo[b]thiophen-7-yl)-6-(hydroxymethyl)tetrahydro-2H-pyran-3,4,5-triol;

(20) (2S,3R,4R,5S,6R)-2-(4-chloro-5-(4-ethoxybenzyl)-2-methyl-2,3-dihydrobenzofuran-7-yl)-6-(methylthio)tetrahydro-2H-pyran-3,4,5-triol;

(21) (2S,3R,4R,5S,6R)-2-(8-chloro-7-(4-ethoxybenzyl)-2,3-dihydrobenzo[b][1,4]dioxin-5-yl)-6-(methylthio)tetrahydro-2H-pyran-3,4,5-triol;

(22) (2S,3R,4R,5S,6R)-2-(8-chloro-7-(4-cyclopropylbenzyl)chroman-5-yl)-6-(hydroxymethyl)tetrahydro-2H-pyran-3,4,5-triol;

(23) (2S,3R,4R,5S,6R)-2-(8-chloro-7-(4-methoxybenzyl)chroman-5-yl)-6-(hydroxymethyl)tetrahydro-2H-pyran-3,4,5-triol;

(24) (2S,3R,4R,5S,6R)-2-(7-chloro-6-(4-cyclopropylbenzyl)benzo[d][1,3]dioxol-4-yl)-6-(hydroxymethyl)tetrahydro-2H-pyran-3,4,5-triol;

(25) (2S,3R,4R,5S,6R)-2-(7-chloro-6-(4-methoxybenzyl)benzo[d][1,3]dioxol-4-yl)-6-(hydroxymethyl)tetrahydro-2H-pyran-3,4,5-triol;

(26) (2S,3R,4R,5S,6R)-2-(7-chloro-6-(4-ethylbenzyl)benzo[d][1,3]dioxol-4-yl)-6-(hydroxymethyl)tetrahydro-2H-pyran-3,4,5-triol;

(27) (2S,3R,4R,5S,6R)-2-(8-chloro-7-(4-cyclopropylbenzyl)-2,3-dihydrobenzo[b][1,4]dioxin-5-yl)-6-(hydroxymethyl)tetrahydro-2H-pyran-3,4,5-triol;

(28) (2S,3R,4R,5S,6R)-2-(7-chloro-6-(4-vinylbenzyl)-2,3-dihydrobenzofuran-4-yl)-6-(hydroxymethyl)tetrahydro-2H-pyran-3,4,5-triol;

(29) (2S,3R,4R,5S,6R)-2-(5-chloro-6-(4-methoxybenzyl)chroman-8-yl)-6-(methylthio)tetrahydro-2H-pyran-3,4,5-triol;

(30) (2S,3R,4R,5S,6R)-2-(4-chloro-5-(4-methoxybenzyl)-2,3-dihydrobenzo[b]thiophen-7-yl)-6-(hydroxymethyl)tetrahydro-2H-pyran-3,4,5-triol;

(31) (2S,3R,4R,5S,6R)-2-(4-chloro-5-(4-ethoxybenzyl)-3-methyl-2,3-dihydrobenzofuran-7-yl)-6-(hydroxymethyl)tetrahydro-2H-pyran-3,4,5-triol;

(32) (2S,3R,4R,5S,6R)-2-(7-(difluoromethyl)-6-(4-methoxybenzyl)-2,3-dihydro-1H-inden-4-yl)-6-(hydroxymethyl)tetrahydro-2H-pyran-3,4,5-triol;

(33) (2S,3R,4R,5S,6R)-2-(7-bromo-6-(4-ethylbenzyl)-2,3-dihydro-1H-inden-4-yl)-6-(hydroxymethyl)tetrahydro-2H-pyran-3,4,5-triol;

(34) (2S,3R,4R,5S,6R)-2-(7-chloro-6-(4-methoxybenzyl)-2,3-dihydrobenzo[b]thiophen-4-yl)-6-(hydroxymethyl)tetrahydro-2H-pyran-3,4,5-triol;

(35) (2S,3R,4R,5S,6R)-2-(7-chloro-6-(4-ethylbenzyl)-2,3-dihydrobenzo[b]thiophen-4-yl)-6-(hydroxymethyl)tetrahydro-2H-pyran-3,4,5-triol;

(36) (2S,3R,4R,5S,6R)-2-(8-chloro-7-(4-methoxybenzyl)thiochroman-5-yl)-6-(hydroxymethyl)tetrahydro-2H-pyran-3,4,5-triol;

(37) (2R,3S,4R,5R,6S)-2-(hydroxymethyl)-6-(3-(4-methoxybenzyl)-4-methyl-5,6,7,8-tetrahydronaphthalen-1-yl)tetrahydro-2H-pyran-3,4,5-triol;

(38) (2S,3R,4R,5S,6R)-2-(4-chloro-3-(4-methoxybenzyl)-5,6,7,8-tetrahydronaphthalen-1-yl)-6-(hydroxymethyl)tetrahydro-2H-pyran-3,4,5-triol;

(39) (2S,3R,4R,5S,6R)-2-(4-chloro-3-(4-ethoxybenzyl)-5,6,7,8-tetrahydronaphthalen-1-yl)-6-(hydroxymethyl)tetrahydro-2H-pyran-3,4,5-triol;

(40) (2S,3R,4R,5S,6R)-2-(7-chloro-6-(4-methylbenzyl)benzo[d][1,3]dioxol-4-yl)-6-(hydroxymethyl)tetrahydro-2H-pyran-3,4,5-triol;

(41) (2R,3S,4R,5R,6S)-2-(hydroxymethyl)-6-(6-(4-methylbenzyl)-2,3-dihydro-1H-inden-4-yl)tetrahydro-2H-pyran-3,4,5-triol;

(42) (2S,3R,4R,5S,6R)-2-(8-chloro-7-(4-methylbenzyl)-2,3-dihydrobenzo[b][1,4]dioxin-5-yl)-6-(hydroxymethyl)tetrahydro-2H-pyran-3,4,5-triol;

(43) (2S,3R,4R,5S,6R)-2-(4-chloro-3-(4-ethylbenzyl)-5,6,7,8-tetrahydronaphthalen-1-yl)-6-(hydroxymethyl)tetrahydro-2H-pyran-3,4,5-triol;

(44) (2S,3R,4R,5S,6R)-2-(3-(4-ethylbenzyl)-4-methyl-5,6,7,8-tetrahydronaphthalen-1-yl)-6-(hydroxymethyl)tetrahydro-2H-pyran-3,4,5-triol;

(45) (2S,3R,4R,5S,6R)-2-(8-chloro-7-(4-methylbenzyl)chroman-5-yl)-6-(hydroxymethyl)tetrahydro-2H-pyran-3,4,5-triol;

(46) (2S,3R,4R,5S,6R)-2-(4-chloro-5-(4-methylbenzyl)-2,3-dihydrobenzofuran-7-yl)-6-(hydroxymethyl)tetrahydro-2H-pyran-3,4,5-triol;

(47) (2S,3R,4R,5S,6R)-2-(3-(4-ethoxybenzyl)-4-methyl-5,6,7,8-tetrahydronaphthalen-1-yl)-6-(hydroxymethyl)tetrahydro-2H-pyran-3,4,5-triol;

(48) (2S,3R,4R,5S,6R)-2-(7-chloro-6-(4-methoxybenzyl)-2,3-dihydro-1H-inden-4-yl)6-(methylthio)tetrahydro-2H-pyran-3,4,5-triol;

(49) (2S,3R,4R,5S,6R)-2-(7-chloro-6-(4-(methylthio)benzyl)benzo[d][1,3]dioxol-4-yl)-6-(hydroxymethyl)tetrahydro-2H-pyran-3,4,5-triol;

(50) (2S,3R,4R,5S,6R)-2-(8-chloro-7-(4-(methylthio)benzyl)-2,3-dihydrobenzo[b][1,4]dioxin-5-yl)-6-(hydroxymethyl)tetrahydro-2H-pyran-3,4,5-triol;

(51) (2S,3R,4R,5S,6R)-2-(7-chloro-6-(4-ethoxybenzyl)benzo[d][1,3]dioxol-4-yl)-6-(methylthio)tetrahydro-2H-pyran-3,4,5-triol;

(52) (2S,3R,4R,5S,6R)-2-(5-chloro-6-(4-methylbenzyl)chroman-8-yl)-6-(hydroxymethyl)tetrahydro-2H-pyran-3,4,5-triol;

(53) (2S,3R,4R,5S,6R)-2-(6-(benzo[b]thiophen-2-ylmethyl)-7-chlorobenzo[d][1,3]dioxol-4-yl)-6-(hydroxymethyl)tetrahydro-2H-pyran-3,4,5-triol;

(54) (2S,3R,4R,5S,6R)-2-(8-chloro-7-((5-(4-fluorophenyl)thiophen-2-yl)methyl)-2,3-dihydrobenzo[b][1,4]dioxin-5-yl)-6-(hydroxymethyl)tetrahydro-2H-pyran-3,4,5-triol;

(55) (2S,3R,4R,5S,6R)-2-(6-(benzo[b]thiophen-2-ylmethyl)-7-chloro-2,3-dihydrobenzofuran-4-yl)-6-(hydroxymethyl)tetrahydro-2H-pyran-3,4,5-triol;

(56) (2S,3R,4R,5S,6R)-2-(7-(benzo[b]thiophen-2-ylmethyl)-8-chloro-2,3-dihydrobenzo[b][1,4]dioxin-5-yl)-6-(hydroxymethyl)tetrahydro-2H-pyran-3,4,5-triol;

(57) (2S,3R,4R,5S,6R)-2-(4-bromo-3-(4-ethylbenzyl)-5,6,7,8-tetrahydronaphthalen-1-yl)-6-(hydroxymethyl)tetrahydro-2H-pyran-3,4,5-triol;

(58) (2S,3R,4R,5S,6R)-2-(4-bromo-3-(4-ethoxybenzyl)-5,6,7,8-(tetrahydronaphthalen-1-yl)-6-(hydroxymethyl)tetrahydro-2H-pyran-3,4,5-triol;

(59) (2S,3R,4R,5S,6R)-2-(7-chloro-6-(4-ethoxybenzyl)-2,3-dihydrobenzo[b]thiophen-4-yl)-6-(hydroxymethyl)tetrahydro-2H-pyran-3,4,5-triol;

(60) (2S,3R,4R,5S,6R)-2-(7-chloro-6-(4-cyclopropylbenzyl)-2,3-dihydrobenzo[b]thiophen-4-yl)-6-(hydroxymethyl)tetrahydro-2H-pyran-3,4,5-triol;

(61) (2R,3S,4R,5R,6S)-2-((hydroxymethyl)-6-(7-methyl-6-(4-methylbenzyl)benzo[d][1,3]dioxol-4-yl)tetrahydro-2H-pyran-3,4,5-triol;

(62) (2S,3R,4R,5S,6R)-2-(5-chloro-6-(4-cyclobutylbenzyl)chroman-8-yl)-6-(hydroxymethyl)tetrahydro-2H-pyran-3,4,5-triol;

(63) (2R,3S,4R,5R,6S)-2-((hydroxymethyl)-6-(6-(4-methoxybenzyl)-7-methylbenzo[d][1,3]dioxol-4-yl)tetrahydro-2H-pyran-3,4,5-triol;

(64) (2S,3R,4R,5S,6R)-2-(6-(4-ethylbenzyl)-7-methylbenzo[d][1,3]dioxol-4-yl)-6-(hydroxymethyl)tetrahydro-2H-pyran-3,4,5-triol;

(65) (2S,3R,4R,5S,6R)-2-(6-(4-ethoxybenzyl)-7-methylbenzo[d][1,3]dioxol-4-yl)-6-(hydroxymethyl)tetrahydro-2H-pyran-3,4,5-triol.

The compound of formula I is effective as a dual inhibitor against sodium-dependent glucose cotransporter 1 (SGLT1) and sodium-dependent glucose cotransporter 2 (SGLT2), thereby preventing or treating a metabolic disease.

The compound of formula I or a pharmaceutically acceptable salt or a prodrug thereof may be contained in a pharmaceutical composition as an active ingredient for preventing or treating a metabolic disorder. The metabolic disorder may be diabetes, cardiovascular disease, or hypertension, preferably diabetes.

The pharmaceutical composition may be administered orally or parenterally, e.g., intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg, and preferably from 1 mg to 100 mg of the compound of formula I or its pharmaceutically acceptable salt or prodrug.

The suitable daily dosage for oral administration is about 0.01 mg/kg body weight to 40 mg/kg body weight of the compound of formula I or its pharmaceutically acceptable salt or prodrug, and may be administered 1 to 6 times a day, depending on the patient's condition.

The compounds of formula I of the present invention may be prepared by several synthetic procedures. The compounds of the present invention and the preparation thereof will be better understood in connection with the following synthetic schemes, which are merely illustrative of the methods by which the compounds of the invention may be prepared and are not intended to limit the scope of the invention as defined in the appended claims.

General Synthetic Sequence

Some particular compounds of the present invention such as compounds of formula I-a can be prepared by a) reacting a compound of formula II with a compound of formula III to obtain a compound of formula IV; and (b) deprotecting and reducing the compound of formula IV to obtain a compound of formula I-a,

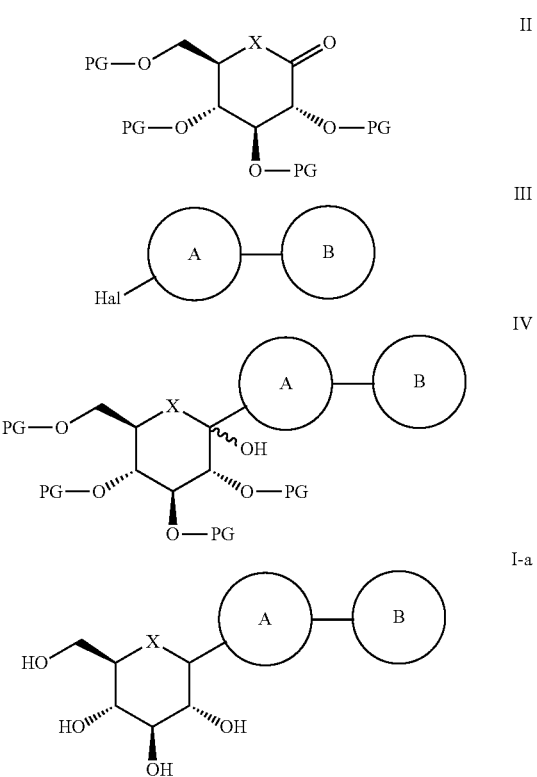

wherein, X, ring A and ring B are same as defined herein, Hal is halogen, and PG is trimethylsilyl or benzyl.

In one embodiment of the present invention, step (b) is carried out by deprotecting the compound of formula IV to obtain a compound of formula V, and reducing the compound of formula V to obtain the compound of formula I-a, when PG is trimethylsilyl:

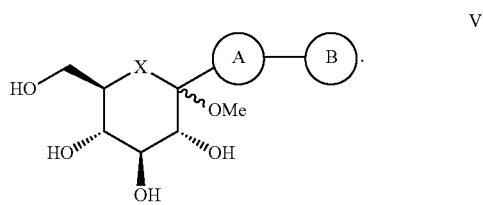

In another embodiment of the present invention, step (b) is carried out by reducing the compound of formula IV to obtain a compound of formula VI, and deprotecting the compound of formula VI to obtain the compound of formula I-a, when PG is benzyl:

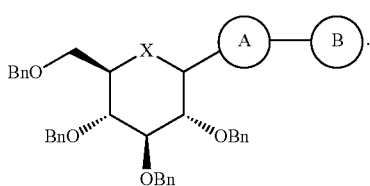

Hereinafter, the particular examples of the procedure are described in detail.

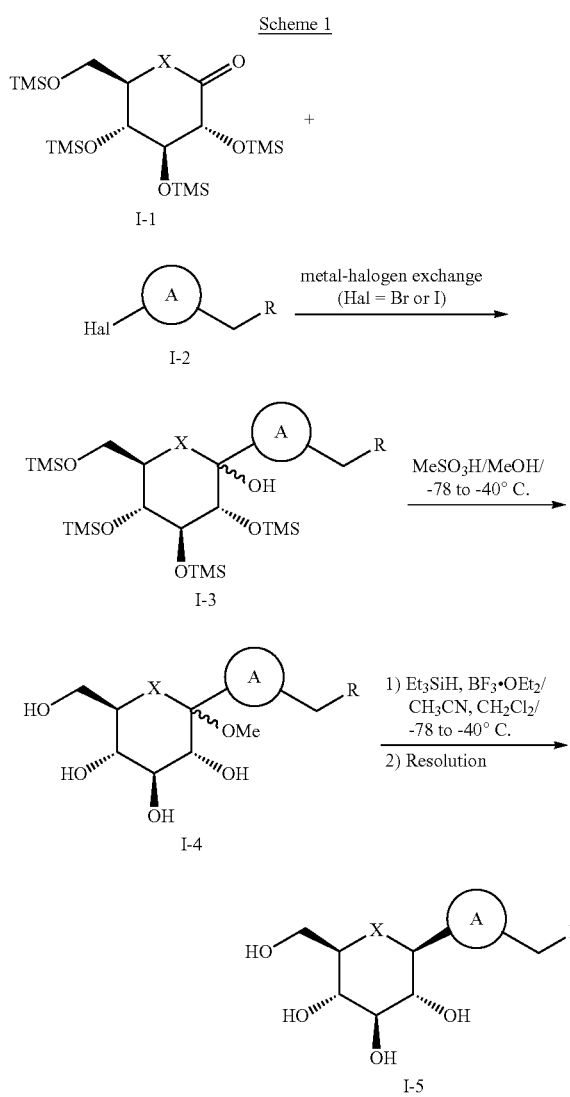

X: O or S
R: Aryl

A general synthetic route to desired compound I-5 is illustrated in Scheme 1. Metal-halogen exchange of halogenated compound 1-2, followed by addition of the nascent organo metallic compound to persilylated gluconolactone or thiogluconolactone (*Tetrahedron Lett.* 1981, 22, 5061-5062; *J. Med. Chem.* 2010, 53, 3247-3261) I-1, produces a mixture of the corresponding lactol I-3, which is converted in situ to the desilylated O-methyl lactol by treatment with methansulfonic acid in methanol at cold conditions (−78~−40° C.). The reduction of the anomeric methoxy group of lactol I-4 using triethylsilane and boron trifluoride diethyl etherate is performed to generate the corresponding mixture of α,β-isomers. The required β-isomers I-5 are resolved by selective crystallization of peracetylated mixtures or prep. HPLC (reverse phase) of final compounds.

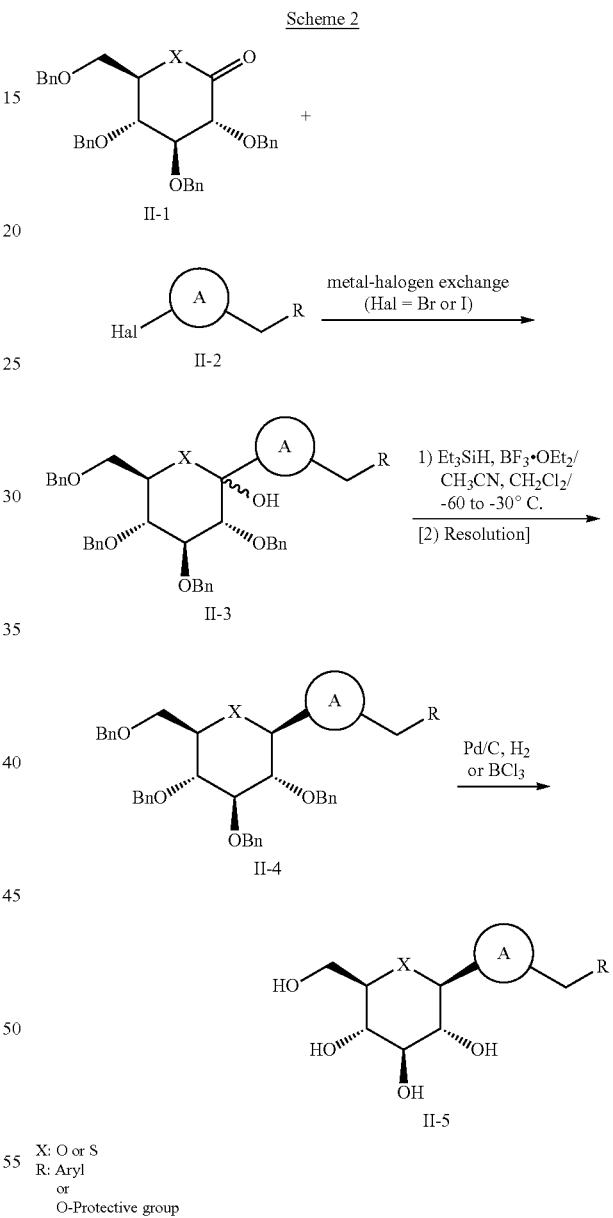

X: O or S
R: Aryl
or
O-Protective group

Perbenzylated gluconolactone or thiogluconolactone (*Tetrahedron Lett.* 1981, 22, 5061-5062; *J. Med. Chem.* 2010, 53, 3247-3261) II-1, instead of persilylated gluconolactone or thiogluconolactone I-1, is also used to prepare the corresponding lactols II-3, which are reduced using triethylsilane and boron trifluoride diethyl etherate. Deprotection of benzyl groups is performed using Pd/C under hydrogen atmosphere or BCl₃ at low temperature (<0° C.).

Scheme 3
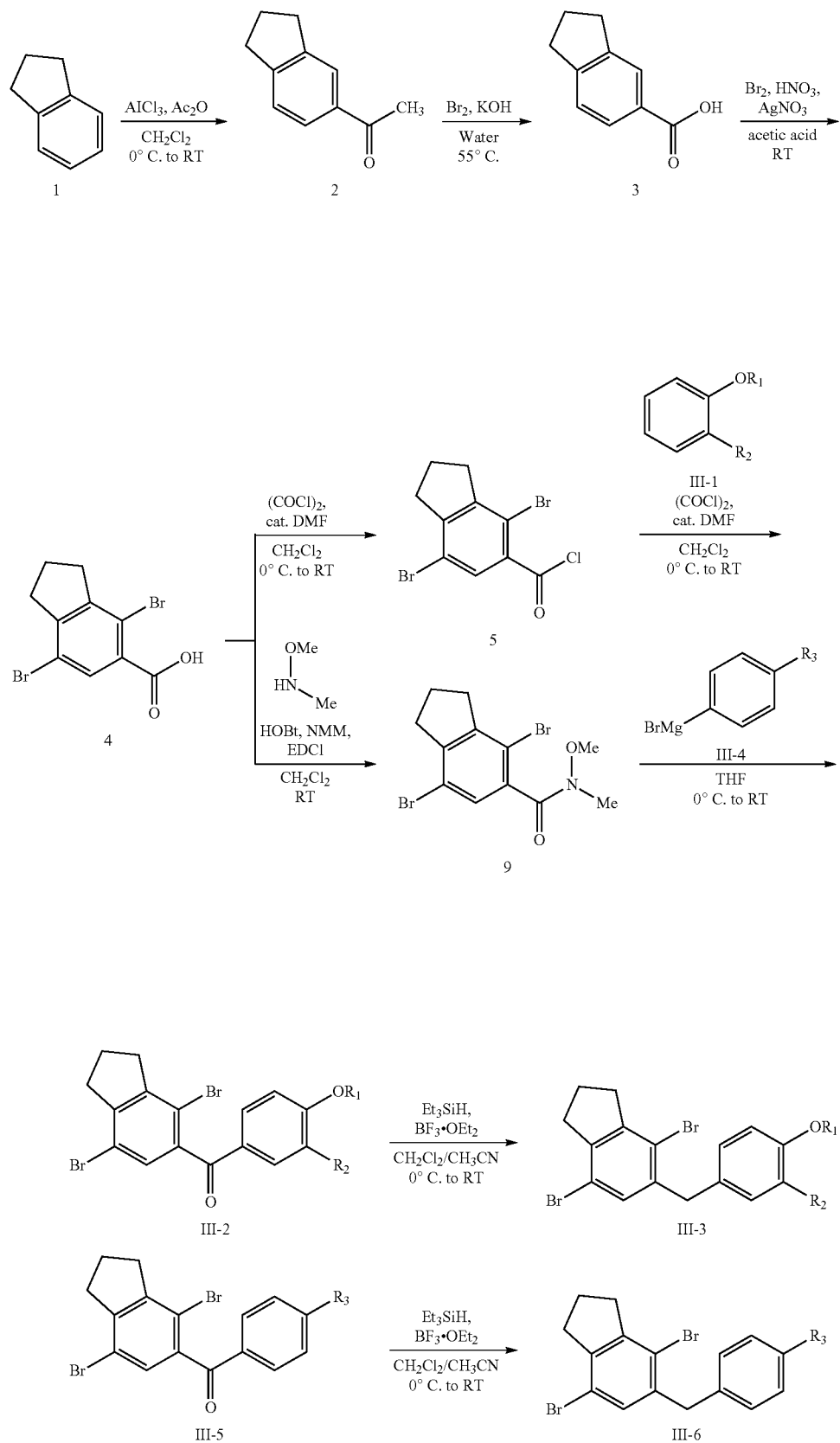

A key intermediate 4 is prepared from compound 1 through three steps. The starting material 1 is converted into the corresponding 5-acetylated intermediate 2 by the Friedel-Crafts reaction with acetyl anhydride in quantitative yield. The methyl ketone compound 2 is brought into haloform reaction to obtain benzoic acid 3 at heating conditions (55° C.). Bromination of the benzoic acid 3 with bromine and AgNO₃ gives the 2,5-dibromide intermediate 4 in acidic conditions.

The dibrominated benzoic acid 4 is converted to the corresponding acyl chloride 5, which is used for the Friedel-Crafts acylation of compound III-1 to provide the desired diarylketone III-2. Reduction of diarylketone III-2 by triethylsilane in the presence of boron trifluoride etherate provides aglycon III-3. Alternatively, another desired aglycons III-6 are also synthesized through Weinreb amide 9, which is prepared from the acid 4 by treatment of N,O-dimethylhydroxylamine hydrochloride, HOBt, EDCI and NMM under mild conditions in good yield. Reaction of Weinreb amide 9 with proper organometallic nucleophiles, such as Grignard reagents III-4, produces the desired ketones III-5. Finally, the diarylketones III-5 are reduced by triethylsilane in the presence of boron trifluoride etherate to yield aglycon III-6.

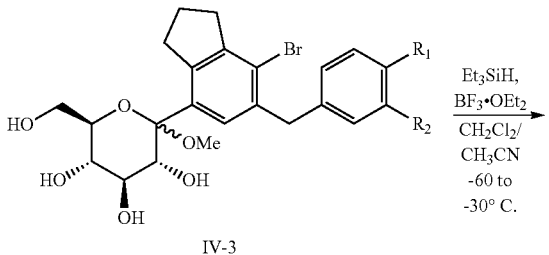

IV-3

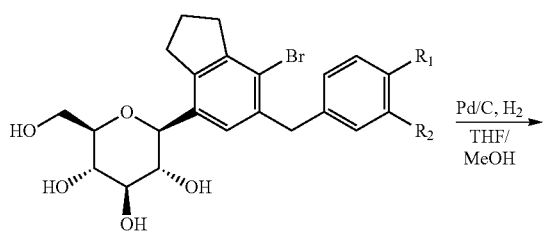

IV-4

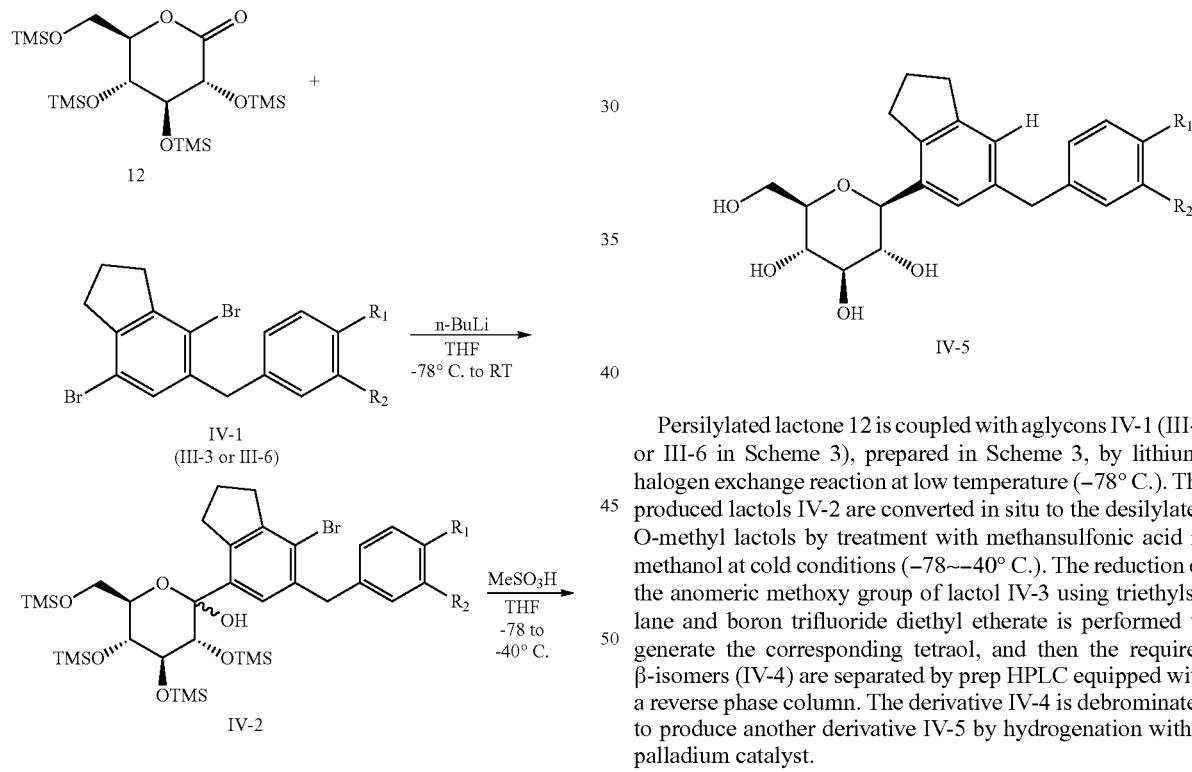

Persilylated lactone 12 is coupled with aglycons IV-1 (III-3 or III-6 in Scheme 3), prepared in Scheme 3, by lithium-halogen exchange reaction at low temperature (−78° C.). The produced lactols IV-2 are converted in situ to the desilylated O-methyl lactols by treatment with methansulfonic acid in methanol at cold conditions (−78~−40° C.). The reduction of the anomeric methoxy group of lactol IV-3 using triethylsilane and boron trifluoride diethyl etherate is performed to generate the corresponding tetraol, and then the required β-isomers (IV-4) are separated by prep HPLC equipped with a reverse phase column. The derivative IV-4 is debrominated to produce another derivative IV-5 by hydrogenation with a palladium catalyst.

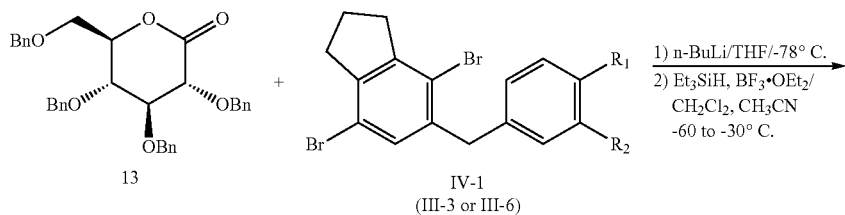

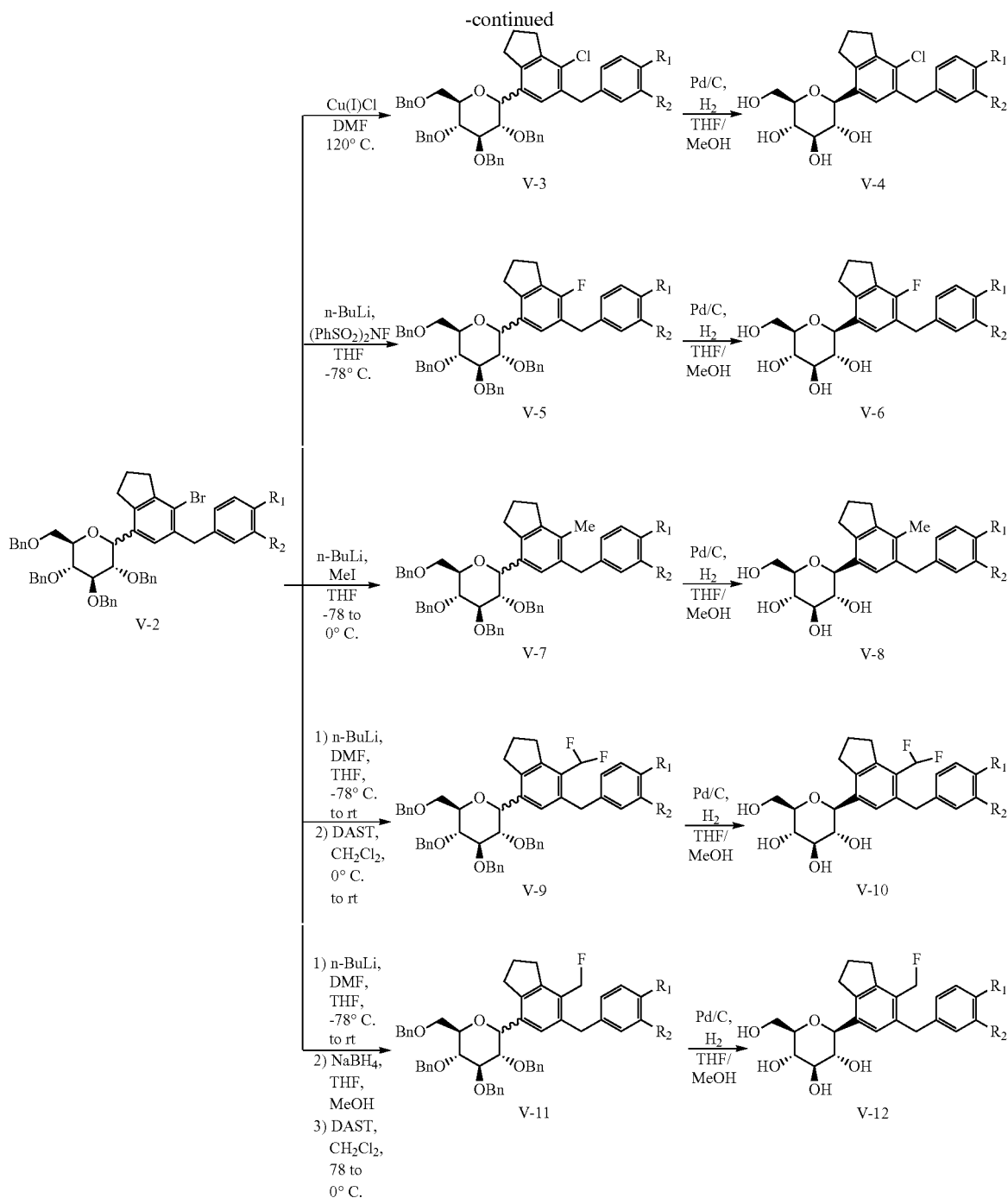

Aglycons V-1 (III-3 or III-6 in Scheme 3), prepared in Scheme 3, are incorporated into perbenzylated lactone 13 by lithium-halogen exchange reaction at low temperature (−78° C.). The produced lactols are reduced using triethylsilane and boron trifluoride diethyl etherate to provide bromide intermediates V-2, which are used as starting materials for further derivatizations, as illustrated in Scheme 5. The bromo substituent of intermediate V-2 is converted into a chloro substituent V-3 by the treatment of Cu(I)Cl at heating conditions (120° C.) in quantitative yield. The bromide intermediate V-2 is lithiated with n-BuLi and subsequently reacted with N-fluorobenzenesulfonimide at low temperature (−78° C.) to afford the corresponding fluoride compound V-5. The lithiation of the bromide V-2 followed by the treatment of iodomethane is also applied to prepare a methyl substituted derivative V-7. The bromide V-2 is lithiated and treated with DMF to give a corresponding benzaldehyde, which is reacted with DAST ((diethylamino)sulfur trifluoride) to produce a difluoromethyl substituted compound V-9. The benzaldehyde is converted to a benzyl alcohol with $NaBH_4$, and the benzyl alcohol is treated with DAST to give a monofluoromethyl substituted compound V-11. Benzyl groups are deprotected by hydrogenation using Pd/C under hydrogen atmosphere and then the required β-isomers (V-4, V-6, V-8, V-10, V-12) are separated by prep HPLC equipped with a reverse phase column.
Scheme 6
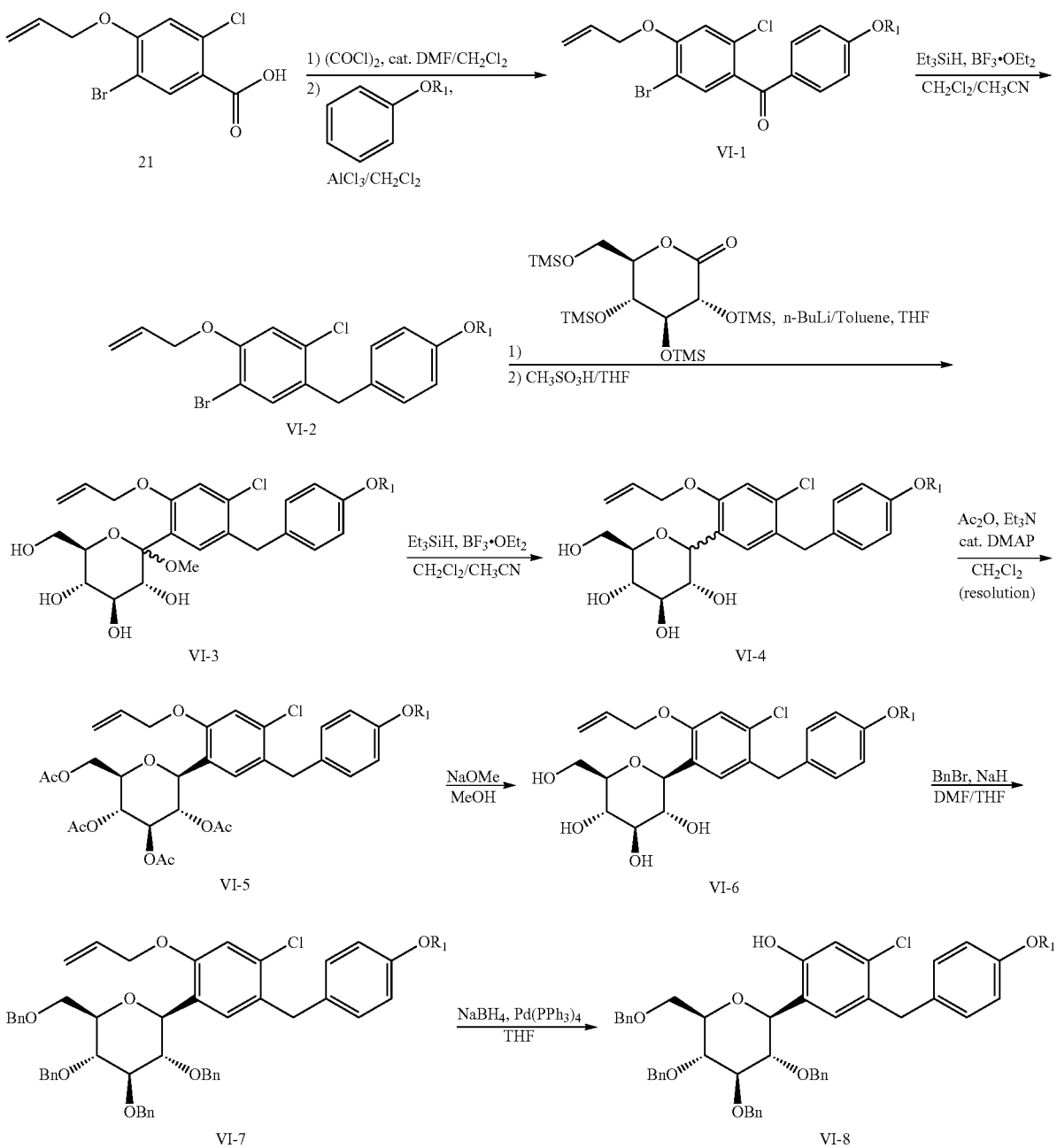
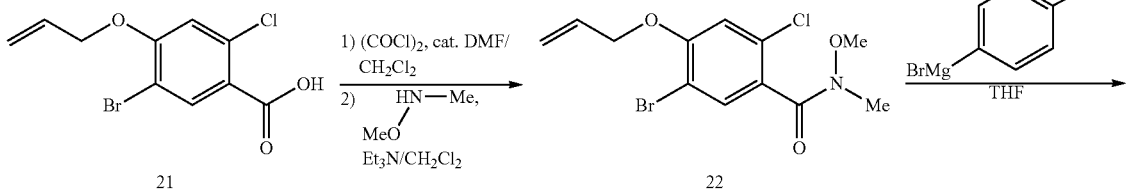

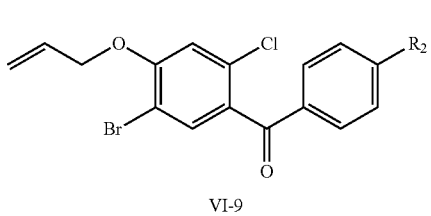

VI-9

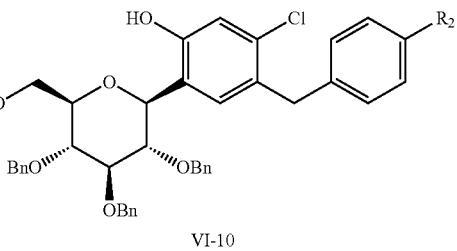

VI-10

Aglycon moieties VI-2, containing an allyloxy group, are prepared from an acid 21 (refer to Scheme 8). The acid 21 is changed into the corresponding acyl chloride with oxalyl chloride, and subsequently coupled with substituted benzenes through the Friedel-Crafts acylation. The produced ketones VI-1 are reduced by triethylsilane in the presence of boron trifluoride etherate to yield aglycons VI-2. The aglycon VI-2 is lithiated by treatment of n-BuLi and coupled with persilylated lactone to produce an α,β-mixture of lactol, which is converted into a desilylated O-methyl lactol VI-3 by methanesulfonic acid. The anomeric methoxy group of compound VI-3 is reduced using triethylsilane and boron trifluoride etherate. After peracetylation, the resulting tetraacetate is recrystallized from ethanol to a pure β-anomer VI-5. Hydrolysis of compound VI-5 with NaOMe generates a tetraol VI-6 in quantitative yield. The tetraols VI-6 are protected by treatment with benzyl bromide and NaH for next reactions. Finally, an allyl group of the perbenzylated intermediate VI-7 is reductively deprotected with NaBH$_4$ and a catalytic amount of Pd(PPh$_3$)$_4$ to yield the key intermediate VI-8, containing phenol moiety.

Case B, in Scheme 6, represents another route to a key intermediate VI-10, which also includes phenol moiety. The same starting material 21 is used to prepare desired ketones VI-9 through Weinreb-amide, and then the similar reactions (from VI-1 to VI-8, in Case A) are applied to produce VI-10 from VI-9.

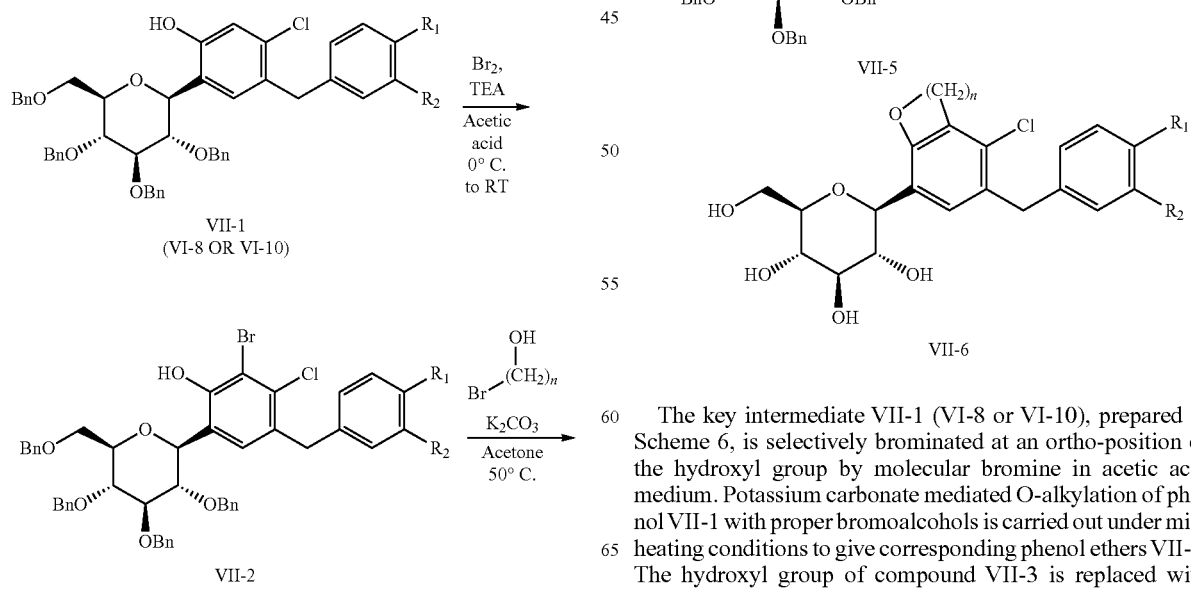

The key intermediate VII-1 (VI-8 or VI-10), prepared in Scheme 6, is selectively brominated at an ortho-position of the hydroxyl group by molecular bromine in acetic acid medium. Potassium carbonate mediated O-alkylation of phenol VII-1 with proper bromoalcohols is carried out under mild heating conditions to give corresponding phenol ethers VII-3. The hydroxyl group of compound VII-3 is replaced with chlorine using triphenylphosphine and CCl$_4$ to produce chlorinated compound VII-4. Treatment of n-BuLi produces heterocyclic compounds VII-5, such as dihydrobenzofuran, via cyclization of aryl bromide onto alkyl chloride. Debenzylation is carried out using Pd/C under hydrogen atmosphere to give final products VII-6.
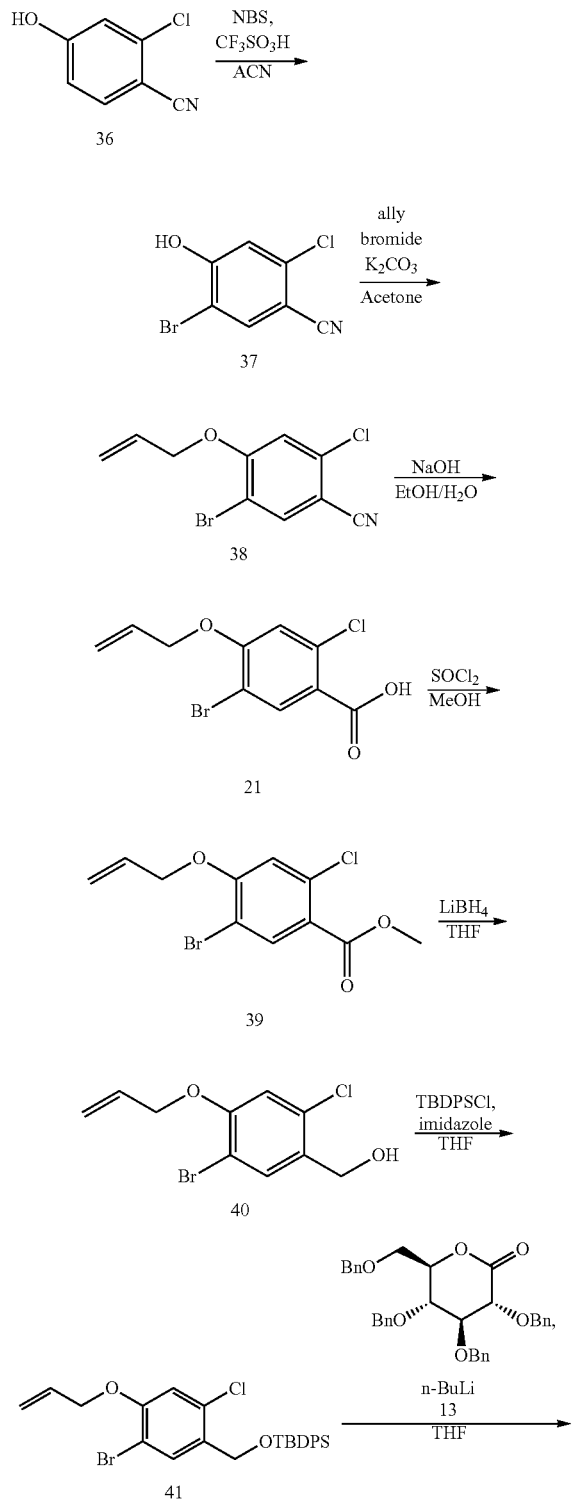
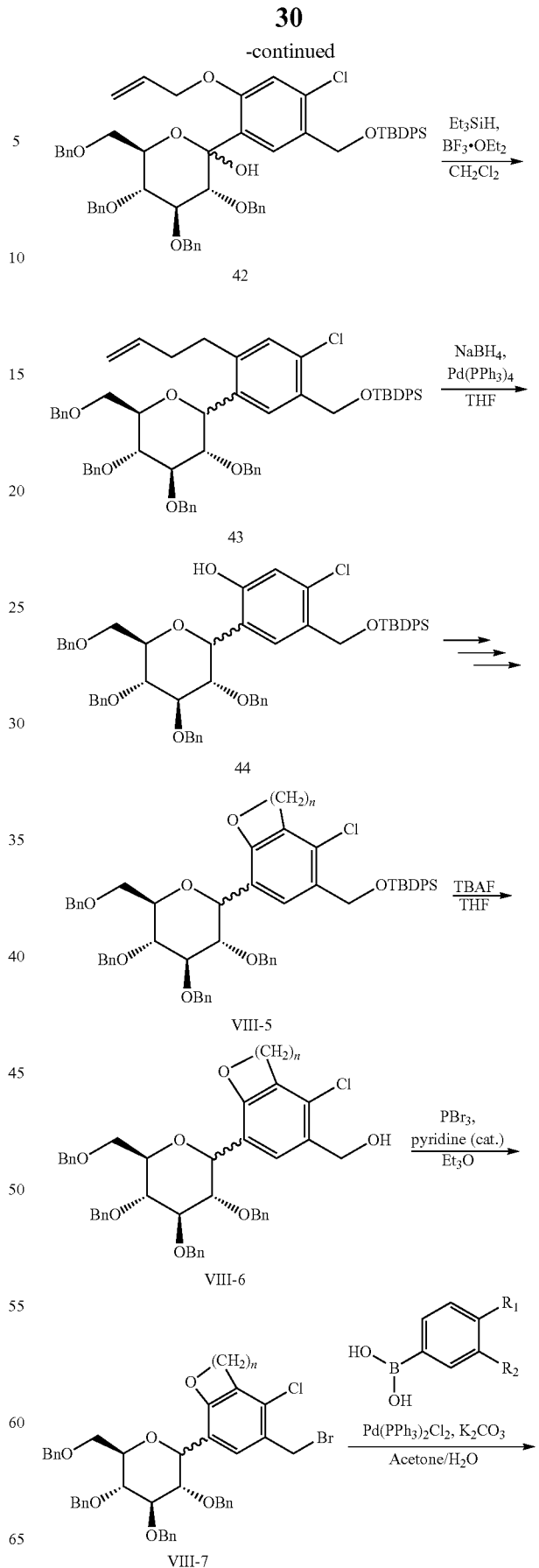

-continued

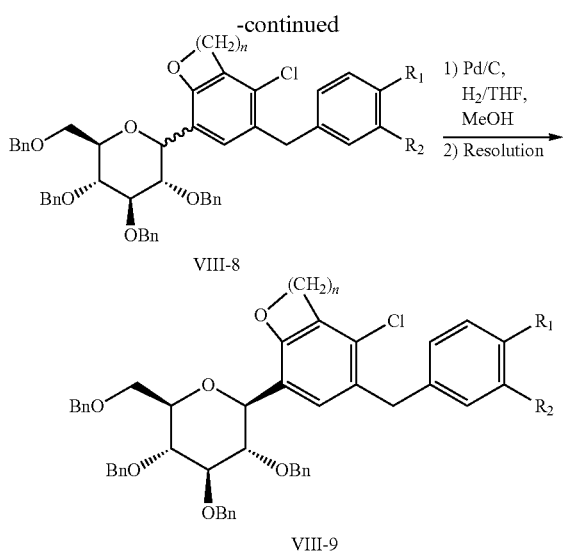

VIII-8

VIII-9

Commercially available cyanide 36 is used as a starting material. The selective monobromintion of compound 36 with NBS in acetonitrile is promoted by CF₃SO₃H. Phenol protection of compound 37 is carried out efficiently with allyl bromide in the presence of $K_2CO_3$. The resulting compound 38 is hydrolyzed with sodium hydroxide in aqueous ethanol, and subsequently converted to the corresponding methylester 39 using $SOCl_2$ and methanol. The silyl-protected alcohol 41 is prepared by reduction of the ester 39 with $LiBH_4$, and subsequent silylation of the resulting alcohol 40 with tert-butyldiphenylchlorosilane (TBDPSCl) in the presence of imidazole.

After lithiation of bromide 41 using n-BuLi, the lithiated aromatic compound is added to perbenzylated gluconolactone to generate a α,β-isomer mixture of the lactols 42. The anomeric alcohol is reduced using triethylsilane and boron trifluoride diethyl etherate, and subsequently the selective deprotection of allyl group is performed by treatment of $NaBH_4$ and $Pd(PPh_3)_4$ to yield the key intermediate 44. A heterocyclic intermediate VIII-5 is prepared by the general procedure, described in Scheme 7 (from VII-1 to VII-5). The cleavage of silyl ether VIII-5 to alcohol VIII-6 using TBAF is followed by replacement of a hydroxyl group with a bromine atom by treatment of $PBr_3$ in the presence of a catalytic amount of pyridine to produce the corresponding benzylbromide VIII-7. Proper phenylboronic acids are coupled with the benzylbromide VIII-7, through palladium-catalyzed reaction, Suzuki coupling, to provide compounds VIII-8, which are debenzylated using Pd/C under hydrogen atmosphere to yield final products VIII-9.

Scheme 9

[Case A]

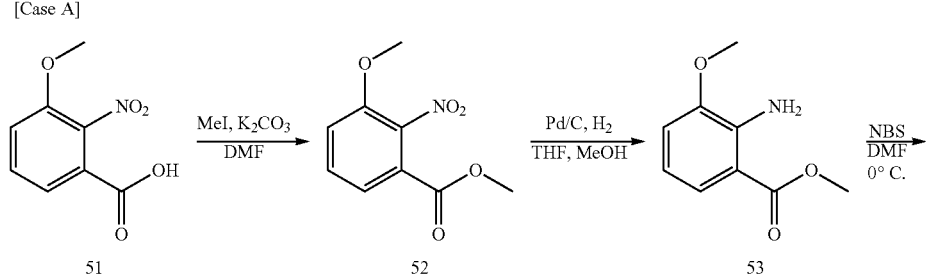

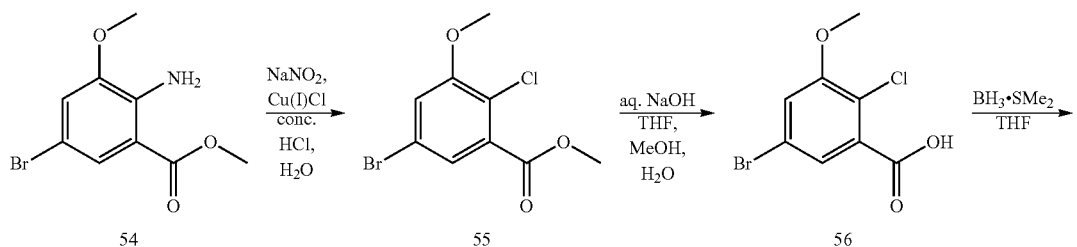

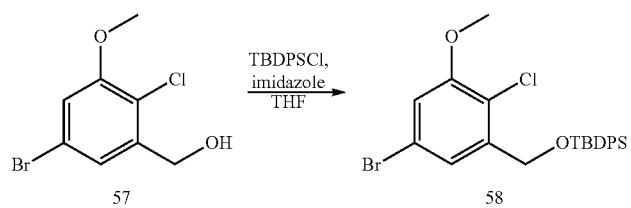

[Case B]

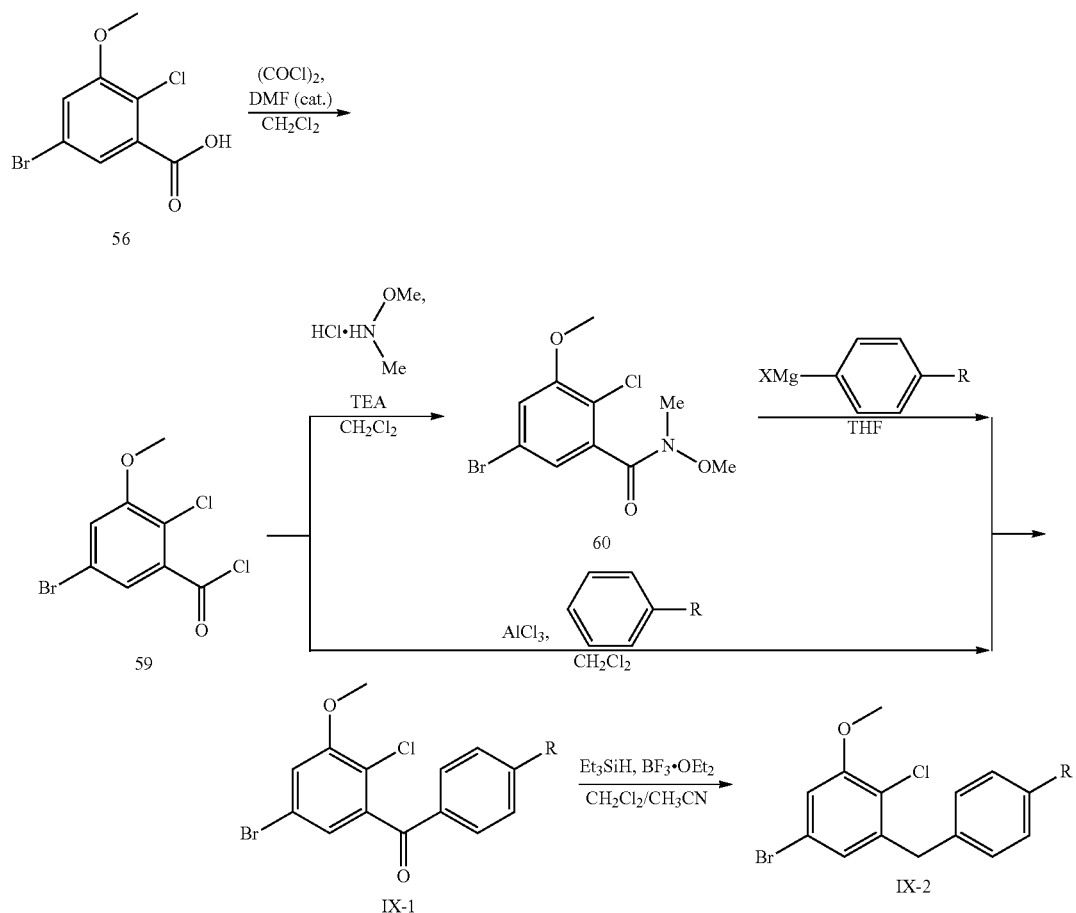

A commercially available acid 51 is converted to the corresponding methyl ester 52 using MeI and K₂CO₃. The nitro group of 52 is changed to an amine group 53 by catalytic reduction under hydrogen atmosphere. Bromination of 53 is performed using a bominating agent such as NBS to obtain compound 54. The amine compound 54 is diazotized with NaNO₂ in acidic conditions, and then chlorinated with Cu(I)Cl to give compound 55. Hydrolysis of compound 55 in basic conditions produces the benzoic acid 56, which is reduced to the benzyl alcohol 57 with borane dimethylsulfide complex. Silyl protection of the benzyl alcohol 57 is carried out using tert-butyldiphenylchlorosilane (TBDPSCl) in the presence of imidazole to provide a key intermediate 58.

As shown in Case B (Scheme 9), another key intermediate IX-2 is prepared from the acid 56, which is already mentioned in Case A (Scheme 9). The acid 56 is converted to the corresponding acyl chloride 59 using oxalyl chloride and DMF as a catalyst, and subsequently coupled with N,O-dimethylhydroxylamine hydrochloride to give Weinreb-amide 60. Reaction of Weinreb amide 60 with proper organometallic nucleophiles, such as Grignard reagents, produces the diarylketones IX-1. On the other hand, the acyl chloride 59 is directly converted into the diarylketone IX-1 through the Friedel-Crafts reaction. The treatment of triethylsilane and boron trifluoride etherate reduces the ketone IX-1 to provide the desired aglycon IX-2.

Scheme 10

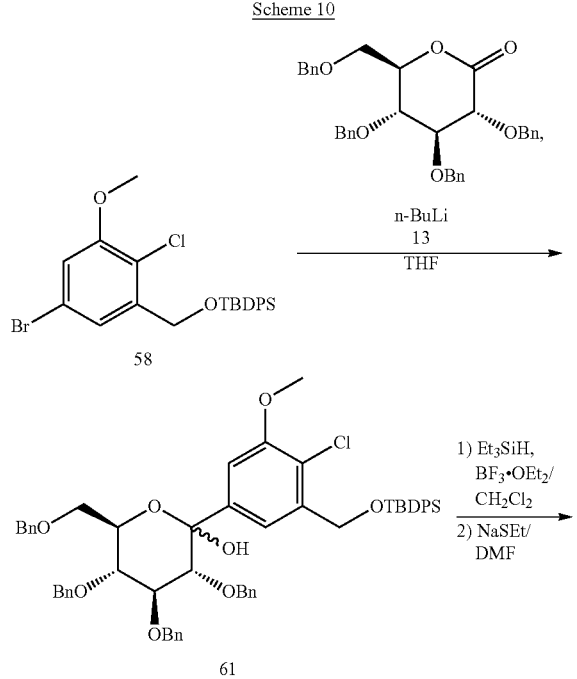

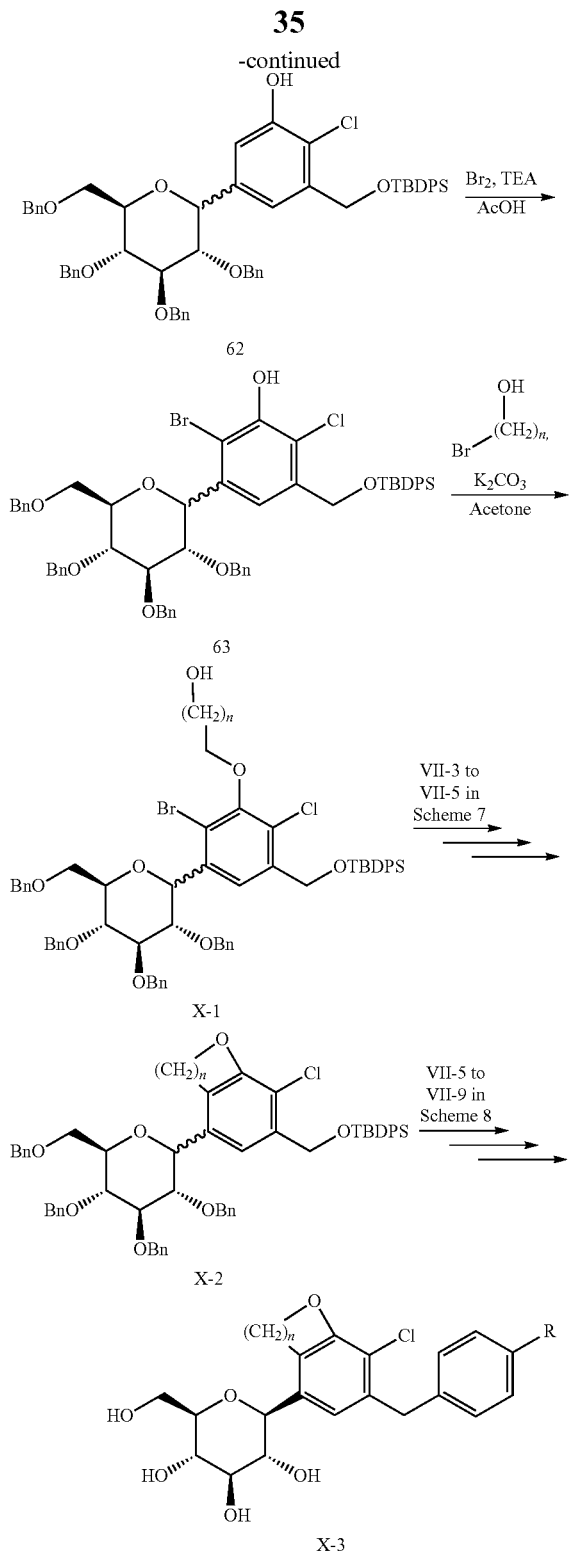

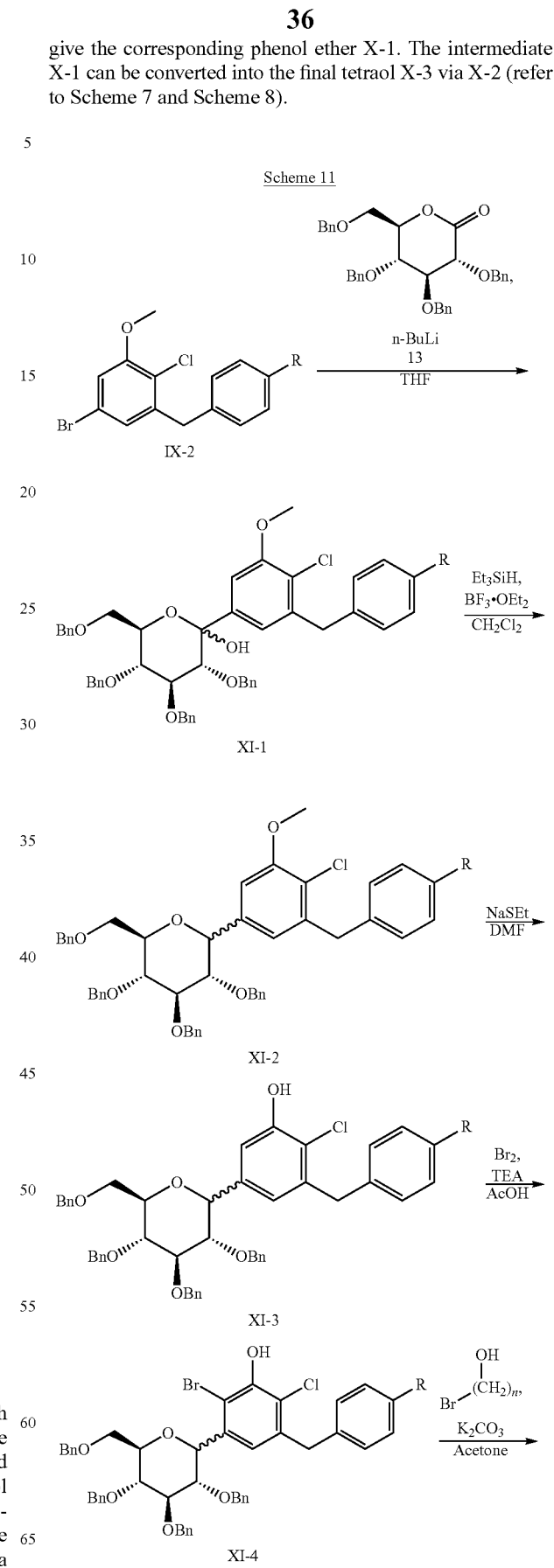

give the corresponding phenol ether X-1. The intermediate X-1 can be converted into the final tetraol X-3 via X-2 (refer to Scheme 7 and Scheme 8).

The bromide 58, prepared in Scheme 9, is lithiated with n-BuLi and is added to perbenzylated gluconolactone, and the resulting lactol is subsequently reduced and demethylated with NaSEt to provide compound 62, containing a phenol moiety. A bromine atom is incorporated into the ortho-position of the phenol using bromine in acetic acid to provide bromophenol 63. O-Alkylation of bromophenol 63 with a proper bromoalcohol is carried out under basic conditions to

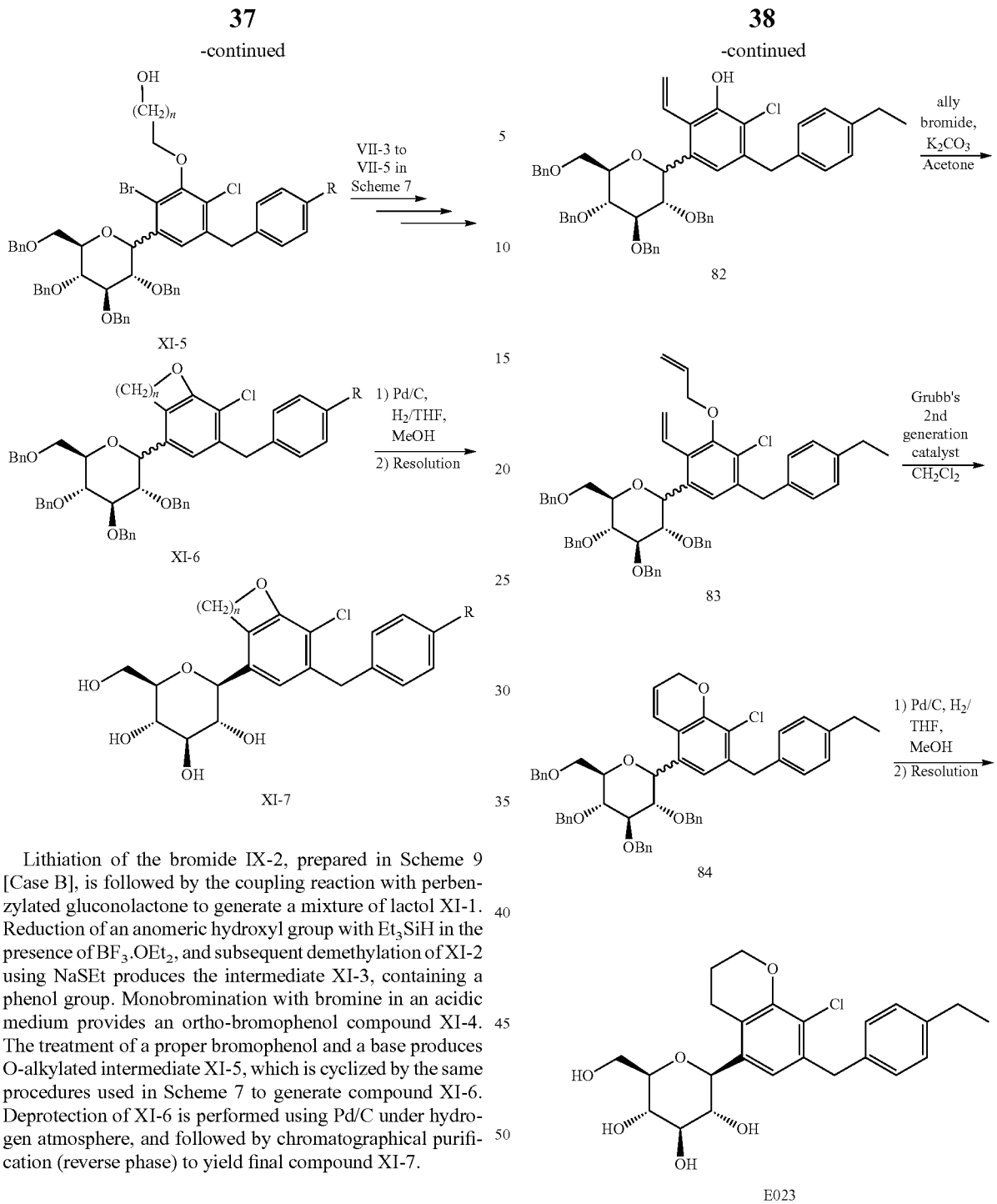

Lithiation of the bromide IX-2, prepared in Scheme 9 [Case B], is followed by the coupling reaction with perbenzylated gluconolactone to generate a mixture of lactol XI-1. Reduction of an anomeric hydroxyl group with $Et_3SiH$ in the presence of $BF_3.OEt_2$, and subsequent demethylation of XI-2 using NaSEt produces the intermediate XI-3, containing a phenol group. Monobromination with bromine in an acidic medium provides an ortho-bromophenol compound XI-4. The treatment of a proper bromophenol and a base produces O-alkylated intermediate XI-5, which is cyclized by the same procedures used in Scheme 7 to generate compound XI-6. Deprotection of XI-6 is performed using Pd/C under hydrogen atmosphere, and followed by chromatographical purification (reverse phase) to yield final compound XI-7.

Scheme 12

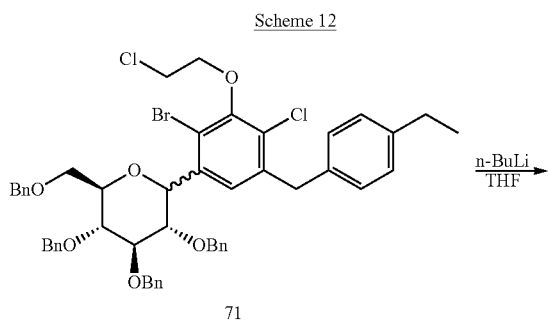

Another synthetic route through the ring-closing metathesis (RCM) is also developed to generate various heterobicyclic moieties, as shown in Scheme 12. Compound 71 is treated with excess n-BuLi to produce an intermediate 82 containing an o-hydroxystyrene moiety. The phenol group of 82 is alkylated with allyl bromide under basic conditions, and followed by RCM using Grubb's $2^{nd}$ generation catalyst to give a cyclized alkenyl compound 84. Hydrogenation using Pd/C under hydrogen atmosphere is performed for debenzylation and alkene reduction to yield a final compound E023.

Scheme 13

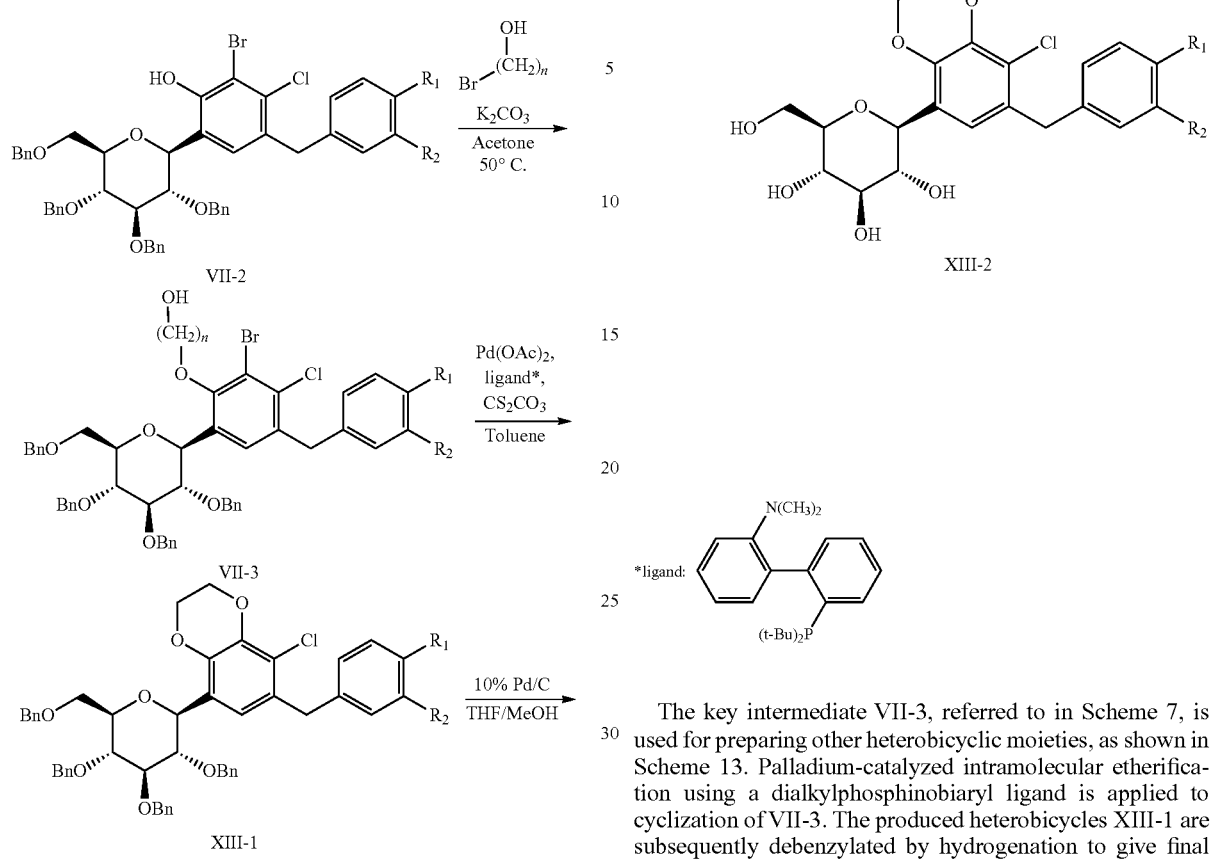

The key intermediate VII-3, referred to in Scheme 7, is used for preparing other heterobicyclic moieties, as shown in Scheme 13. Palladium-catalyzed intramolecular etherification using a dialkylphosphinobiaryl ligand is applied to cyclization of VII-3. The produced heterobicycles XIII-1 are subsequently debenzylated by hydrogenation to give final products XIII-2.

Scheme 14

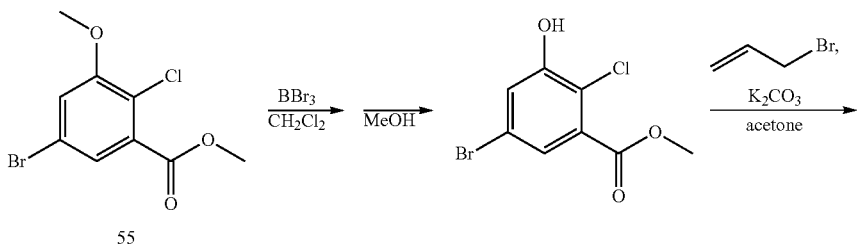

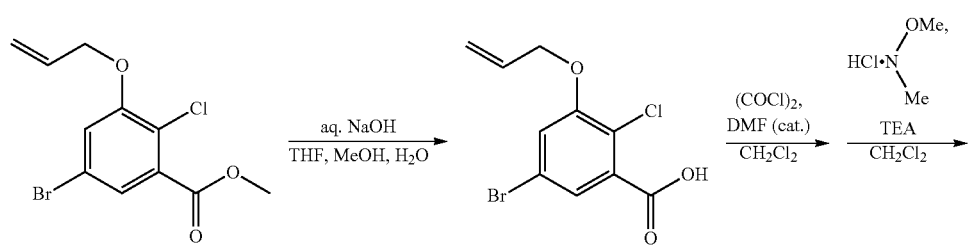

-continued
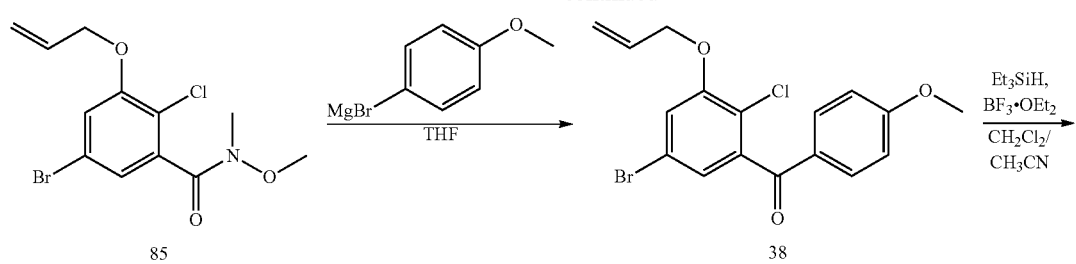
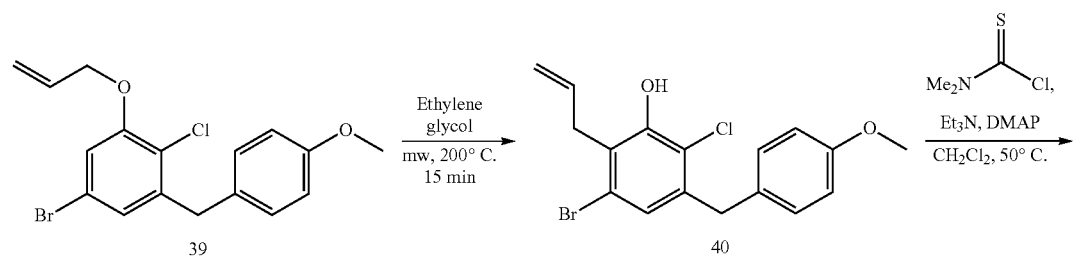
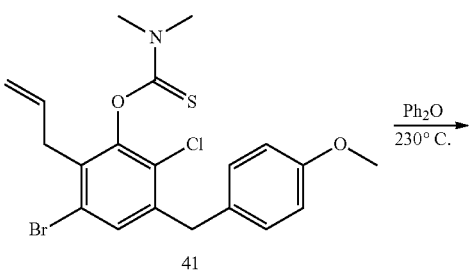
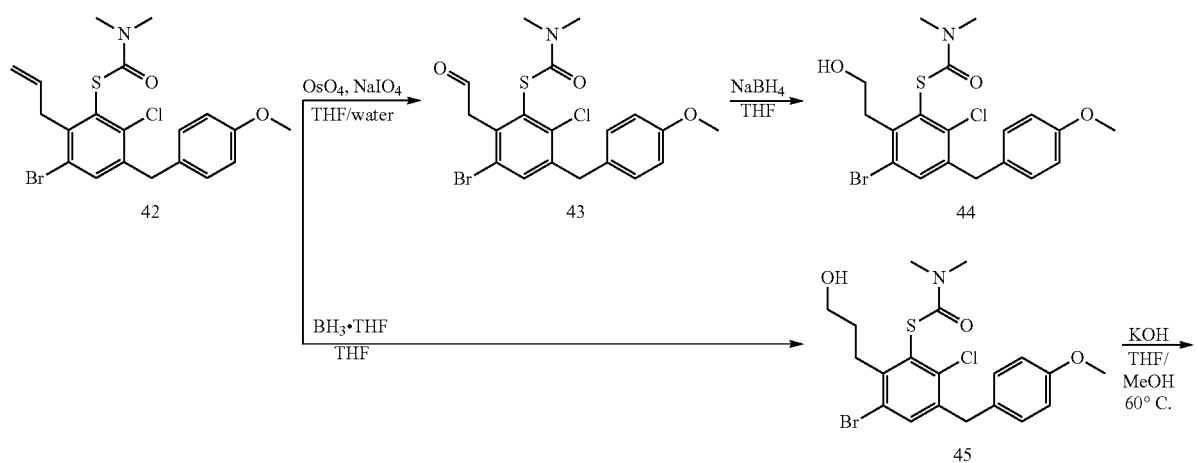
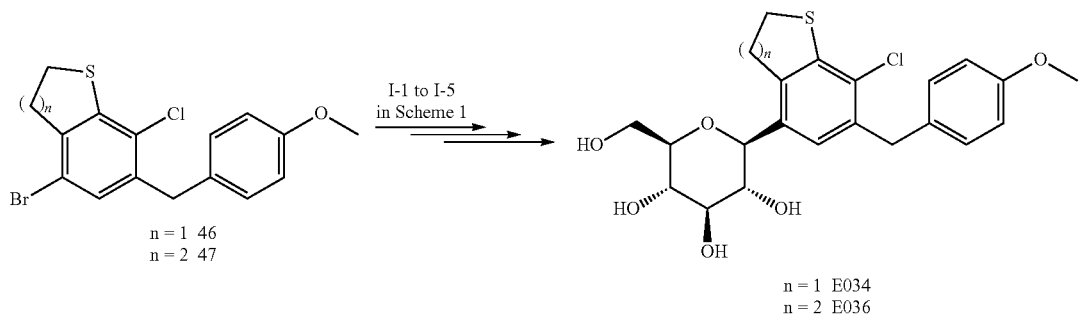

Synthetic routes of sulfur-containing heterobicyclic moieties are illustrated in Scheme 14.

A dihydrobenzothiophene moiety is prepared from compound 55 (refer to Scheme 9). Demethylation of intermediate 55 with BBr₃ and subsequent allylation of 38 under mild heating conditions produce the intermediate 39. Intramolecular migration of an allyl group by microwave radiation is performed to produce the key intermediate 40. Compound 40 is coupled with dimethylthiocarbamoyl chloride in basic conditions to generate a thionoester 41, which is converted into the corresponding thiocarbamate 42 through the Newman-Kwart rearrangement in heating conditions. Oxidation of 42 is followed by allylation in the presence of K₂CO₃ to give compound 94. The cyano group of compound 94 is efficiently converted to the corresponding methyl ester 95 by conventional procedures. Intramolecular cyclization of compound 95 by Grubb's 2$^{nd}$ generation catalyst generates a benzothiophene moiety 96, which is treated with NaOH in aqueous ethanol and oxalyl chloride to produce the corresponding acyl chloride. Friedel-Crafts acylation of the acyl chloride with an aryl compound generates the diarylketone 98. Reduction of the ketone 98 with Et₃SiH and BF₃.OEt₂ gives the desired aglycon 99. This aglycon 99 is coupled with the gluconolactone, deprotected, reduced, and purified to the final compound E048 (refer to Scheme 1).

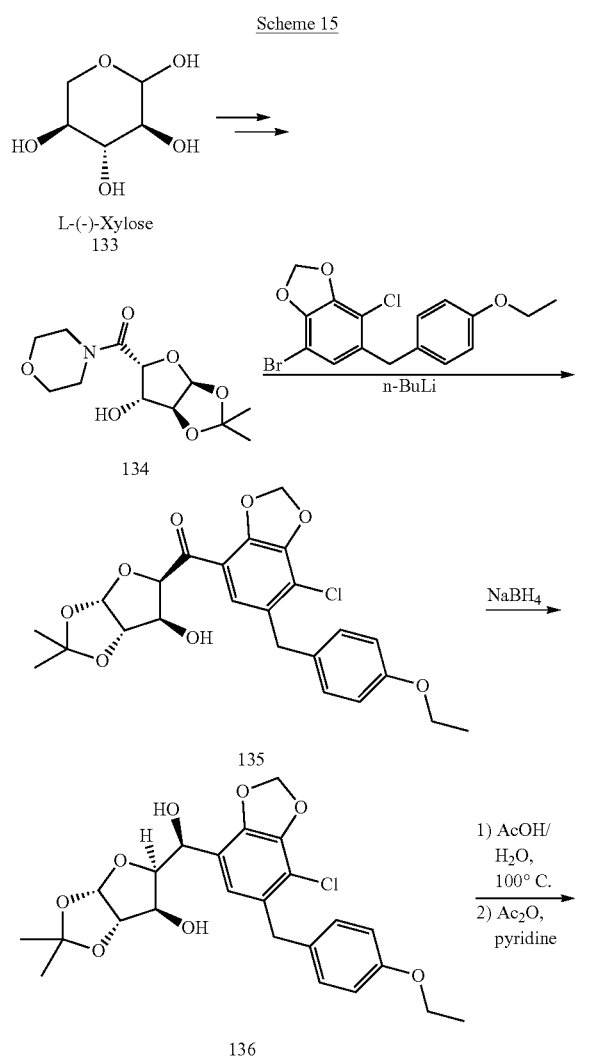

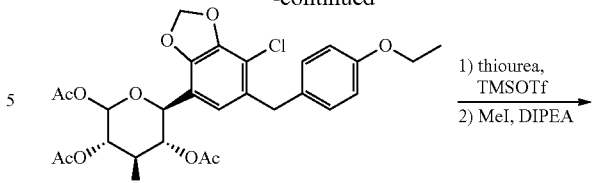

137

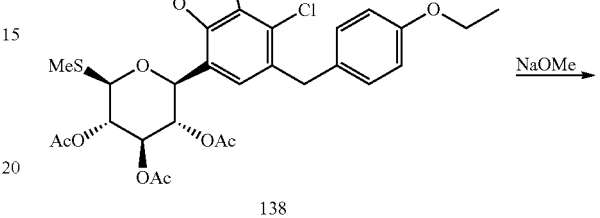

138

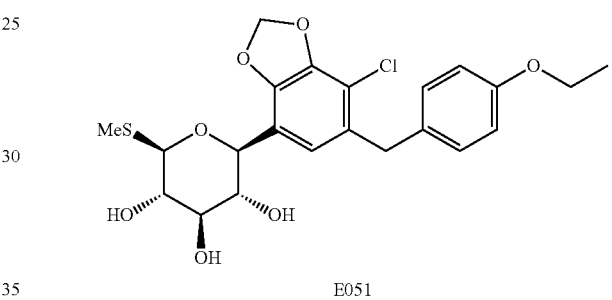

E051

As shown in Scheme 15, the main sugar core is changed from D-glucose to L-xylose. A morpholino amide 134 is provided from L-xylose 133 through the known procedures (WO 2009/014970 A1). A halogenated aglycon is coupled by the treatment of n-BuLi with the morpholino amide 134 to generate a ketone 135, which is subsequently reduced to the corresponding alcohol, key intermediate 136, by NaBH₄. In acidic conditions, the furanose 136 is changed to a pyranose, and then acetylated by a conventional procedure to give a peracetylated compound 137. A thiomethyl group is directly incorporated into the intermediate 137 by the treatment of thiourea and TMSOTf, followed by addition of MeI and DIPEA. The resulting methanthiopyranose 138 is deacetylated using NaOMe to give the final product E051.

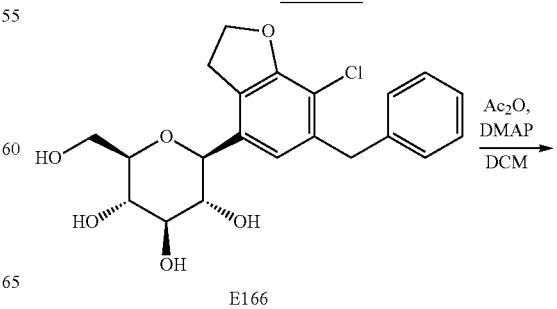

E166

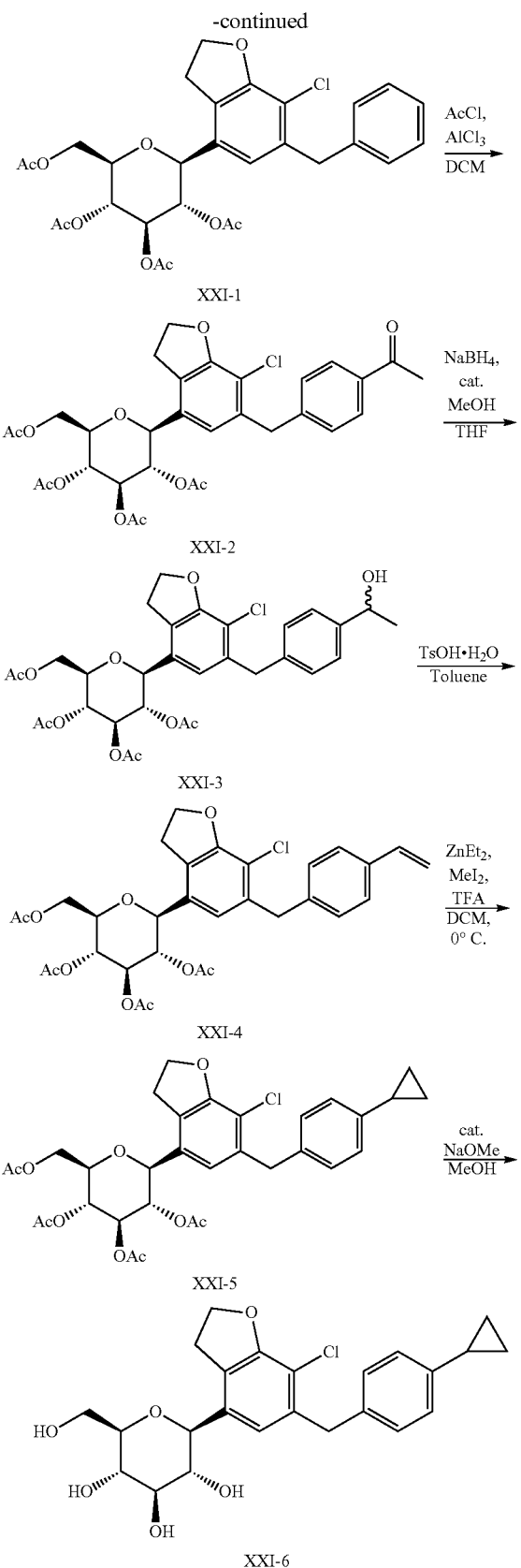

As shown in Scheme 16, various substituents, such as acetyl, hydroxyethyl, vinyl and cyclopropyl, are incorporated into para-position of the non-substituted phenyl ring (*Bioorg. Med. Chem. Lett.* 2011, 21, 4465-4470).

The present invention is further described and illustrated in Examples provided below, which are, however, not intended to limit the scope of the present invention.

EXPERIMENTAL SECTION

As used herein the symbols and conventions used describing the processes, schemes and examples of the present invention are consistent with those used in the contemporary scientific literature, for example, the *Journal of the American Chemical Society* or the *Journal of Biological Chemistry*.

| | |
|---|---|
| Hz (Hertz) | TLC (thin layer chromatography) |
| $T_r$ (retention time) | RP (reverse phase) |
| MeOH (methanol) | i-PrOH (isopropanol) |
| TFA (trifluoroacetic acid) | TEA (triethylamine) |
| EtOH (ethanol) | THF (tetrahydrofuran) |
| DMSO (dimethylsulfoxide) | EtOAc (ethyl acetate) |
| DCM (dichloromethane) | HOAc (acetic acid) |
| DMF (N,N-dimethylformamide) | Ac (acetyl) |
| CDI (1,1-carbonyldiimidazole) | Bn (benzyl) |
| TES (Triethylsilyl) | NBS (N-Bromosuccinimide) |
| HOBt (1-hydroxybenzotriazole) | |
| Boc (tert-butyloxycarbonyl) | |
| mCPBA (meta-chloroperbenzoic acid) | |
| NMM (N-methyl morpholine) | |
| TBAF (tetra-n-butylammonium fluoride) | |
| DMAP (4-dimethylaminopyridine) | |
| HPLC (high performance liquid chromatography) | |
| EDCI (1-ethyl-3-[3-dimethylaminopropyl]carbodiimide hydrochloride) | |
| DME (1,2-dimethoxyethane) | |
| AIBN (2,2'-azobis(2-methylpropionitrile)) | |
| DIEA (N,N'-diisopropylethylamine) | |
| TIPSCl (triisopropylsilyl chloride) | |
| TIPSOTf (triisopropylsilyl trifluoromethanesulfonate) | |
| TMSI (iodotrimethylsilane) | |
| TMSOTf (trimethylsilyl trifluoromethanesulfonate) | |
| DDQ (2,3-dichloro-5,6-dicyano-p-benzoquinone) | |
| DAST (diethylaminosulfur trifluoride) | |
| NMP (1-methyl-2-pyrrolidinone) | |
| MW (micrwave irradiation) | |

All reactions are conducted under an inert atmosphere at room temperature, unless otherwise noted. n-Butyllithium (Aldrich) was titrated with N-benzylbenzamide as indicator. All reagents were purchased at the highest commercial quality and used without further purification, unless otherwise indicated. All experiment involving moisture- and/or air-sensitive compounds were performed in oven- and/or flame-dried glassware with rubber septa under a positive pressure of nitrogen using standard Schlenck technique. Microwave reaction was conducted with a Biotage Initiator microwave reactor. NMR spectra were obtained on a Varian 400-MR (400 MHz $^1$H, 100 MHz $^{13}$C) spectrometer or a Bruker Ultrashield 400 plus (400 MHz $^1$H, 100 MHz $^{13}$C) spectrometer. NMR spectra were recorded in ppm (δ) relative to tetramethylsilane (δ=0.00) as an internal standard unless stated otherwise and are reported as follows: chemical shift, multiplicity (s=singlet, d=doublet, t=triplet, q=quartet, quint=quintet, sext=sextet, m=multiplet, and br=broad), coupling constant, and integration. $^{13}$C NMR spectra were referenced to the residual chloroform-d$_1$ (δ=77.0) or DMSO-d$_6$ (δ=39.7). Mass spectra were obtained with an Agilent 6110 quadruple LC-MSD (ESI+). High resolution mass spectra were obtained on a Jeol JMS-700 Mstation (10 kV, HFAB). Optical rotations were obtained on a Rudolph Autopol III digital polarimeter. Preparative HPLC purifications were performed on a Gilson purification system. For preparative HPLC, ca. 100 mg of a product was injected in 1 mL of methanol onto a SunFire Prep C18 OBD 5 μm 30×100 mm Column with a 30 min gradient from 5 to 90% acetonitrile in water and a 45 mL/min flow rate. Biotage SP1 and Isolera purification systems were used for normal phase column chromatography with ethyl acetate and hexane. Flash chromatography was performed using E. Merck 230-400 mesh silica gel according to the procedure of Still et al. Reactions were monitored by either thin-layer chromatography (TLC) on 0.25 mm E. Merck silica gel plates (60F-254) using UV light and p-anisaldehyde solution as visualizing agents or HPLC analysis on an Agilent 1200 series system.

The following synthetic schemes are merely illustrative of the methods by which the compounds of the invention may be prepared and are not intended to limit the scope of the invention as defined in the appended claims.

Example 001

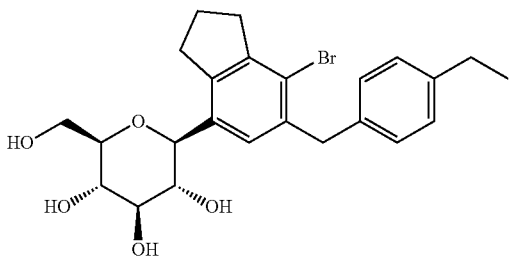 [SMILES: CCc1ccc(Cc2cc([C@@H]3O[C@H](CO)[C@@H](O)[C@H](O)[C@H]3O)c3c(c2Br)CCC3)cc1]

(2S,3R,4R,5S,6R)-2-(7-Bromo-6-(4-methoxybenzyl)-2,3-dihydro-1H-inden-4-yl)-6-(hydroxymethyl)tetrahydro-2H-pyran-3,4,5-triol (E001)

To a solution of compound 15 (0.94 g, 1.85 mmol) in $CH_2Cl_2/CH_3CN$ (8.9 mL/8.9 mL) were added triethylsilane (0.59 mL, 3.7 mmol) and boron trifluoride diethyl etherate (0.46 mL, 3.7 mmol) at −60° C. under nitrogen atmosphere. The mixture was warmed up to −30° C. for 2 h. The reaction mixture was quenched with saturated $NaHCO_3$ solution (15 mL) and extracted with EtOAc (50 mL). The organic layer was washed with brine, dried over anhydrous $MgSO_4$, filtered and concentrated in vacuo. The residue was purified by prep HPLC (reverse phase) to provide the compound E001 (0.15 g, 0.306 mmol, 17%).

$^1$H NMR (400 MHz, $CD_3OD$) δ 7.12 (s, 1H), 7.07 (d, J=8.4 Hz, 2H), 6.77 (d, J=8.8 Hz, 2H), 4.19 (d, J=9.2 Hz, 1H), 3.98 (ABq, $Δv_{AB}$=15.3 Hz, $J_{AB}$=15.2 Hz, 2H), 3.84 (d, J=10.8 Hz, 1H), 3.72 (s, 3H), 3.66-3.62 (m, 1H), 3.44-3.40 (m, 2H), 3.38-3.32 (m, 2H), 3.22-3.14 (m, 1H), 3.08-3.01 (m, 1H), 2.92 (t, J=7.6 Hz, 2H), 2.06 (m, 2H); [M-OH]$^+$ 461.

Example 002

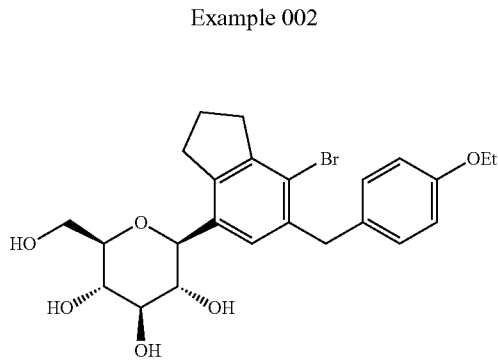

(2S,3R,4R,5S,6R)-2-(7-Bromo-6-(4-ethoxybenzyl)-2,3-dihydro-1H-inden-4-yl)-6-(hydroxymethyl)tetrahydro-2H-pyran-3,4,5-triol (E002)

$^1$H NMR (400 MHz, $CD_3OD$) δ 7.12 (s, 1H), 7.06 (d, J=8.4 Hz, 2H), 6.75 (d, J=8.8 Hz, 2H), 4.19 (d, J=9.6 Hz, 1H), 4.00 (ABq, $Δv_{AB}$=15.3 Hz, $J_{AB}$=15.2 Hz, 2H), 3.96 (q, J=6.8 Hz, 2H), 3.84 (d, J=11.2 Hz, 1H), 3.66-3.62 (m, 1H), 3.44-3.40 (m, 2H), 3.38-3.33 (m, 2H), 3.22-3.13 (m, 1H), 3.08-3.01 (m, 1H), 2.92 (t, J=7.6 Hz, 2H), 2.06 (m, 2H), 1.33 (t, J=6.8 Hz, 3H); [M-OH]$^+$ 475.

Example 003

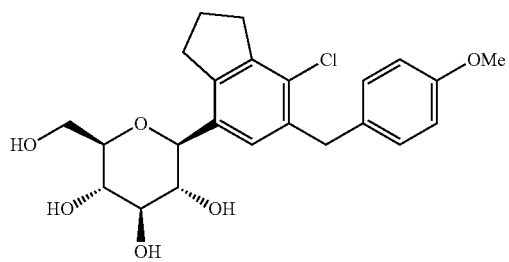

(2S,3R,4R,5S,6R)-2-(7-Bromo-6-(4-ethylbenzyl)-2,3-dihydro-1H-inden-4-yl)-6-(hydroxymethyl)tetrahydro-2H-pyran-3,4,5-triol (E003)

$^1$H NMR (400 MHz, $CD_3OD$) δ 7.20 (s, 1H), 7.12 (ABq, $Δv_{AB}$=7.4 Hz, $J_{AB}$=8.4 Hz, 4H), 4.26 (d, J=9.2 Hz, 1H), 4.11 (ABq, $Δv_{AB}$=14.8 Hz, $J_{AB}$=15.2 Hz, 2H), 3.91 (d, J=11.6 Hz, 1H), 3.73-3.68 (m, 1H), 3.52-3.47 (m, 2H), 3.44-3.40 (m, 2H), 3.29-3.21 (m, 1H), 3.16-3.07 (m, 1H), 3.00 (t, J=7.6 Hz, 2H), 2.63 (t, J=7.6 Hz, 2H), 2.13 (m, 2H), 1.24 (t, J=7.6 Hz, 3H); [M-OH]$^+$ 459.

Example 004

(2S,3R,4R,5S,6R)-2-(7-Chloro-6-(4-methoxybenzyl)-2,3-dihydro-1H-inden-4-yl)-6-(hydroxymethyl)tetrahydro-2H-pyran-3,4,5-triol (E004)

To a solution of compound 18 (0.87 g, 1.09 mmol) in THF/MeOH (8.9 mL/8.9 mL) were added Pd/C (10% Pd, 122 mg). The mixture was stirred at rt under hydrogen atmosphere for 15 h. The catalyst removed by filtration, and then the filtrate was concentrated in vacuo. The residue was purified by prep HPLC (reverse phase) to provide the compound E004 (0.11 g, 0.25 mmol, 23%).

¹H NMR (400 MHz, CD₃OD) δ 7.16 (s, 1H), 7.09 (d, J=8.8 Hz, 2H), 6.79 (d, J=8.8 Hz, 2H), 4.22 (d, J=6.4 Hz, 1H), 3.99 (ABq, Δv$_{AB}$=16.5 Hz, J$_{AB}$=15.2 Hz, 2H)), 3.86 (d, J=8.0 Hz, 1H), 3.74 (s, 3H), 3.68-3.63 (m, 1H), 3.48-3.44 (m, 2H), 3.38-3.34 (m, 2H), 3.19-3.11 (m, 1H), 3.06-2.98 (m, 1H), 2.94 (t, J=7.6 Hz, 2H), 2.081 (m, 2H); [M+Na]⁺ 457.

Example 005

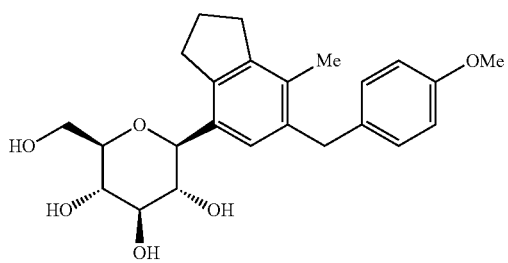

(2R,3S,4R,5R,6S)-2-(Hydroxymethyl)-6-(6-(4-methoxybenzyl)-7-methyl-2,3-dihydro-1H-inden-4-yl)tetrahydro-2H-pyran-3,4,5-triol (E005)

¹H NMR (400 MHz, CD₃OD) δ 7.05 (s, 1H), 7.00 (d, J=8.8 Hz, 2H), 6.76 (d, J=8.8 Hz, 2H), 4.23 (d, J=9.6 Hz, 1H), 3.90 (s, 2H), 3.86 (d, J=12.0 Hz, 1H), 3.72 (s, 1H), 3.68-3.64 (m, 1H), 3.54 (t, J=8.8 Hz, 1H), 3.49-3.44 (m, 1H), 3.39-3.35 (m, 2H), 3.11-3.03 (m, 1H), 3.00-2.92 (m, 1H), 2.82 (t, J=7.6 Hz, 2H), 2.08-2.00 (m, 5H); [M+Na]⁺ 437.

Example 006

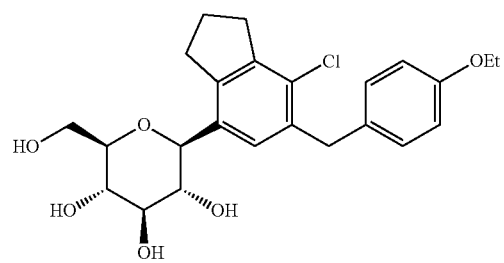 [SMILES: CCOc1ccc(Cc2cc([C@@H]3O[C@H](CO)[C@@H](O)[C@H](O)[C@H]3O)c3c(c2Cl)CCC3)cc1]

(2S,3R,4R,5S,6R)-2-(7-Chloro-6-(4-ethoxybenzyl)-2,3-dihydro-1H-inden-4-yl)-6-(hydroxymethyl)tetrahydro-2H-pyran-3,4,5-triol (E006)

¹H NMR (400 MHz, CD₃OD) δ 7.16 (s, 1H), 7.08 (d, J=8.8 Hz, 2H), 6.77 (d, J=8.8 Hz, 2H), 4.21 (d, J=9.6 Hz, 1H), 4.04-3.94 (m, 4H), 3.87 (d, J=11.2 Hz, 1H), 3.69-3.63 (m, 1H), 3.48-3.43 (m, 2H), 3.38-3.34 (m, 2H), 3.19-3.11 (m, 1H), 3.06-2.98 (m, 1H), 2.94 (t, J=7.2 Hz, 2H), 2.082 (m, 2H), 1.35 (t, J=6.8 Hz, 3H); [M+Na]⁺ 471.

Example 007

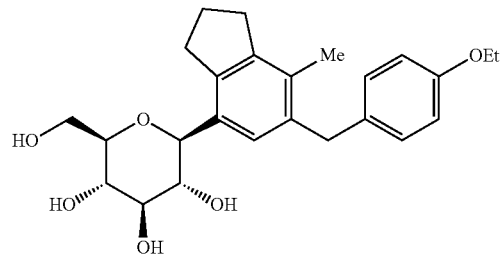 [SMILES: CCOc1ccc(Cc2cc([C@@H]3O[C@H](CO)[C@@H](O)[C@H](O)[C@H]3O)c3c(c2C)CCC3)cc1]

(2S,3R,4R,5S,6R)-2-(6-(4-Ethoxybenzyl)-7-methyl-2,3-dihydro-1H-inden-4-yl)-6-(hydroxymethyl)tetrahydro-2H-pyran-3,4,5-triol (E007)

¹H NMR (400 MHz, CD₃OD) δ 7.06 (s, 1H), 7.00 (d, J=8.8 Hz, 2H), 6.76 (d, J=8.8 Hz, 2H), 4.24 (d, J=9.2 Hz, 1H), 3.97 (q, J=6.8 Hz, 2H), 3.91 (s, 2H), 3.88 (d, J=12.4 Hz, 1H), 3.69-3.64 (m, 1H), 3.55 (t, J=8.8 Hz, 1H), 3.50-3.45 (m, 1H), 3.40-3.36 (m, 2H), 3.13-3.04 (m, 1H), 3.01-2.93 (m, 1H), 2.83 (t, J=7.2 Hz, 2H), 2.09-2.02 (m, 5H), 1.35 (t, J=7.2 Hz, 3H); [M+H]⁺ 451.

Example 008

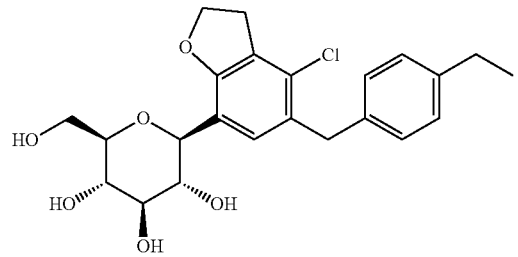

(2S,3R,4R,5S,6R)-2-(4-Chloro-5-(4-ethylbenzyl)-2,3-dihydrobenzofuran-7-yl)-6-(hydroxymethyl)tetrahydro-2H-pyran-3,4,5-triol (E008)

To a solution of compound 35 (1.03 g, 1.30 mmol) in THF/MeOH (30 mL/30 mL) was added Pd/C (10% Pd, 154 mg). The mixture was stirred at rt under hydrogen atmosphere for 15 h. The catalyst removed by filtration, and then the filtrate was concentrated in vacuo. The residue was purified by prep HPLC (reverse phase) to provide the compound E008 (0.28 g, 0.64 mmol, 49%).

¹H NMR (400 MHz, CD₃OD) δ 7.12 (s, 1H), 7.07 (s, 4H), 4.61 (sext, J=8.8 Hz, 2H), 4.30 (d, J=9.6 Hz, 1H), 3.97 (ABq, Δv$_{AB}$=9.6 Hz, J$_{AB}$=15.2 Hz, 2H), 3.84 (dd, J=12.0, 1.6 Hz, 1H), 3.67-3.62 (m, 1H), 3.59 (t, J=14.8 Hz, 1H), 3.45-3.39 (m, 1H), 3.37-3.40 (m, 2H), 3.23 (t, J=8.4 Hz, 2H), 2.58 (q, J=7.6 Hz, 2H), 1.19 (t, J=7.6 Hz, 3H); [M+Na]⁺ 457.

Example 009

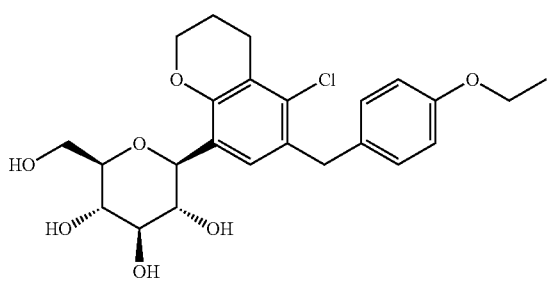 [SMILES: CCOc1ccc(Cc2cc([C@@H]3O[C@H](CO)[C@@H](O)[C@H](O)[C@H]3O)c3c(c2Cl)CCCO3)cc1]

(2S,3R,4R,5S,6R)-2-(5-Chloro-6-(4-ethoxybenzyl)chroman-8-yl)-6-(hydroxymethyl)tetrahydro-2H-pyran-3,4,5-triol (E009)

To a solution of compound 30 (255 mg, 0.309 mmol) in THF/MeOH (15 mL/15 mL) was added 10% Pd/C (71 mg) at rt. The reaction mixture was stirred at r.t. for 15 hours under hydrogen and filtered off. The filtrate was concentrated in vacuo and the residue was purified using reverse phase preparative HPLC to provide the title compound E009 (51 mg, 36%).

$^1$H NMR (400 MHz, CD$_3$OD) δ 7.19 (s, 1H), 7.06 (d, J=8.8 Hz, 2H), 6.77 (d, J=8.7 Hz, 2H), 4.90 (s, 4H), 4.66-4.55 (m, 1H), 4.19-4.06 (m, 2H), 3.98 (q, J=7.0 Hz, 2H), 3.93 (ABq, Δv$_{AB}$=10.4 Hz, J$_{AB}$=15.2 Hz, 2H), 3.84 (d, J=10.6 Hz, 1H), 3.69-3.61 (m, 1H), 3.50-3.43 (m, 2H), 3.41-3.32 (m, 2H), 2.79 (t, J=6.6 Hz, 2H), 2.05-1.96 (m, 2H), 1.35 (t, J=7.0 Hz, 3H); [M+Na]$^+$ 487.

Example 010

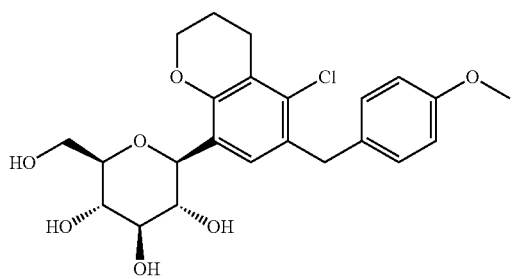

(2S,3R,4R,5S,6R)-2-(5-Chloro-6-(4-methoxybenzyl)chroman-8-yl)-6-(hydroxymethyl)tetrahydro-2H-pyran-3,4,5-triol (E010)

$^1$H NMR (400 MHz, CD$_3$OD) δ 7.19 (s, 1H), 7.08 (d, J=8.8 Hz, 2H), 6.79 (d, J=8.7 Hz, 2H), 4.87 (s, 4H), 4.64-4.57 (m, 1H), 4.21-4.07 (m, 2H), 3.96 (ABq, Δv$_{AB}$=13.3 Hz, J$_{AB}$=15.2 Hz, 2H), 3.84 (d, J=10.4 Hz, 1H), 3.75 (s, 3H), 3.71-3.60 (m, 1H), 3.49-3.42 (m, 2H), 3.38-3.33 (m, 2H), 2.79 (t, J=6.6 Hz, 2H), 2.04-1.96 (m, 2H); [M+Na]$^+$ 473.

Example 011

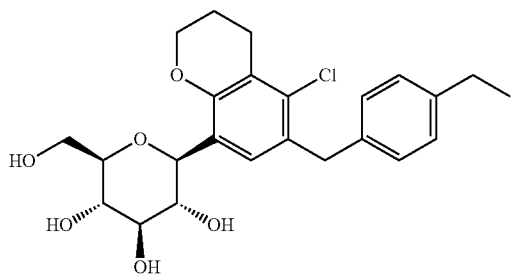

(2S,3R,4R,5S,6R)-2-(5-Chloro-6-(4-ethylbenzyl)chroman-8-yl)-6-(hydroxymethyl)tetrahydro-2H-pyran-3,4,5-triol (E011)

$^1$H NMR (400 MHz, CD$_3$OD) δ 7.23 (s, 1H), 7.09 (s, 4H), 4.92 (s, 4H), 4.68-4.61 (m, 1H), 4.24-4.11 (m, 2H), 4.02 (ABq, Δv$_{AB}$=11.8 Hz, J$_{AB}$=15.1 Hz, 2H), 3.87 (d, J=10.6 Hz, 1H), 3.73-3.62 (m, 1H), 3.53-3.47 (m, 2H), 3.43-3.31 (m, 2H), 2.82 (t, J=6.6 Hz, 2H), 2.60 (q, J=7.6 Hz, 2H), 2.07-2.01 (m, 2H), 1.22 (t, J=7.6 Hz, 3H); [M+Na]$^+$ 471.

Example 012

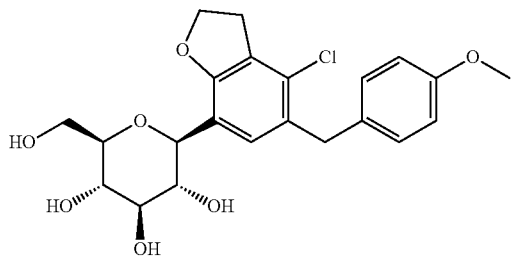

(2S,3R,4R,5S,6R)-2-(4-Chloro-5-(4-methoxybenzyl)-2,3-dihydrobenzofuran-7-yl)-6-(hydroxymethyl)tetrahydro-2H-pyran-3,4,5-triol (E012)

A suspension of compound 50 (407 mg, 0.51 mmol) and Pd/C (10% wt., 50 mg) in THF (5.0 mL) and MeOH (2.5 mL) was stirred at room temperature under an atmosphere of H$_2$ for 24 hours. The mixture was filtered through a Celite pad and concentrated in vacuo. The residue was purified by prep HPLC(C18) to afford the product E012 (65 mg, 27%) as a white solid.

$^1$H NMR (400 MHz, DMSO-d$_6$) δ 7.12 (s, 1H), 7.04 (dt, J=8.2, 2.4 Hz, 2H), 6.79 (dt, J=8.2, 2.4 Hz, 2H), 4.65-4.54 (m, 2H), 4.31 (d, J=9.6 Hz, 1H), 3.94 (ABq, Δv$_{AB}$=10.4 Hz, $J_{AB}$=15.2 Hz, 2H), 3.85 (dd, J=11.8, 1.8 Hz, 1H), 3.76 (s, 3H), 3.68-3.57 (m, 2H), 3.46-3.35 (m, 3H), 3.21 (t, J=8.6 Hz, 2H); [M+Na]$^+$ 459.

Example 013

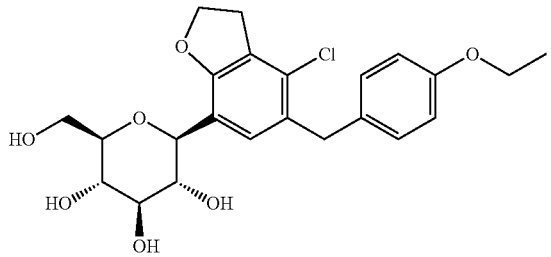 [SMILES: CCOc1ccc(Cc2cc([C@@H]3O[C@H](CO)[C@@H](O)[C@H](O)[C@H]3O)c3c(c2Cl)CCO3)cc1]

(2S,3R,4R,5S,6R)-2-(4-Chloro-5-(4-ethoxybenzyl)-2,3-dihydrobenzofuran-7-yl)-6-(hydroxymethyl)tetrahydro-2H-pyran-3,4,5-triol (E013)

$^1$H NMR (400 MHz, DMSO-d$_6$) δ 7.12 (s, 1H), 7.08 (d, J=8.8 Hz, 2H), 6.79 (d, J=8.8 Hz, 2H), 4.66-4.55 (m, 2H), 4.31 (d, J=9.6 Hz, 1H), 4.01-3.94 (m, 4H), 3.87-3.84 (m, 1H), 3.68-3.58 (m, 2H), 3.45-3.37 (m, 3H), 3.2 (t, J=8.6 Hz, 2H), 1.36 (t, J=7.0 Hz, 3H); [M+Na]$^+$ 473.

Example 014

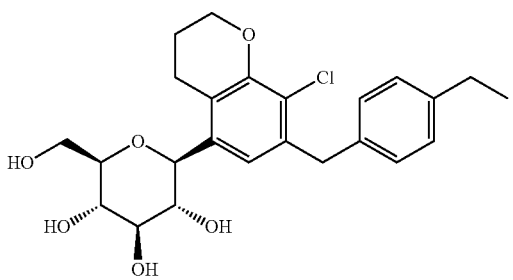

(2S,3R,4R,5S,6R)-2-(8-Chloro-7-(4-ethylbenzyl)chroman-5-yl)-6-(hydroxymethyl)tetrahydro-2H-pyran-3,4,5-triol (E014)

A suspension of 84 (170 mg, 0.21 mmol) and Pd/C (10 wt. %, 25.5 mg) in THF (2.0 mL) and MeOH (1.0 mL) was stirred at room temperature for 6 hours under atmosphere of H$_2$. The mixture was filtered through a Celite pad and concentrated in vacuo. The residue was purified by a prep HPLC to provide the product E014 (28 mg, 28%) as a white solid.

$^1$H NMR (400 MHz, CDCl$_3$) δ 7.07 (ABq, Δν$_{AB}$=7.4 Hz, J$_{AB}$=8.4 Hz, 2H), 6.98 (s, 1H), 4.38-4.36 (m, 1H), 4.22-4.18 (m, 2H), 4.02 (ABq, Δν$_{AB}$=7.2 Hz, J$_{AB}$=15.4 Hz, 2H), 3.86 (d, J=12.2 Hz, 1H), 3.65 (dd, J=12.2, 5.2 Hz, 1H), 3.52-3.45 (m, 2H), 3.41-3.34 (m, 2H), 3.03-2.82 (m, 2H), 2.58 (q, J=7.6 Hz, 2H), 2.00-1.98 (m, 2H), 1.19 (t, J=7.6 Hz, 3H); [M+Na]$^+$ 471.

Example 015

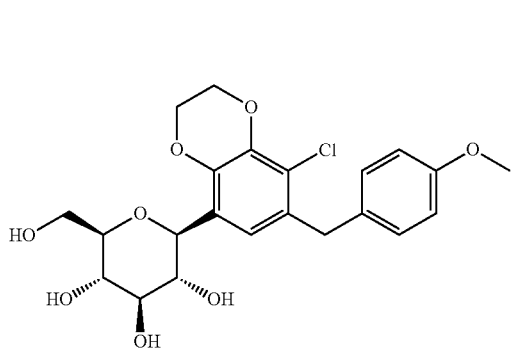

(2S,3R,4R,5S,6R)-2-(8-Chloro-7-(4-methoxybenzyl)-2,3-dihydrobenzo[b][1,4]dioxin-5-yl)-6-(hydroxymethyl)tetrahydro-2H-pyran-3,4,5-triol (E015)

$^1$H NMR (400 MHz, CD$_3$OD) δ 7.09 (d, J=8.8 Hz, 2H), 6.95 (s, 1H), 6.80 (d, J=8.7 Hz, 2H), 4.88 (s, 4H), 4.63-4.55 (m, 1H), 4.37-4.33 (m, 2H), 4.31-4.25 (m, 2H), 3.96 (ABq, Δν$_{AB}$=13.3 Hz, J$_{AB}$=15.2 Hz, 2H), 3.87 (d, J=11.0 Hz, 1H), 3.77 (s, 3H), 3.73-3.64 (m, 1H), 3.52-3.45 (m, 2H), 3.41-3.35 (m, 2H); [M+Na]$^+$ 475.

Example 016

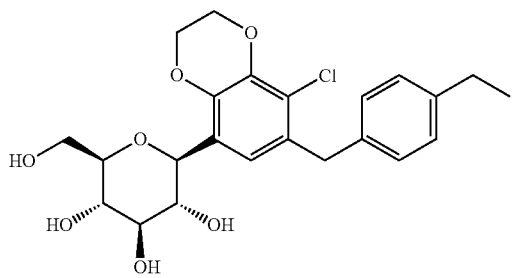

(2S,3R,4R,5S,6R)-2-(8-Chloro-7-(4-ethylbenzyl)-2,3-dihydrobenzo[b][1,4]dioxin-5-yl)-6-(hydroxymethyl)tetrahydro-2H-pyran-3,4,5-triol (E016)

$^1$H NMR (400 MHz, CD$_3$OD) δ 7.10 (s, 4H), 4.86 (s, 5H), 4.62-4.54 (m, 1H), 4.37-4.32 (m, 2H), 4.31-4.25 (m, 2H), 4.01 (ABq, Δν$_{AB}$=11.8 Hz, J$_{AB}$=15.1 Hz, 2H), 3.88 (d, J=10.5 Hz, 1H), 3.73-3.63 (m, 1H), 3.54-3.44 (m, 2H), 3.41-3.36 (m, 2H), 2.61 (q, J=7.6 Hz, 2H), 1.22 (t, J=7.6 Hz, 3H); [M+Na]$^+$ 473.

Example 017

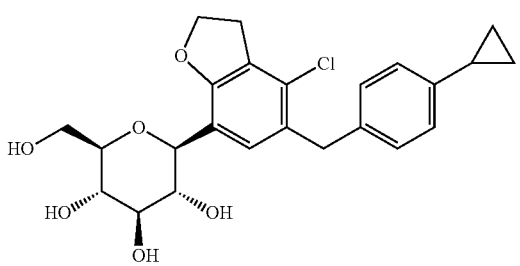 [SMILES: OC[C@H]1O[C@@H](c2cc(Cc3ccc(C4CC4)cc3)c(Cl)c3c2OCC3)[C@H](O)[C@@H](O)[C@@H]1O]

(2S,3R,4R,5S,6R)-2-(4-Chloro-5-(4-cyclopropylbenzyl)-2,3-dihydrobenzofuran-7-yl)-6-(hydroxymethyl)tetrahydro-2H-pyran-3,4,5-triol (E017)

$^1$H NMR (400 MHz, CD$_3$OD) δ 7.11 (s, 1H), 7.04 (d, J=8.0 Hz, 2H), 6.94 (d, J=8.0 Hz, 2H), 4.64-4.57 (m, 2H), 4.29 (d, J=9.6 Hz, 1H), 3.96 (ABq, Δν$_{AB}$=10.4 Hz, J$_{AB}$=15.4 Hz, 2H), 3.86-3.83 (m, 1H), 3.67-3.63 (m, 1H), 3.60 (t, J=8.8 Hz, 1H), 3.45-3.41 (m, 1H), 3.39-3.35 (m, 2H), 3.22 (t, J=8.8 Hz, 2H), 1.87-1.81 (m, 1H), 0.92-0.87 (m, 2H), 0.63-0.59 (m, 2H); [M+Na]$^+$ 469.

Example 018

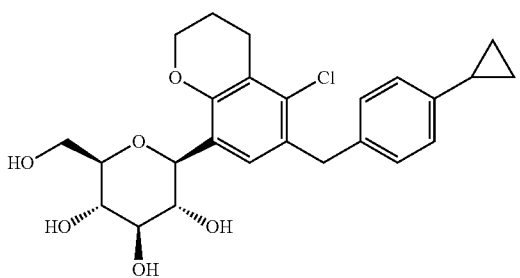 [SMILES: OC[C@H]1O[C@@H](c2cc(Cc3ccc(C4CC4)cc3)c(Cl)c3c2OCCC3)[C@H](O)[C@@H](O)[C@@H]1O]

(2S,3R,4R,5S,6R)-2-(5-Chloro-6-(4-cyclopropylbenzyl)chroman-8-yl)-6-(hydroxymethyl)tetrahydro-2H-pyran-3,4,5-triol (E018)

$^1$H NMR (400 MHz, CD$_3$OD) δ 7.19 (s, 1H), 7.04 (d, J=8.0 Hz, 2H), 6.94 (d, J=8.0 Hz, 2H), 4.63-4.60 (m, 1H), 4.18-4.08 (m, 2H), 3.96 (ABq, Δν$_{AB}$=13.6 Hz, J$_{AB}$=15.2 Hz, 2H), 3.86-3.83 (m, 1H), 3.67-3.63 (m, 1H), 3.48-3.43 (m, 2H), 3.39-3.35 (m, 2H), 2.78 (t, J=6.8 Hz, 2H), 2.04-1.98 (m, 2H), 1.87-1.80 (m, 1H), 0.92-0.87 (m, 2H), 0.63-0.58 (m, 2H); [M+Na]$^+$ 483.

Example 019

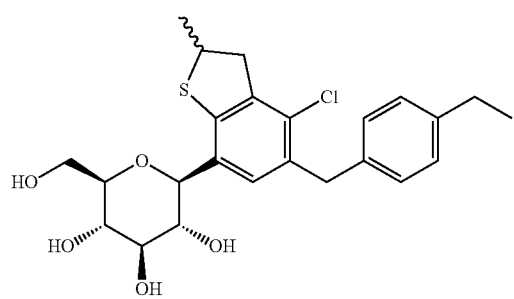 [SMILES: CCc1ccc(Cc2cc([C@@H]3O[C@H](CO)[C@@H](O)[C@H](O)[C@H]3O)c3c(c2Cl)CC(C)S3)cc1]

(2S,3R,4R,5S,6R)-2-(4-Chloro-5-(4-ethylbenzyl)-2-methyl-2,3-dihydrobenzo[b]thiophen-7-yl)-6-(hydroxymethyl)tetrahydro-2H-pyran-3,4,5-triol (E019)

$^1$H NMR (400 MHz, CD$_3$OD) 7.13 (s, 1H), 7.08-7.04 (m, 4H), 4.09 (dd, J=7.4, 2.2 Hz, 1H), 4.03-3.94 (m, 2H), 3.87-3.84 (m, 2H), 3.68-3.60 (m, 2H), 3.47-3.40 (m, 2H), 3.39-3.35 (m, 2H), 3.10-3.05 (m, 1H), 2.97-2.91 (m, 1H), 2.57 (q, J=7.6 Hz, 2H), 1.35 (d, J=6.8 Hz, 3H), 1.18 (t, J=7.6 Hz, 3H) 2:1 mixture; [M+Na]$^+$ 487.

Example 020

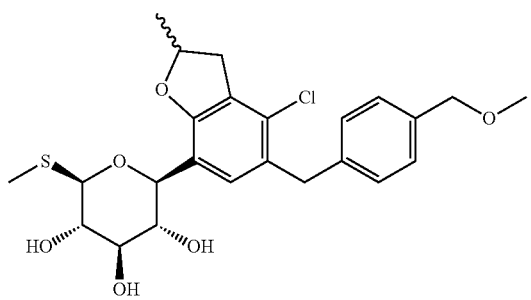

(2S,3R,4R,5S,6R)-2-(4-Chloro-5-(4-ethoxybenzyl)-2-methyl-2,3-dihydrobenzofuran-7-yl)-6-(methylthio)tetrahydro-2H-pyran-3,4,5-triol (E020)

$^1$H NMR (400 MHz, CDCl$_3$) 7.08 (d, J=8.4 Hz, 2H), 6.99 (s, 1H), 6.80 (d, J=8.4 Hz, 2H), 5.05-4.94 (m, 1H), 4.44-4.35 (m, 2H), 3.99 (q, J=7.0 Hz, 2H), 3.94-3.89 (m, 2H), 3.78-3.66 (m, 2H), 3.57-3.49 (m, 1H), 3.39-3.30 (m, 1H), 2.87-2.79 (m, 1H), 2.15 (d, J=3.2 Hz, 3H), 1.45 (d, J=7.4 Hz, 3H), 1.39 (t, J=7.0 Hz, 3H) 2:1 mixture; [M+Na]$^+$ 503.

Example 021

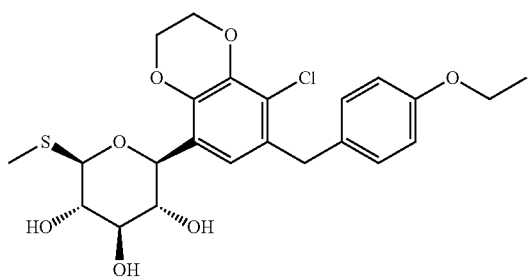 [SMILES: CCOc1ccc(Cc2cc([C@@H]3O[C@H](SC)[C@@H](O)[C@H](O)[C@H]3O)c3c(c2Cl)OCCO3)cc1]

(2S,3R,4R,5S,6R)-2-(8-Chloro-7-(4-ethoxybenzyl)-2,3-dihydrobenzo[b][1,4]dioxin-5-yl)-6-(methylthio)tetrahydro-2H-pyran-3,4,5-triol (E021)

$^1$H NMR (400 MHz, CDCl$_3$) 7.08 (d, J=8.4 Hz, 2H), 6.81 (s, 1H), 6.79 (d, J=2.4 Hz, 2H), 4.67 (d, J=9.6 Hz, 1H), 4.38-4.34 (m, 3H), 4.31-4.25 (m, 2H), 4.02-3.97 (m, 4H), 3.70-3.62 (m, 2H), 3.55-3.51 (m, 1H), 2.78 (br.s, 1H), 2.49 (br.s, 1H), 2.14 (s, 3H), 2.10 (br.s, 1H), 1.39 (t, J=7.0 Hz, 3H); [M+Na]$^+$ 505.

Example 022

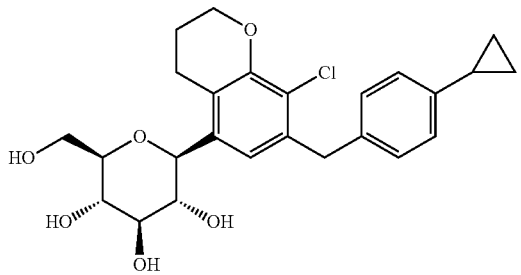

(2S,3R,4R,5S,6R)-2-(8-Chloro-7-(4-cyclopropylbenzyl)chroman-5-yl)-6-(hydroxymethyl)tetrahydro-2H-pyran-3,4,5-triol (E022)

$^1$H NMR (400 MHz, CD$_3$OD) δ 7.08 (d, J=8.2 Hz, 2H), 7.00 (s, 1H), 6.97 (d, J=8.2 Hz, 2H), 4.90 (s, 4H), 4.43-4.37 (m, 1H), 4.38-4.16 (m, 2H), 4.03 (ABq, Δν$_{AB}$=10.0 Hz, J$_{AB}$=15.0 Hz, 2H), 3.92-3.85 (m, 1H), 3.71-3.64 (m, 1H), 3.55-3.44 (m, 2H), 3.37-3.32 (m, 2H), 3.05-2.92 (m, 1H), 2.91-2.83 (m, 1H), 2.07-1.99 (m, 2H), 1.91-1.82 (m, 1H), 0.97-0.90 (m, 2H), 0.66-0.61 (m, 2H); [M+Na]$^+$ 483.

Example 023

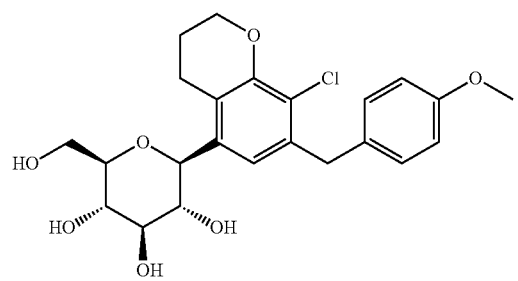

(2S,3R,4R,5S,6R)-2-(8-Chloro-7-(4-methoxybenzyl)chroman-5-yl)-6-(hydroxymethyl)tetrahydro-2H-pyran-3,4,5-triol (E023)

$^1$H NMR (400 MHz, CD$_3$OD) δ 7.12 (d, J=8.7 Hz, 2H), 7.00 (s, 1H), 6.81 (d, J=8.7 Hz, 2H), 4.91 (s, 4H), 4.42-4.36 (m, 1H), 4.25-4.19 (m, 2H), 4.01 (ABq, Δν$_{AB}$=10.0 Hz, J$_{AB}$=15.1 Hz, 2H), 3.91-3.85 (m, 1H), 3.77 (s, 3H), 3.71-3.63 (m, 1H), 3.55-3.33 (m, 4H), 3.05-2.97 (m, 1H), 2.93-2.84 (m, 1H), 2.05-1.99 (m, 2H); [M+Na]$^+$ 473.

Example 024

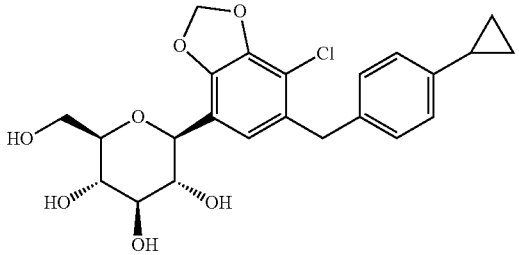

(2S,3R,4R,5S,6R)-2-(7-Chloro-6-(4-cyclopropylbenzyl)benzo[d][1,3]dioxol-4-yl)-6-(hydroxymethyl)tetrahydro-2H-pyran-3,4,5-triol (E024)

$^1$H NMR (400 MHz, CD$_3$OD) δ 7.07 (d, J=8.2 Hz, 2H), 6.98 (d, J=8.2 Hz, 2H), 6.88 (s, 1H), 6.06 (dd, J=7.0 Hz, 1.0 Hz, 2H), 4.85 (s, 4H), 4.28 (d, J=9.6 Hz, 1H), 3.98 (ABq, Δν$_{AB}$=10.9 Hz, J$_{AB}$=15.2 Hz, 2H), 3.88 (d, J=10.5 Hz, 1H), 3.72-3.63 (m, 1H), 3.60 (t, J=9.2 Hz, 1H), 3.49-3.33 (m, 3H), 1.93-1.81 (m, 1H), 0.97-0.89 (m, 2H), 0.68-0.60 (m, 2H); [M+Na]$^+$ 471.

Example 025

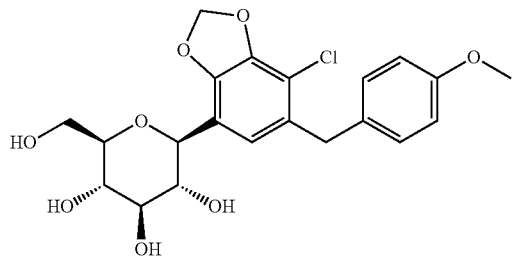

(2S,3R,4R,5S,6R)-2-(7-Chloro-6-(4-methoxybenzyl)benzo[d][1,3]dioxol-4-yl)-6-(hydroxymethyl)tetrahydro-2H-pyran-3,4,5-triol (E025)

$^1$H NMR (400 MHz, CD$_3$OD) δ 7.12 (d, J=8.8 Hz, 2H), 6.88 (s, 1H), 6.83 (d, J=8.8 Hz, 2H), 6.06 (dd, J=7.1 Hz, 1.1 Hz, 2H), 4.89 (s, 4H), 4.28 (d, J=9.6 Hz, 1H), 3.97 (ABq, Δν$_{AB}$=11.1 Hz, J$_{AB}$=15.2 Hz, 2H), 3.92-3.85 (m, 1H), 3.77 (s, 3H), 3.73-3.63 (m, 1H), 3.62-3.55 (m, 1H), 3.49-3.32 (m, 3H); [M+Na]$^+$ 461.

Example 026

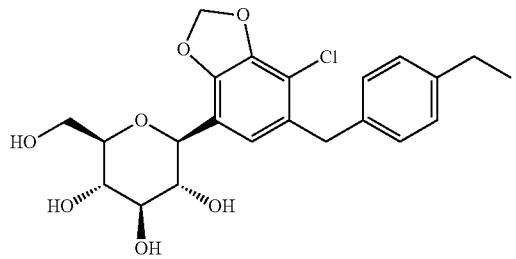

(2S,3R,4R,5S,6R)-2-(7-Chloro-6-(4-ethylbenzyl)benzo[d][1,3]dioxol-4-yl)-6-(hydroxymethyl)tetrahydro-2H-pyran-3,4,5-triol (E026)

$^1$H NMR (400 MHz, CD$_3$OD) δ 7.10 (s, 4H), 6.89 (s, 1H), 6.06 (dd, J=7.0 Hz, 1.1 Hz, 2H), 4.86 (s, 4H), 4.28 (d, J=9.6 Hz, 1H), 4.00 (ABq, Δv$_{AB}$=10.4 Hz, J$_{AB}$=15.2 Hz, 2H), 3.89 (dd, J=12.0 Hz, 1.6 Hz, 1H), 3.71-3.63 (m, 1H), 3.64-3.55 (m, 1H), 3.51-3.43 (m, 1H), 3.41-3.35 (m, 2H), 2.62 (q, J=7.6 Hz, 2H), 1.22 (t, J=7.6 Hz, 3H); [M+Na]$^+$ 459.

Example 027

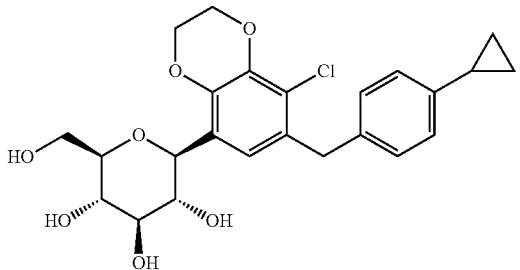

(2S,3R,4R,5S,6R)-2-(8-Chloro-7-(4-cyclopropylbenzyl)-2,3-dihydrobenzo[b][1,4]dioxin-5-yl)-6-(hydroxymethyl)tetrahydro-2H-pyran-3,4,5-triol (E027)

$^1$H NMR (400 MHz, CD$_3$OD) δ 7.07 (d, J=8.2 Hz, 2H), 6.97 (d, J=8.2 Hz, 2H), 6.95 (s, 1H), 4.86 (s, 4H), 4.63-4.54 (m, 1H), 4.36-4.31 (m, 2H), 4.30-4.22 (m, 2H), 3.99 (ABq, Δv$_{AB}$=13.4 Hz, J$_{AB}$=15.2 Hz, 2H), 3.88 (d, J=11.5 Hz, 1H), 3.72-3.63 (m, 1H), 3.53-3.43 (m, 2H), 3.40-3.35 (m, 2H), 1.90-1.82 (m, 1H), 0.96-0.89 (m, 2H), 0.66-0.59 (m, 2H); [M+Na]$^+$ 485.

Example 028

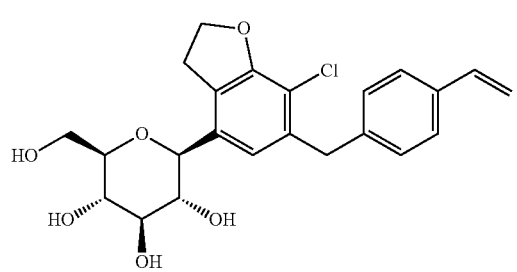

(2S,3R,4R,5S,6R)-2-(7-Chloro-6-(4-vinylbenzyl)-2,3-dihydrobenzofuran-4-yl)-6-(hydroxymethyl)tetrahydro-2H-pyran-3,4,5-triol (E028)

$^1$H NMR (400 MHz, CD$_3$OD) δ 7.34 (d, J=8.0 Hz, 2H), 7.18 (d, J=8.0 Hz, 2H), 6.90 (s, 1H), 6.72 (dd, J=17.6, 11.2 Hz, 1H), 5.74 (dd, J=17.6, 1.2 Hz, 1H), 5.19 (dd, J=10.8, 1.2 Hz, 1H), 4.66 (t, J=8.8 Hz, 2H), 4.18 (d, J=8.8 Hz, 1H), 4.07 (ABq, Δv$_{AB}$=17.4 Hz, J$_{AB}$=15.2 Hz, 2H), 3.91 (dd, J=11.6, 1.2 Hz, 1H), 3.73-3.69 (m, 1H), 3.53-3.44 (m, 3H), 3.41-3.31 (m, 3H), 1.45 (d, J=6.4 Hz, 1H); [M+Na]$^+$ 455.

Example 029

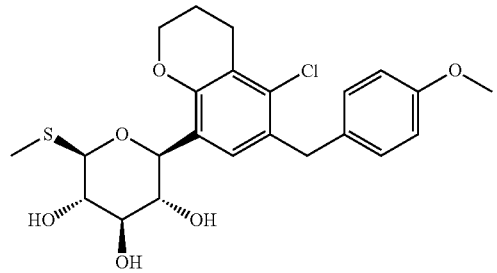

(2S,3R,4R,5S,6R)-2-(5-Chloro-6-(4-methoxybenzyl)chroman-8-yl)-6-(methylthio)tetrahydro-2H-pyran-3,4,5-triol (E029)

$^1$H NMR (400 MHz, CDCL$_3$) δ 7.09 (d, J=8.6 Hz, 2H), 7.07 (s, 1H), 6.81 (d, J=8.6 Hz, 2H), 4.72 (d, J=9.6 Hz, 1H), 4.23-4.18 (m, 1H), 4.13-4.08 (m, 1H), 3.99 (ABq, Δv$_{AB}$=10.5 Hz, J$_{AB}$=15.6 Hz, 2H), 3.78 (s, 3H), 3.71 (t, J=9.0 Hz, 1H), 3.592-3.513 (m, 2H), 3.49 (brs, 1H), 2.82-2.78 (m, 2H), 2.52 (brs, 1H), 2.31 (brs, 1H), 2.14 (s, 3H), 2.06-2.02 (m, 2H); [M+Na]$^+$ 489.

Example 030

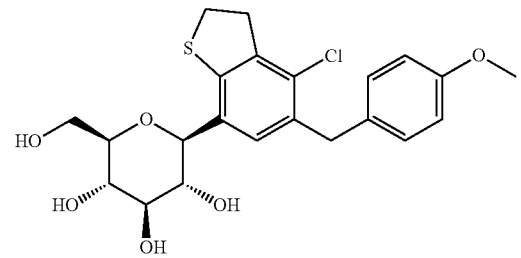

(2S,3R,4R,5S,6R)-2-(4-Chloro-5-(4-methoxybenzyl)-2,3-dihydrobenzo[b]thiophen-7-yl)-6-(hydroxymethyl)tetrahydro-2H-pyran-3,4,5-triol (E030)

$^1$H NMR (400 MHz, MeOD) δ 7.15 (s, 1H), 7.12 (d, J=8.4 Hz, 2H), 6.84 (d, J=8.4 Hz, 2H), 4.16 (d, J=9.2 Hz, 1H), 4.01 (ABq, Δv$_{AB}$=13.7 Hz, J$_{AB}$=17.2 Hz, 2H), 3.92-3.89 (m, 1H), 3.78 (s, 3H), 3.74-3.67 (m, 2H), 3.50-3.39 (m, 5H), 3.37-3.36 (m, 2H); [M+Na]$^+$ 475.

Example 031

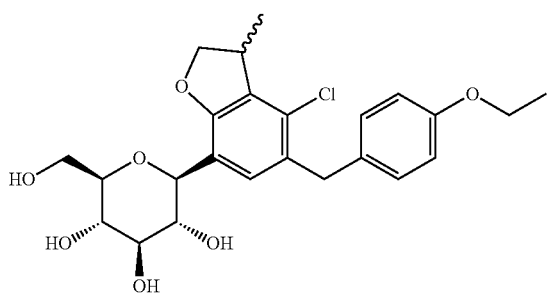 [SMILES: CCOc1ccc(Cc2cc([C@@H]3O[C@H](CO)[C@@H](O)[C@H](O)[C@H]3O)c3c(c2Cl)C(C)CO3)cc1]

(2S,3R,4R,5S,6R)-2-(4-Chloro-5-(4-ethoxybenzyl)-3-methyl-2,3-dihydrobenzofuran-7-yl)-6-(hydroxymethyl)-tetrahydro-2H-pyran-3,4,5-triol (E031)

$^1$H NMR (400 MHz, MeOD) δ 7.12 (d, J=4.0 Hz, 1H), 7.07 (d, J=8.4 Hz, 2H), 6.78 (dd, J=6.8, 2.0 Hz, 2H), 4.62 (dd, J=18.4, 8.8 Hz, 1H), 4.31 (ABq, Δν$_{AB}$=6.4 Hz, J$_{AB}$=9.6 Hz, 1H), 4.28-4.22 (m, 1H), 3.98 (q, J=7.2 Hz, 2H), 3.95 (d, J=4.0 Hz, 1H), 3.85 (dd, J=12.0, 1.6 Hz, 1H), 3.67-3.55 (m, 3H), 3.46-3.35 (m, 3H), 1.37-1.29 (m, 6H); [M+Na]$^+$ 487.

Example 032

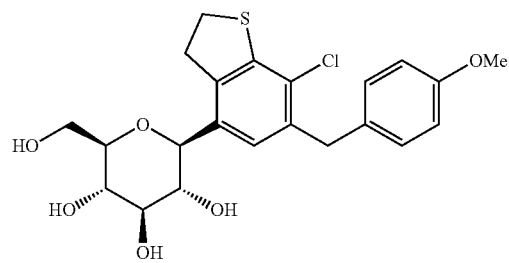

(2S,3R,4R,5S,6R)-2-(7-(Difluoromethyl)-6-(4-methoxybenzyl)-2,3-dihydro-1H-inden-4-yl)-6-(hydroxymethyl)tetrahydro-2H-pyran-3,4,5-triol (E032)

$^1$H NMR (400 MHz, CD$_3$OD) δ 7.21 (s, 1H), 7.07 (d, J=8.8 Hz, 2H), 6.88 (d, J=54.4 Hz, 1H), 6.84 (d, J=8.8 Hz, 2H), 4.33 (d, J=9.2 Hz, 1H), 4.11 (ABq, Δν$_{AB}$=12.7 Hz, J$_{AB}$=16.0 Hz, 2H), 3.92 (d, J=11.2 Hz, 1H), 3.79 (s, 3H), 3.74-3.69 (m, 1H), 3.56-3.49 (m, 2H), 3.46-3.41 (m, 2H), 3.16-3.08 (m, 3H), 3.03-2.95 (m, 1H), 2.17-2.07 (m, 2H); [M+Na]$^+$ 473.

Example 033

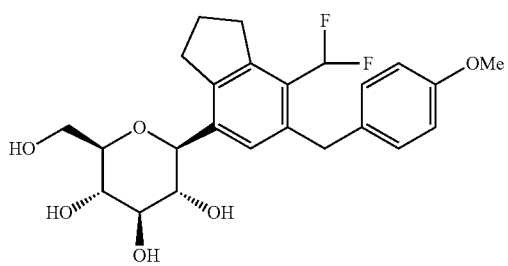 [SMILES: COc1ccc(Cc2cc([C@@H]3O[C@H](CO)[C@@H](O)[C@H](O)[C@H]3O)c3c(c2C(F)F)CCC3)cc1]

(2S,3R,4R,5S,6R)-2-(7-Chloro-6-(4-ethylbenzyl)-2,3-dihydro-1H-inden-4-yl)-6-(hydroxymethyl)tetrahydro-2H-pyran-3,4,5-triol (E033)

$^1$H NMR (400 MHz, CD$_3$OD) δ 7.21 (s, 1H), 7.11 (d, J=3.2 Hz, 4H), 4.26 (d, J=9.2 Hz, 1H), 4.06 (ABq, Δν$_{AB}$=15.9 Hz, J$_{AB}$=15.2 Hz, 2H), 3.90 (d, J=12.8 Hz, 1H), 3.73-3.67 (m, 1H), 3.53-3.46 (m, 2H), 3.43-3.39 (m, 2H), 3.21-3.15 (m, 1H), 3.11-3.02 (m, 1H), 2.98 (t, J=3.2 Hz, 2H), 2.62 (q, J=3.2 Hz, 2H), 2.16-2.07 (m, 2H), 1.23 (t, J=7.6 Hz, 3H).

Example 034

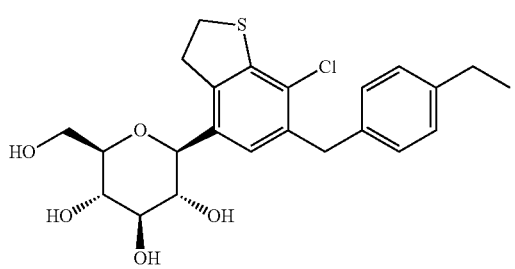

(2S,3R,4R,5S,6R)-2-(7-Chloro-6-(4-methoxybenzyl)-2,3-dihydrobenzo[b]thiophen-4-yl)-6-(hydroxymethyl)tetrahydro-2H-pyran-3,4,5-triol (E034)

$^1$H NMR (400 MHz, CD$_3$OD) δ 7.07 (d, J=8.8 Hz, 2H), 7.04 (s, 1H), 6.78 (d, J=8.4 Hz, 2H), 4.20 (d, J=8.8 Hz, 1H), 3.91 (ABq, Δν$_{AB}$=15.8 Hz, J$_{AB}$=15.0 Hz, 2H), 3.86 (d, J=11.2 Hz, 1H), 3.73 (s, 3H), 3.68-3.63 (m, 1H), 3.60-3.52 (m, 1H), 3.47-3.39 (m, 3H), 3.38-3.32 (m, 4H); [M+Na]$^+$ 475.

Example 035

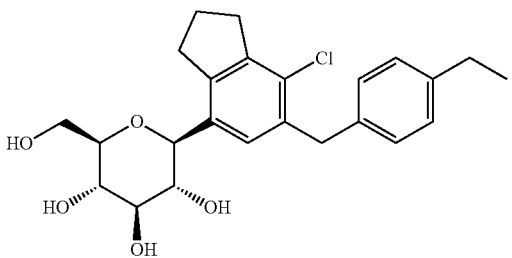

(2S,3R,4R,5S,6R)-2-(7-Chloro-6-(4-ethylbenzyl)-2,3-dihydrobenzo[b]thiophen-4-yl)-6-(hydroxymethyl)tetrahydro-2H-pyran-3,4,5-triol (E035)

$^1$H NMR (400 MHz, MeOD) δ 7.11 (s, 4H), 7.10 (s, 1H), 4.25 (d, J=9.2 Hz, 1H), 4.57 (d, J=9.6 Hz, 1H), 4.03 (ABq, Δν$_{AB}$=15.3 Hz, J$_{AB}$=15.0 Hz, 2H), 3.92-3.89 (m, 1H), 3.72-3.68 (m, 1H), 3.65-3.57 (m, 1H), 3.51-3.45 (m, 2H), 3.44-3.37 (m, 3H), 2.62 (q, J=7.6 Hz, 2H), 1.23 (t, J=7.6 Hz, 3H); [M+Na]$^+$ 473.

Example 036

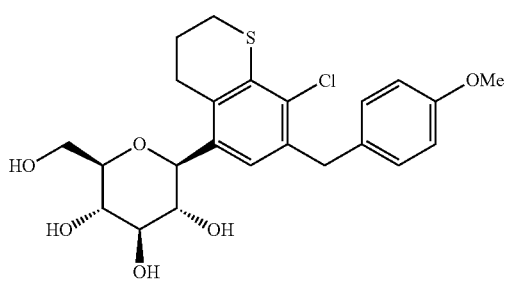

(2S,3R,4R,5S,6R)-2-(8-Chloro-7-(4-methoxybenzyl)thiochroman-5-yl)-6-(hydroxymethyl)tetrahydro-2H-pyran-3,4,5-triol (E036)

$^1$H NMR (400 MHz, CD$_3$OD) δ 7.15 (s, 1H), 7.07 (d, J=8.8 Hz, 2H), 6.79 (d, J=8.8 Hz, 2H), 4.48 (d, J=8.8 Hz, 1H), 3.98 (ABq, Δν$_{AB}$=9.6 Hz, J$_{AB}$=15.0 Hz, 2H), 3.86 (d, J=12.0 Hz, 1H), 3.74 (s, 3H), 3.67-3.62 (m, 1H), 3.51-3.44 (m, 2H), 3.41-3.36 (m, 2H), 3.07-2.96 (m, 3H), 2.94-2.86 (m, 1H), 2.12-2.06 (m, 2H); [M+Na]$^+$=489.

Example 037

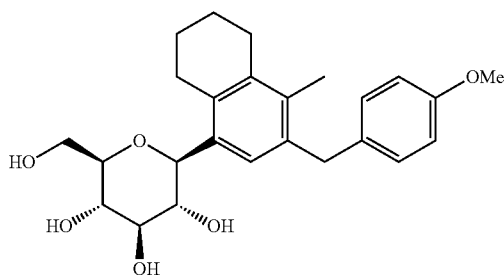 [SMILES: COc1ccc(Cc2cc([C@@H]3O[C@H](CO)[C@@H](O)[C@H](O)[C@H]3O)c3c(c2C)CCCC3)cc1]

(2R,3S,4R,5R,6S)-2-(Hydroxymethyl)-6-(3-(4-methoxybenzyl)-4-methyl-5,6,7,8-tetrahydronaphthalen-1-yl)tetrahydro-2H-pyran-3,4,5-triol (E037)

$^1$H NMR (400 MHz, CD$_3$OD) δ 7.20 (s, 1H), 7.05 (d, J=8.8 Hz, 2H), 6.82 (d, J=8.8 Hz, 2H), 4.53 (d, J=9.6 Hz, 1H), 3.98 (s, 2H), 3.91 (d, J=11.6 Hz, 1H), 3.78 (s, 3H), 3.72-3.67 (m, 1H), 3.66 (t, J=9.2 Hz, 1H), 3.57-3.52 (m, 1H), 3.46-3.42 (m, 2H), 3.03-2.85 (m, 2H), 2.69 (t, J=5.8 Hz, 2H), 2.07 (s, 3H), 1.88-1.77 (m, 4H); [M+Na]$^+$=451.

Example 038

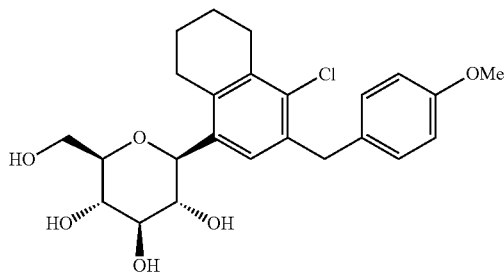

(2S,3R,4R,5S,6R)-2-(4-Chloro-3-(4-methoxybenzyl)-5,6,7,8-tetrahydronaphthalen-1-yl)-6-(hydroxymethyl)tetrahydro-2H-pyran-3,4,5-triol (E038)

$^1$H NMR (400 MHz, CD$_3$OD) δ 7.29 (s, 1H), 7.13 (d, J=8.8 Hz, 2H), 6.84 (d, J=8.8 Hz, 2H), 4.51 (d, J=9.2 Hz, 1H), (ABq, Δν$_{AB}$=8.1 Hz, J$_{AB}$=15.6 Hz, 2H), 3.90 (d, J=12.0 Hz, 1H), 3.79 (s, 3H), 3.72-3.67 (m, 1H), 3.58-3.51 (m, 2H), 3.46-3.41 (m, 2H), 3.04-2.86 (m, 2H), 2.83 (t, J=6.0 Hz, 2H), 1.88-1.77 (m, 4H); [M+Na]$^+$=471.

Example 039

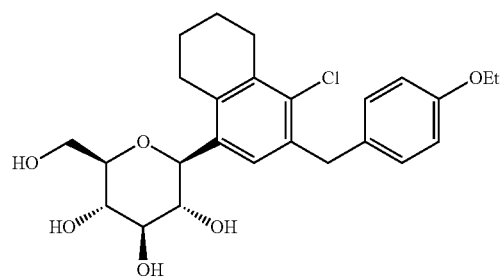 [SMILES: CCOc1ccc(Cc2cc([C@@H]3O[C@H](CO)[C@@H](O)[C@H](O)[C@H]3O)c3c(c2Cl)CCCC3)cc1]

(2S,3R,4R,5S,6R)-2-(4-Chloro-3-(4-ethoxybenzyl)-5,6,7,8-tetrahydronaphthalen-1-yl)-6-(hydroxymethyl)tetrahydro-2H-pyran-3,4,5-triol (E039)

$^1$H NMR (400 MHz, CD$_3$OD) δ 7.29 (s, 1H), 7.12 (d, J=8.8 Hz, 2H), 6.82 (d, J=8.4 Hz, 2H), 4.51 (d, J=9.2 Hz, 1H), 4.06 (ABq, Δν$_{AB}$=8.9 Hz, J$_{AB}$=15.4 Hz, 2H), 4.03 (q, J=7.2 Hz, 2H), 3.90 (d, J=12.0 Hz, 1H), 3.72-3.67 (m, 1H), 3.58-3.51 (m, 2H), 3.46-3.41 (m, 2H), 3.04-2.96 (m, 1H), 2.92-2.86 (m, 1H), 2.83 (t, J=5.8 Hz, 2H), 1.88-1.77 (m, 4H), 1.40 (t, J=7.0 Hz, 3H); [M+Na]$^+$=485.

Example 040

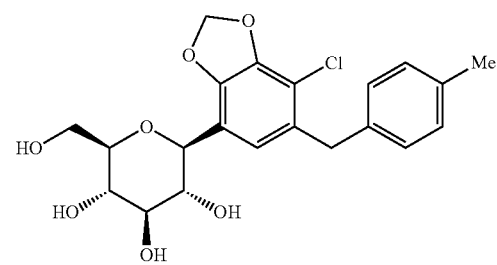 [SMILES: Cc1ccc(Cc2cc([C@@H]3O[C@H](CO)[C@@H](O)[C@H](O)[C@H]3O)c3c(c2Cl)OCO3)cc1]

(2S,3R,4R,5S,6R)-2-(7-Chloro-6-(4-methylbenzyl)benzo[d][1,3]dioxol-4-yl)-6-(hydroxymethyl)tetrahydro-2H-pyran-3,4,5-triol (E040)

$^1$H NMR (400 MHz, CD$_3$OD) δ 7.08 (s, 4H), 6.88 (s, 1H), 6.05 (dd, J=7.8 Hz, 0.96 Hz, 2H), 4.85 (s, 4H), 4.28 (d, J=9.6 Hz, 1H), 3.99 (ABq, Δν$_{AB}$=10.9 Hz, J$_{AB}$=15.3 Hz, 2H), 3.80 (d, J=11.9 Hz, 1H), 3.77-3.58 (m, 2H), 3.51-3.39 (m, 3H), 2.30 (s, 3H); [M+Na]$^+$ 445.

Example 041

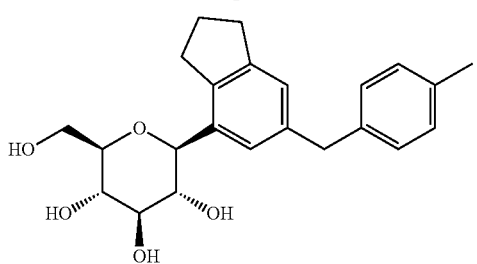 [SMILES: Cc1ccc(Cc2cc3c(c([C@@H]4O[C@H](CO)[C@@H](O)[C@H](O)[C@H]4O)c2)CCC3)cc1]

(2R,3S,4R,5R,6S)-2-(Hydroxymethyl)-6-(6-(4-methylbenzyl)-2,3-dihydro-1H-inden-4-yl)tetrahydro-2H-pyran-3,4,5-triol (E041)

$^1$H NMR (400 MHz, CD$_3$OD) 7.08 (s, 1H), 7.06-7.04 (m, 4H), 6.95 (s, 1H), 4.13 (d, J=8.8 Hz, 1H), 3.88-3.85 (m, 3H), 3.68-3.64 (m, 1H), 3.54-3.44 (m, 2H), 3.38-3.31 (m, 2H), 3.06-2.99 (m, 1H), 2.94-2.87 (m, 1H), 2.83 (t, J=7.2 Hz, 2H), 2.27 (s, 3H), 2.06-1.99 (m, 2H); [M+H]$^+$=385.

Example 042

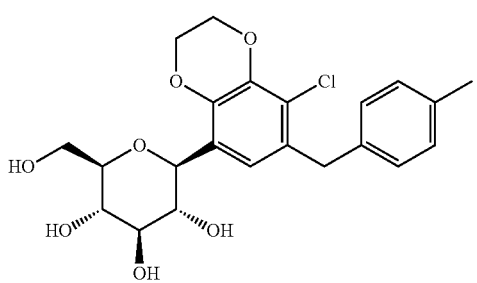 [SMILES: Cc1ccc(Cc2cc([C@@H]3O[C@H](CO)[C@@H](O)[C@H](O)[C@H]3O)c3c(c2Cl)OCCO3)cc1]

(2S,3R,4R,5S,6R)-2-(8-chloro-7-(4-methylbenzyl)-2,3-dihydrobenzo[b][1,4]dioxin-5-yl)-6-(hydroxymethyl)tetrahydro-2H-pyran-3,4,5-triol (E042)

$^1$H NMR (400 MHz, CD$_3$OD) 7.06-7.02 (m, 4H), 6.92 (s, 1H), 4.57-4.55 (m, 1H), 4.33-4.30 (m, 2H), 4.27-4.24 (m, 2H), 3.97 (ABq, Δν$_{AB}$=12.4 Hz, J$_{AB}$=15.2 Hz, 2H), 3.86-3.83 (m, 1H), 3.67-3.62 (m, 1H), 3.47-3.35 (m, 2H), 3.36-3.33 (m, 2H), 2.27 (s, 3H); [M+Na]$^+$=459.

Example 043

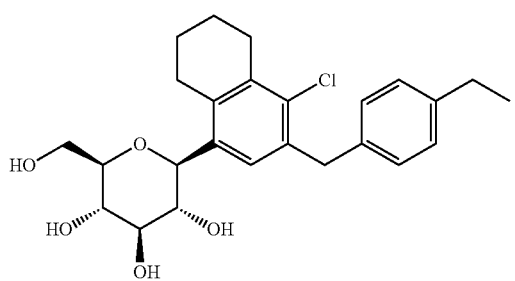

(2S,3R,4R,5S,6R)-2-(4-Chloro-3-(4-ethylbenzyl)-5,6,7,8-tetrahydronaphthalen-1-yl)-6-(hydroxymethyl)tetrahydro-2H-pyran-3,4,5-triol (E043)

$^1$H NMR (400 MHz, CD$_3$OD) δ 7.30 (s, 1H), 7.13-7.08 (m, 4H), 4.51 (d, J=9.2 Hz, 1H), 4.13-4.05 (m, 2H), 3.89 (d, J=11.2 Hz, 1H), 3.71-3.66 (m, 1H), 3.57-3.50 (m, 2H), 3.46-3.40 (m, 2H), 3.04-2.97 (m, 1H), 2.91-2.85 (m, 1H), 2.83 (t, J=6.0 Hz, 2H), 2.62 (q, J=7.6 Hz, 2H), 1.87-1.77 (m, 4H), 1.23 (t, J=7.6 Hz, 3H); [M+Na]$^+$=469.

Example 044

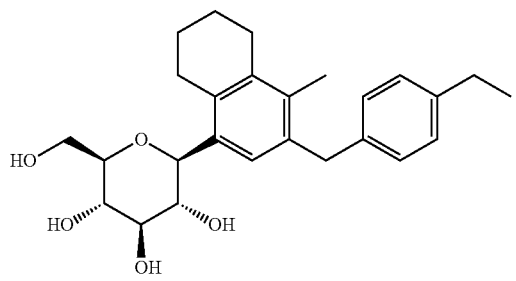 [SMILES: CCc1ccc(Cc2cc([C@@H]3O[C@H](CO)[C@@H](O)[C@H](O)[C@H]3O)c3c(c2C)CCCC3)cc1]

(2S,3R,4R,5S,6R)-2-(3-(4-Ethylbenzyl)-4-methyl-5,6,7,8-tetrahydronaphthalen-1-yl)-6-(hydroxymethyl)tetrahydro-2H-pyran-3,4,5-triol (E044)

$^1$H NMR (400 MHz, CD$_3$OD) δ 7.20 (s, 1H), 7.09-7.02 (m, 4H), 4.52 (d, J=9.6 Hz, 1H), 4.00 (s, 2H), 3.90 (d, J=12.0 Hz, 1H), 3.71-3.66 (m, 1H), 3.64 (t, J=9.0 Hz, 1H), 3.56-3.51 (m, 1H), 3.46-3.41 (m, 2H), 3.02-2.95 (m, 1H), 2.92-2.86 (m, 1H), 2.67 (t, J=5.6 Hz, 2H), 2.60 (q, J=7.6 Hz, 2H), 2.06 (s, 3H), 1.83-1.75 (m, 4H), 1.22 (t, J=7.6 Hz, 3H); [M+Na]$^+$=449.

Example 045

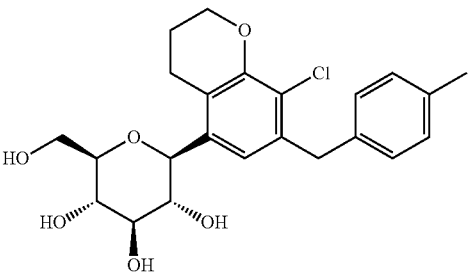 [SMILES: Cc1ccc(Cc2cc([C@@H]3O[C@H](CO)[C@@H](O)[C@H](O)[C@H]3O)c3c(c2Cl)OCCC3)cc1]

(2S,3R,4R,5S,6R)-2-(8-Chloro-7-(4-methylbenzyl)chroman-5-yl)-6-(hydroxymethyl)tetrahydro-2H-pyran-3,4,5-triol (E045)

$^1$H NMR (400 MHz, CD$_3$OD) 7.06-7.01 (m, 4H), 6.96 (s, 1H), 4.38-4.35 (m, 1H), 4.21-4.18 (m, 2H), 4.00 (ABq, Δν$_{AB}$=8.9 Hz, J$_{AB}$=15.2 Hz, 2H), 3.87-3.84 (m, 1H), 3.66-3.62 (m, 1H), 3.51-3.45 (m, 2H), 3.37-3.34 (m, 2H), 3.02-2.95 (m, 1H), 2.89-2.81 (m, 1H), 2.26 (s, 3H), 2.00-1.98 (m, 2H); [M+Na]$^+$ 457.

Example 046

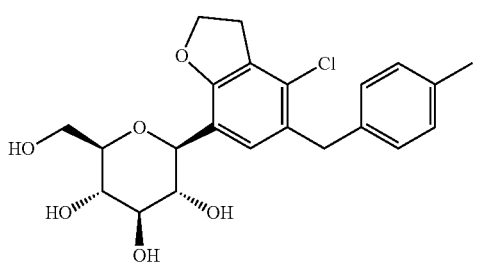 [SMILES: Cc1ccc(Cc2cc([C@@H]3O[C@H](CO)[C@@H](O)[C@H](O)[C@H]3O)c3c(c2Cl)CCO3)cc1]

(2S,3R,4R,5S,6R)-2-(4-Chloro-5-(4-methylbenzyl)-2,3-dihydrobenzofuran-7-yl)-6-(hydroxymethyl)tetrahydro-2H-pyran-3,4,5-triol (E046)

$^1$H NMR (400 MHz, CD$_3$OD) δ 7.16 (s, 1H), 7.10 (s, 4H), 4.66 (sext, J=8.64 Hz, 2H), 4.35 (d, J=9.64 Hz, 1H), 4.02 (q$_{AB}$, J$_{AB}$=15.26, 10.6 Hz, 2H), 3.90 (d, J=10.7 Hz, 1H), 3.72-3.68 (m, 1H), 3.64 (t, J=9.16 Hz, 1H), 3.50-3.26 (m, 3H), 3.28 (t, J=8.7 Hz, 2H), 2.32 (s, 3H); M+Na$^+$ 443

Example 047

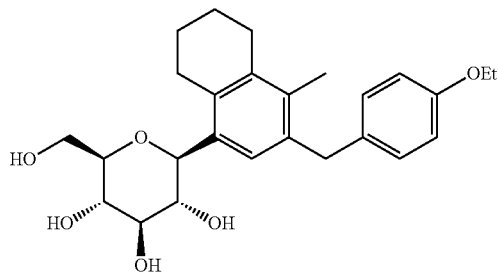 [SMILES: CCOc1ccc(Cc2cc([C@@H]3O[C@H](CO)[C@@H](O)[C@H](O)[C@H]3O)c3c(c2C)CCCC3)cc1]

(2S,3R,4R,5S,6R)-2-(3-(4-Ethoxybenzyl)-4-methyl-5,6,7,8-tetrahydronaphthalen-1-yl)-6-(hydroxymethyl)tetrahydro-2H-pyran-3,4,5-triol (E047)

$^1$H NMR (400 MHz, CD$_3$OD) δ 7.19 (s, 1H), 7.03 (d, J=8.8 Hz, 2H), 6.80 (d, J=8.8 Hz, 2H), 4.52 (d, J=9.6 Hz, 1H), 4.03 (q, J=6.5 Hz, 2H), 3.97 (s, 2H), 3.90 (d, J=12.0 Hz, 1H), 3.71-3.66 (m, 1H), 3.65 (t, J=9.2 Hz, 1H), 3.58-3.51 (m, 1H), 3.46-3.41 (m, 2H), 3.02-2.95 (m, 1H), 2.92-2.86 (m, 1H), 2.68 (t, J=5.6 Hz, 2H), 2.06 (s, 3H), 1.87-1.75 (m, 4H), 1.38 (t, J=7.0 Hz, 3H); [M+Na]$^+$=465.

Example 048

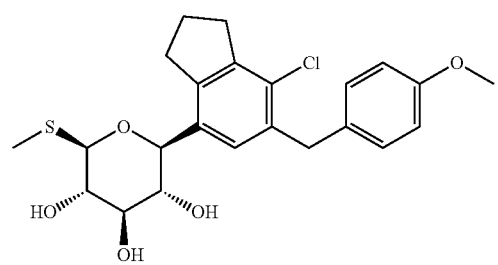

(2S,3R,4R,5S,6R)-2-(7-Chloro-6-(4-methoxybenzyl)-2,3-dihydro-1H-inden-4-yl)-6-(methylthio)tetrahydro-2H-pyran-3,4,5-triol (E048)

$^1$H NMR (400 MHz, DMSO-d$_6$) δ 7.11-7.09 (m, 3H), 6.83 (d, J=8.8 Hz, 2H), 5.19 (d, J=5.6 Hz, 1H), 5.10 (d, J=4.8 Hz, 1H), 4.88 (d, J=5.2 Hz, 1H), 4.33 (d, J=9.2 Hz, 1H), 4.17 (d, J=8.8 Hz, 1H), 3.96 (s, 2H), 3.70 (s, 3H), 3.31-3.24 (m, 2H), 3.21-3.14 (m, 1H), 3.07-2.92 (m, 2H), 2.90-2.86 (m, 2H), 2.05-1.97 (m, 5H); [M+Na]$^+$ 473.

Example 049

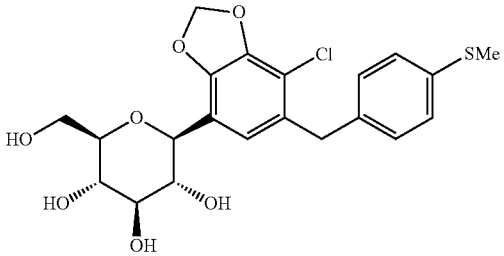 [SMILES: CSc1ccc(Cc2cc([C@@H]3O[C@H](CO)[C@@H](O)[C@H](O)[C@H]3O)c3c(c2Cl)OCO3)cc1]

(2S,3R,4R,5S,6R)-2-(7-Chloro-6-(4-(methylthio)benzyl)benzo[d][1,3]dioxol-4-yl)-6-(hydroxymethyl)tetrahydro-2H-pyran-3,4,5-triol (E049)

$^1$H NMR (400 MHz, CD$_3$OD) δ 7.20 (d, J=8.4 Hz, 2H), 7.14 (d, J=8.4 Hz, 2H), 6.90 (s, 1H), 6.06 (dd, J=7.8 Hz, 0.96 Hz, 2H), 4.84 (s, 4H), 4.29 (d, J=9.6 Hz, 1H), 4.00 (ABq, Δv$_{AB}$=10.2 Hz, J$_{AB}$=15.4 Hz, 2H), 3.89 (d, J=11.9 Hz, 1H), 3.73-3.64 (m, 1H), 3.60 (t, J=9.2 Hz, 1H), 3.52-3.38 (m, 3H), 2.46 (s, 3H); [M+Na]$^+$ 477.

Example 050

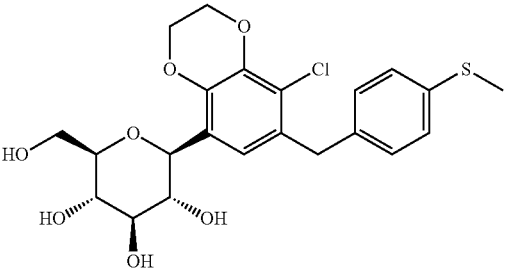 [SMILES: CSc1ccc(Cc2cc([C@@H]3O[C@H](CO)[C@@H](O)[C@H](O)[C@H]3O)c3c(c2Cl)OCCO3)cc1]

(2S,3R,4R,5S,6R)-2-(8-Chloro-7-(4-(methylthio)benzyl)-2,3-dihydrobenzo[b][1,4]dioxin-5-yl)-6-(hydroxymethyl)tetrahydro-2H-pyran-3,4,5-triol (E050)

$^1$H NMR (400 MHz, MeOD) δ 7.16 (d, J=8.4 Hz, 2H), 7.11 (d, J=8.4 Hz, 2H), 6.95 (s, 1H), 4.57 (d, J=9.6 Hz, 1H), 4.33-4.30 (m, 2H), 4.28-4.22 (m, 2H), 3.98 (ABq, Δv$_{AB}$=12.4 Hz, J$_{AB}$=15.2 Hz, 2H), 3.85 (d, J=11.2 Hz, 1H), 3.68-3.63 (m, 1H), 3.48-3.54 (m, 2H), 3.38-3.36 (m, 2H), 2.43 (s, 3H); [M+Na]$^+$ 491.

Example 051

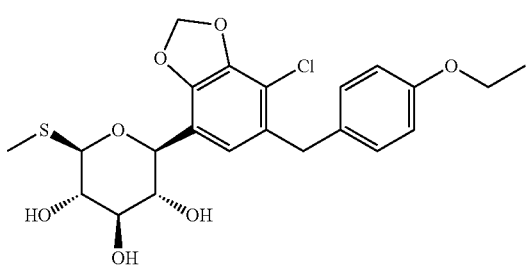 [SMILES: CCOc1ccc(Cc2cc([C@@H]3O[C@H](SC)[C@@H](O)[C@H](O)[C@H]3O)c3c(c2Cl)OCO3)cc1]

(2S,3R,4R,5S,6R)-2-(7-Chloro-6-(4-ethoxybenzyl)benzo[d][1,3]dioxol-4-yl)-6-(methylthio)tetrahydro-2H-pyran-3,4,5-triol (E051)

$^1$H NMR (400 MHz, CD$_3$OD) δ 7.13 (d, J=8.56 Hz, 2H), 6.85 (d, J=8.68 Hz, 2H), 6.81 (s, 1H), 6.09 (d, J=4.4 Hz, 2H), 4.40 (d, J=9.56 Hz, 1H), 4.33 (d, J=9.72 Hz, 1H), 4.04 (q, J=6.99 Hz, 2H), 3.99 (s, 2H), 3.65 (t, J=9.34 Hz, 1H), 3.48 (t, J=8.84 Hz, 1H), 3.40 (d, J=9.4 Hz, 1H), 2.17 (s, 2H), 1.40 (t, J=6.98 Hz, 3H); M+Na$^+$ 491

Example 052

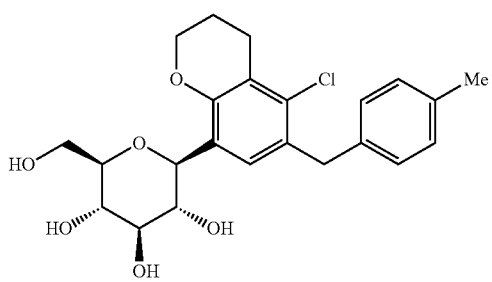 [SMILES: Cc1ccc(Cc2cc([C@@H]3O[C@H](CO)[C@@H](O)[C@H](O)[C@H]3O)c3c(c2Cl)CCCO3)cc1]

(2S,3R,4R,5S,6R)-2-(5-Chloro-6-(4-methylbenzyl)chroman-8-yl)-6-(hydroxymethyl)tetrahydro-2H-pyran-3,4,5-triol (E052)

$^1$H NMR (400 MHz, CD$_3$OD) δ 7.22 (s, 1H), 7.07 (s, 4H), 4.87 (s, 4H), 4.66-4.62 (m, 1H), 4.23-4.10 (m, 2H), 4.02 (ABq, Δν$_{AB}$=12.9 Hz, J$_{AB}$=15.2 Hz, 2H), 3.87 (d, J=12.1 Hz, 1H), 3.72-3.63 (m, 1H), 3.53-3.39 (m, 2H), 3.38-3.31 (m, 2H), 2.82 (t, J=6.6 Hz, 2H), 2.30 (s, 3H), 2.07-1.99 (m, 2H); [M+Na]$^+$ 457.

Example 053

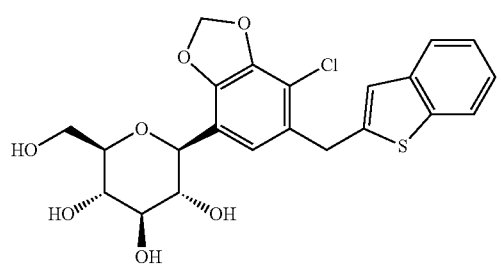

(2S,3R,4R,5S,6R)-2-(6-(Benzo[b]thiophen-2-ylmethyl)-7-chlorobenzo[d][1,3]dioxol-4-yl)-6-(hydroxymethyl)tetrahydro-2H-pyran-3,4,5-triol (E053)

$^1$H NMR (400 MHz, CD$_3$OD) δ 7.72 (d, J=7.6 Hz, 1H), 7.64 (d, J=7.2 Hz, 1H), 7.29-7.20 (m, 2H), 7.02 (s, 1H), 7.01 (s, 1H), 6.06 (dd, J=6.8, 0.8 Hz, 2H), 4.31-4.22 (m, 3H), 3.87-3.84 (m 1H), 3.68-3.63 (m, 1H), 3.60-3.55 (m, 1H), 3.46-3.42 (m, 1H), 3.40-3.34 (m, 2H); [M+Na]$^+$ 487.

Example 054

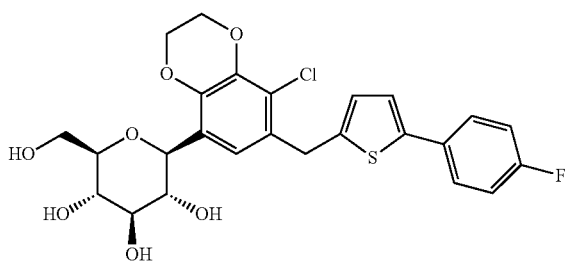

(2S,3R,4R,5S,6R)-2-(8-Chloro-7-((5-(4-fluorophenyl)thiophen-2-yl)methyl)-2,3-dihydrobenzo[b][1,4]dioxin-5-yl)-6-(hydroxymethyl)tetrahydro-2H-pyran-3,4,5-triol (E054)

$^1$H NMR (400 MHz, CD$_3$OD) 7.56-7.52 (m, 2H), 7.10-7.05 (m, 4H), 6.77 (d, J=3.6 Hz, 1H), 4.59-4.57 (m, 1H), 4.35-4.32 (m, 2H), 4.29-4.24 (m, 2H), 4.20-4.15 (m, 2H), 3.86-3.84 (m, 1H), 3.68-3.64 (m, 1H), 3.49-3.46 (m, 2H), 3.38-3.36 (m, 2H); [M+Na]$^+$ 545.

Example 055

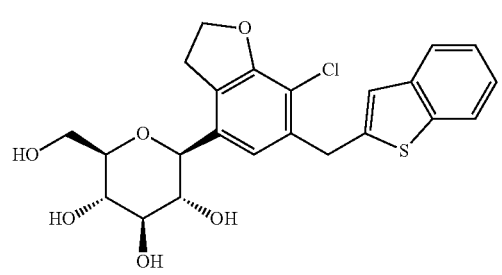

(2S,3R,4R,5S,6R)-2-(6-(Benzo[b]thiophen-2-ylmethyl)-7-chloro-2,3-dihydrobenzofuran-4-yl)-6-(hydroxymethyl)tetrahydro-2H-pyran-3,4,5-triol (E055)

$^1$H NMR (400 MHz, CD$_3$OD) 7.72 (d, J=7.6 Hz, 1H), 7.63 (d, J=7.2 Hz, 1H), 7.29-7.20 (m, 2H), 7.00-6.99 (m, 2H), 4.64 (t, J=8.8 Hz, 2H), 4.30 (ABq, Δν$_{AB}$=17.7 Hz, J$_{AB}$=15.6 Hz, 2H), 4.18-4.15 (m, 1H), 3.89-3.86 (m, 1H), 3.69-3.65 (m, 1H), 3.49-3.43 (m, 3H), 3.40-3.35 (m, 3H); [M+Na]$^+$ 485.

Example 056

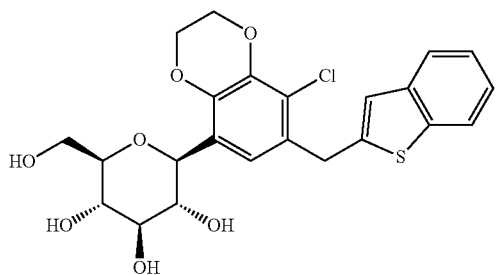 [SMILES: OC[C@H]1O[C@@H](c2cc(Cc3cc4ccccc4s3)c(Cl)c3c2OCCO3)[C@H](O)[C@@H](O)[C@@H]1O]

(2S,3R,4R,5S,6R)-2-(7-(Benzo[b]thiophen-2-ylmethyl)-8-chloro-2,3-dihydrobenzo[b][1,4]dioxin-5-yl)-6-(hydroxymethyl)tetrahydro-2H-pyran-3,4,5-triol (E056)

$^1$H NMR (400 MHz, CD$_3$OD) δ 7.72 (d, J=7.6 Hz, 1H), 7.63 (d, J=7.2 Hz, 1H), 7.29-7.20 (m, 2H), 7.08 (s, 1H), 6.99 (s, 1H), 4.60-4.57 (m, 1H), 4.35-4.31 (m, 2H), 4.29-4.23 (m, 4H), 3.86-3.83 (m, 1H), 3.68-3.63 (m, 1H), 3.51-3.43 (m, 2H), 3.38-3.36 (m, 2H); [M+Na]$^+$ 501.

Example 057

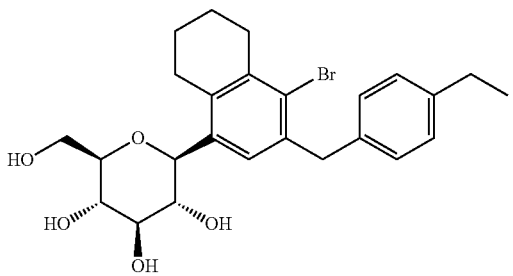 [SMILES: CCc1ccc(Cc2cc([C@@H]3O[C@H](CO)[C@@H](O)[C@H](O)[C@H]3O)c3c(c2Br)CCCC3)cc1]

(2S,3R,4R,5S,6R)-2-(4-Bromo-3-(4-ethylbenzyl)-5,6,7,8-tetrahydronaphthalen-1-yl)-6-(hydroxymethyl)tetrahydro-2H-pyran-3,4,5-triol (E057)

$^1$H NMR (400 MHz, CD$_3$OD) δ 7.30 (s, 1H), 7.14-7.09 (m, 4H), 4.52 (d, J=9.2 Hz, 1H), 4.18-4.10 (m, 2H), 3.90 (d, J=12.0 Hz, 1H), 3.71-3.67 (m, 1H), 3.57-3.51 (m, 2H), 3.46-3.40 (m, 2H), 3.06-2.98 (m, 1H), 2.93-2.86 (m, 1H), 2.84 (t, J=6.2 Hz, 2H), 2.63 (q, J=7.6 Hz, 2H), 1.86-1.77 (m, 4H), 1.24 (t, J=7.6 Hz, 3H); [M+Na]$^+$=513.

Example 058

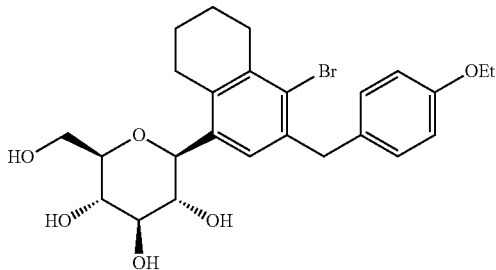 [SMILES: CCOc1ccc(Cc2cc([C@@H]3O[C@H](CO)[C@@H](O)[C@H](O)[C@H]3O)c3c(c2Br)CCCC3)cc1]

(2S,3R,4R,5S,6R)-2-(4-Bromo-3-(4-ethoxybenzyl)-5,6,7,8-tetrahydronaphthalen-1-yl)-6-(hydroxymethyl)tetrahydro-2H-pyran-3,4,5-triol (E058)

$^1$H NMR (400 MHz, CD$_3$OD) δ 7.29 (s, 1H), 7.12 (d, J=8.8 Hz, 2H), 6.82 (d, J=8.8 Hz, 2H), 4.52 (d, J=9.2 Hz, 1H), 4.10 (ABq, Δv$_{AB}$=7.4 Hz, J$_{AB}$=16.2 Hz, 2H), 4.03 (q, J=6.9 Hz, 2H), 3.90 (d, J=12.0 Hz, 1H), 3.72-3.67 (m, 1H), 3.58-3.51 (m, 2H), 3.46-3.41 (m, 2H), 3.06-2.98 (m, 1H), 2.93-2.86 (m, 1H), 2.83 (t, J=6.0 Hz, 2H), 1.88-1.74 (m, 4H), 1.40 (t, J=7.0 Hz, 3H); [M+Na]$^+$=529.

Example 059

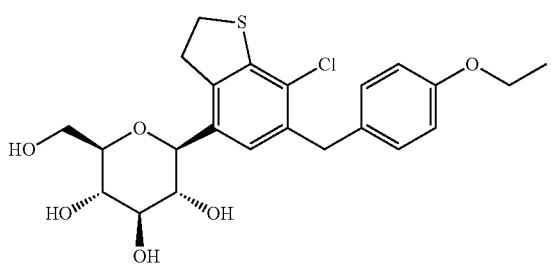 [SMILES: CCOc1ccc(Cc2cc([C@@H]3O[C@H](CO)[C@@H](O)[C@H](O)[C@H]3O)c3c(c2Cl)SCC3)cc1]

(2S,3R,4R,5S,6R)-2-(7-Chloro-6-(4-ethoxybenzyl)-2,3-dihydrobenzo[b]thiophen-4-yl)-6-(hydroxymethyl)tetrahydro-2H-pyran-3,4,5-triol (E059)

$^1$H NMR (400 MHz, MeOD) δ 7.08 (d, J=8.6 Hz, 2H), 7.05 (s, 1H), 6.79 (d, J=8.6 Hz, 2H), 4.21 (d, J=9.2 Hz, 1H), 4.01-3.95 (m, 4H), 3.92-3.86 (m, 1H), 3.69-3.65 (m, 1H), 3.60-3.54 (m, 1H), 3.48-3.40 (m, 3H), 3.38-3.34 (m, 4H), 1.35 (t, J=7.0 Hz, 3H); [M+Na]$^+$ 489.

Example 060

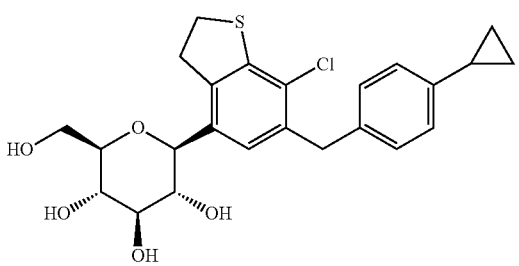 [SMILES: OC[C@H]1O[C@@H](c2cc(Cc3ccc(C4CC4)cc3)c(Cl)c3c2CCS3)[C@H](O)[C@@H](O)[C@@H]1O]

(2S,3R,4R,5S,6R)-2-(7-Chloro-6-(4-cyclopropylbenzyl)-2,3-dihydrobenzo[b]thiophen-4-yl)-6-(hydroxymethyl)tetrahydro-2H-pyran-3,4,5-triol (E060)

$^1$H NMR (400 MHz, MeOD) δ 7.04 (m, 3H), 6.95 (d, J=8.4 Hz, 2H), 4.21 (d, J=9.2 Hz, 1H), 3.98 (ABq, Δv$_{AB}$=16.3 Hz, J$_{AB}$=14.8 Hz, 2H), 3.87 (d, J=11.6 Hz, 1H), 3.69-3.65 (m, 1H), 3.62-3.54 (m, 1H), 3.48-3.41 (m, 3H), 3.40-3.34 (m, 4H), 1.88-1.81 (m, 1H), 0.93-0.88 (m, 2H), 0.63-0.59 (m, 2H); [M+Na]$^+$ 485.

Example 061

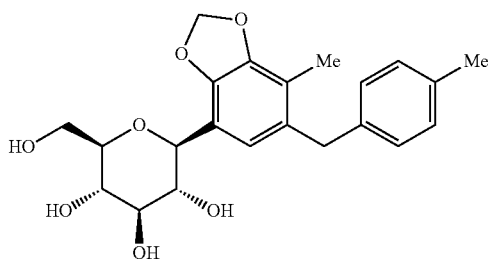 [SMILES: Cc1ccc(Cc2cc([C@@H]3O[C@H](CO)[C@@H](O)[C@H](O)[C@H]3O)c3c(c2C)OCO3)cc1]

(2R,3S,4R,5R,6S)-2-(Hydroxymethyl)-6-(7-methyl-6-(4-methylbenzyl)benzo[d][1,3]dioxol-4-yl)tetrahydro-2H-pyran-3,4,5-triol (E061)

$^1$H NMR (400 MHz, CD$_3$OD) δ 7.06 (d, J=8.0 Hz, 2H), 7.42 (d, J=8.0 Hz, 2H), 6.78 (s, 1H), 5.95 (dd, J=8.7 Hz, 1.0 Hz, 2H), 4.84 (s, 4H), 4.29 (d, J=9.7 Hz, 1H), 3.92-3.85 (m, 3H), 3.72-3.64 (m, 2H), 3.52-3.44 (m, 1H), 3.36-3.33 (m, 2H), 2.30 (s, 3H), 2.04 (s, 3H); [M+Na]$^+$ 425.

Example 062

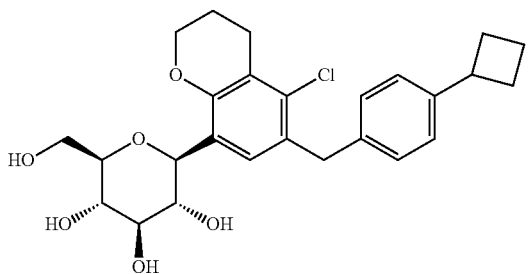 [SMILES: OC[C@H]1O[C@@H](c2cc(Cc3ccc(C4CCC4)cc3)c(Cl)c3c2OCCC3)[C@H](O)[C@@H](O)[C@@H]1O]

(2S,3R,4R,5S,6R)-2-(5-Chloro-6-(4-cyclobutylbenzyl)chroman-8-yl)-6-(hydroxymethyl)tetrahydro-2H-pyran-3,4,5-triol (E062)

$^1$H NMR (400 MHz, CD$_3$OD) δ 7.19 (s, 1H), 7.07 (s, 4H), 7.00 (s, 1H), 4.60 (d, J=9.2 Hz, 1H), 4.18-4.07 (m, 2H), 3.99 (ABq, Δν$_{AB}$=12.4 Hz, J$_{AB}$=15.2 Hz, 2H), 3.87-3.79 (m, 1H), 3.66-3.62 (m, 1H), 3.52-3.43 (m, 3H), 3.3-3.34 (m, 2H), 2.78 (d, J=6.8 Hz, 2H), 2.33-2.26 (m, 2H), 2.15-2.05 (m, 2H), 2.04-1.96 (m, 3H), 1.88-1.79 (m, 1H); [M+Na]$^+$ 497.

Example 063

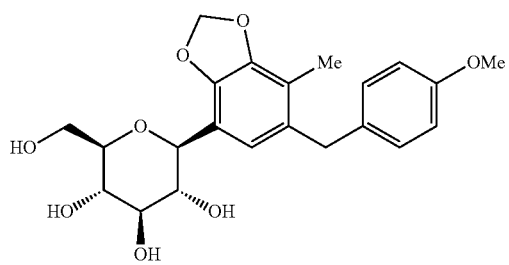 [SMILES: COc1ccc(Cc2cc([C@@H]3O[C@H](CO)[C@@H](O)[C@H](O)[C@H]3O)c3c(c2C)OCO3)cc1]

(2R,3S,4R,5R,6S)-2-(Hydroxymethyl)-6-(6-(4-methoxybenzyl)-7-methylbenzo[d][1,3]dioxol-4-yl)tetrahydro-2H-pyran-3,4,5-triol (E063)

$^1$H NMR (400 MHz, CD$_3$OD) δ 7.05 (d, J=8.6 Hz, 2H), 6.82 (d, J=8.6 Hz, 2H), 6.77 (s, 1H), 5.95 (dd, J=9.0 Hz, 1.0 Hz, 2H), 4.85 (s, 4H), 4.29 (d, J=9.7 Hz, 1H), 3.92-3.87 (m, 3H), 3.78 (s, 3H), 3.71-3.64 (m, 2H), 3.51-3.39 (m, 3H), 2.04 (s, 3H); [M+Na]$^+$ 441.

Example 064

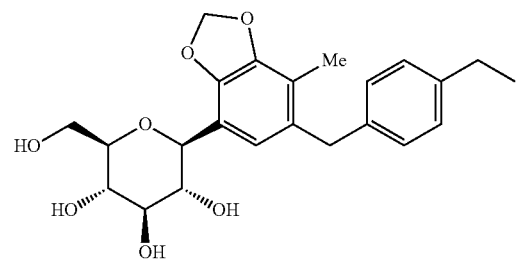 [SMILES: CCc1ccc(Cc2cc([C@@H]3O[C@H](CO)[C@@H](O)[C@H](O)[C@H]3O)c3c(c2C)OCO3)cc1]

(2S,3R,4R,5S,6R)-2-(6-(4-Ethylbenzyl)-7-methylbenzo[d][1,3]dioxol-4-yl)-6-(hydroxymethyl)tetrahydro-2H-pyran-3,4,5-triol (E064)

$^1$H NMR (400 MHz, CD$_3$OD) δ 7.10 (d, J=8.08 Hz, 2H), 7.05 (d, J=8.08 Hz, 2H), 6.79 (s, 1H), 5.95 (d, J=8.24 Hz, 2H), 4.29 (d, J=9.64 Hz, 1H), 3.91-3.88 (m, 3H), 3.70-3.66 (m, 2H), 3.50-3.46 (m, 1H), 3.41-3.39 (m, 2H), 2.61 (q, J=7.6 Hz, 2H), 2.05 (s, 3H), 1.22 (t, J=7.6 Hz, 3H); M+Na$^+$ 439

Example 065

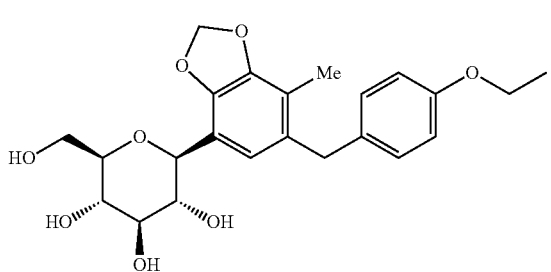 [SMILES: CCOc1ccc(Cc2cc([C@@H]3O[C@H](CO)[C@@H](O)[C@H](O)[C@H]3O)c3c(c2C)OCO3)cc1]

(2S,3R,4R,5S,6R)-2-(6-(4-Ethoxybenzyl)-7-methylbenzo[d][1,3]dioxol-4-yl)-6-(hydroxymethyl)tetrahydro-2H-pyran-3,4,5-triol (E065)

$^1$H NMR (400 MHz, CD$_3$OD) δ 7.04 (d, J=8.56 Hz, 2H), 6.81 (d, J=8.56 Hz, 2H), 6.77 (s, 1H), 5.95 (d, J=8.2 Hz, 2H), 4.29 (d, J=9.64 Hz, 1H), 4.01 (q, J=6.96 Hz, 2H), 3.91-3.88 (m, 3H), 3.70-3.68 (m, 2H), 3.50-3.45 (m, 1H), 3.41-3.39 (m, 2H), 2.05 (s, 3H), 1.38 (t, J=6.98 Hz, 3H); M+Na$^+$ 455

In vitro Assay

Test 1: Cloning and Cell Line Construction for Human SGLT2

Human SGLT2 (hSGLT2) gene was amplified by PCR from cDNA-Human Adult Normal Tissue Kidney (Invitrogen). The hSGLT2 sequence was cloned into pcDNA3.1(+)

for mammalian expression and stably transfected into chinese hamster ovary (CHO) cells. SGLT2-expressing clones were selected based on resistance to G418 antibiotic (Geneticin) and activity in the $^{14}$C-α-methyl-D-glucopyranoside ($^{14}$C-AMG) uptake assay.

Test 2: Inhibitory Effects on Human SGLT2 Activities

For sodium-dependent glucose transport assay, cells expressing hSGLT2 were seeded into a 96-well culture plate at a density of $5 \times 10^4$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_2$, and 1 mM MgCl$_2$, pH 7.4) at 37° C. for 10 min. They were then incubated in uptake buffer (10 mM HEPES, 5 mM Tris, 140 mM NaCl, 2 mM KCl, 1 mM CaCl$_2$, 1 mM MgCl$_2$, and 1 mM $^{14}$C-nonlabeled AMG pH 7.4) containing $^{14}$C-labeled AMG (8 μM) and the inventive compound or dimethyl sulfoxide (DMSO) vehicle at 37° C. for 2 h. Cells were washed twice with washing buffer (pretreatment buffer containing 10 mM AMG at room temperature) and then the radioactivity was measured using a liquid scintillation counter. IC$_{50}$ was determined by nonlinear regression analysis using GraphPad PRISM [Katsuno, K. et al. *J. Pharmacol. Exp. Ther.* 2007, 320, 323-330; Han, S. et al. *Diabetes*, 2008, 57, 1723-1729]. The inventive compounds and their IC$_{50}$ are shown in following Table 1.

Test 3: Inhibitory Effects on Human SGLT1 Activities

For sodium-dependent glucose transport assay, cells expressing hSGLT2 were seeded into a 96-well culture plate at a density of $5 \times 10^4$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_2$, and 1 mM MgCl$_2$, pH 7.4) at 37° C. for 10 min. They were then incubated in uptake buffer (10 mM HEPES, 5 mM Tris, 140 mM NaCl, 2 mM KCl, 1 mM CaCl$_2$, 1 mM MgCl$_2$, and 1 mM $^{14}$C-nonlabeled AMG pH 7.4) containing $^{14}$C-labeled (8 μM) and inhibitor or dimethyl sulfoxide (DMSO) vehicle at 37° C. for 2 h. Cells were washed twice with washing buffer (pretreatment buffer containing 10 mM AMG at room temperature) and then the radioactivity was measured using a liquid scintillation counter. IC$_{50}$ was determined by nonlinear regression analysis using GraphPad PRISM. The inventive compounds and their IC$_{50}$ are shown in following Table 1.

TABLE 1 hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E001 | 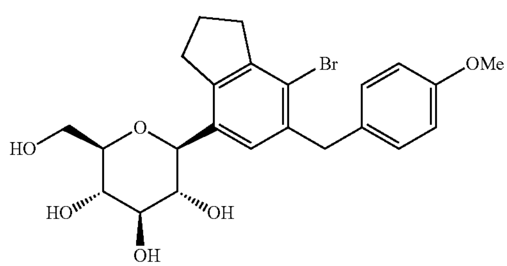 [SMILES: COc1ccc(Cc2cc([C@@H]3O[C@H](CO)[C@@H](O)[C@H](O)[C@H]3O)c3c(c2Br)CCC3)cc1] | (2S,3R,4R,5S,6R)-2-(7-bromo-6-(4-methoxybenzyl)-2,3-dihydro-1H-inden-4-yl)-6-(hydroxymethyl)tetrahydro-2H-pyran-3,4,5-triol | 0.44 | 15.2 |
| E002 | 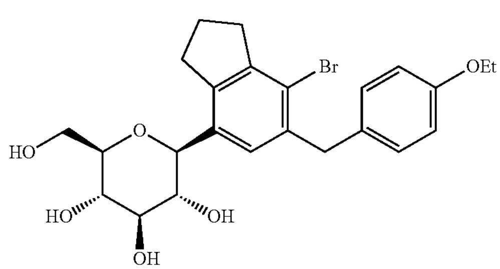 [SMILES: CCOc1ccc(Cc2cc([C@@H]3O[C@H](CO)[C@@H](O)[C@H](O)[C@H]3O)c3c(c2Br)CCC3)cc1] | (2S,3R,4R,5S,6R)-2-(7-bromo-6-(4-ethoxybenzyl)-2,3-dihydro-1H-inden-4-yl)-6-(hydroxymethyl)tetrahydro-2H-pyran-3,4,5-triol | 0.75 | 62.7 |
| E003 | 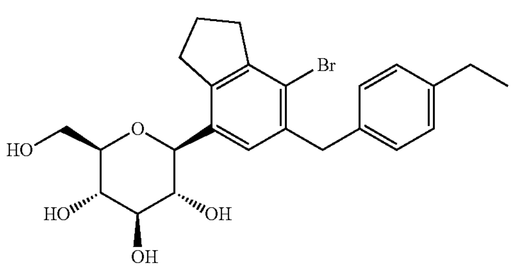 | (2S,3R,4R,5S,6R)-2-(7-bromo-6-(4-ethylbenzyl)-2,3-dihydro-1H-inden-4-yl)-6-(hydroxymethyl)tetrahydro-2H-pyran-3,4,5-triol | 0.61 | 45.4 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E004 | 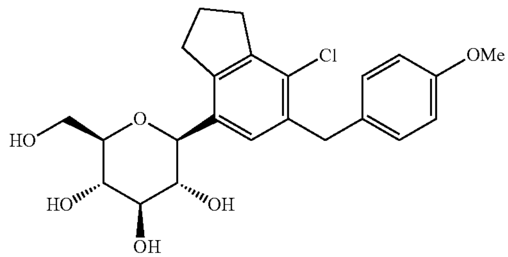 [SMILES: COc1ccc(Cc2cc([C@@H]3O[C@H](CO)[C@@H](O)[C@H](O)[C@H]3O)c3c(c2Cl)CCC3)cc1] | (2S,3R,4R,5S,6R)-2-(7-chloro-6-(4-methoxybenzyl)-2,3-dihydro-1H-inden-4-yl)-6-(hydroxymethyl)tetrahydro-2H-pyran-3,4,5-triol | 0.68 | 37.2 |
| E005 | 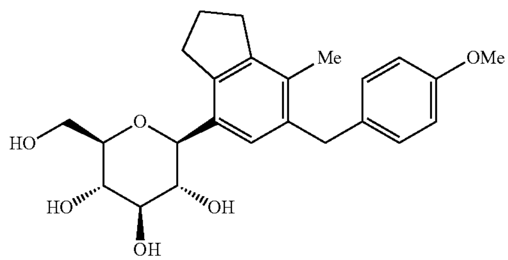 [SMILES: COc1ccc(Cc2cc([C@@H]3O[C@H](CO)[C@@H](O)[C@H](O)[C@H]3O)c3c(c2C)CCC3)cc1] | (2R,3S,4R,5R,6S)-2-(hydroxymethyl)-6-(6-(4-methoxybenzyl)-7-methyl-2,3-dihydro-1H-inden-4-yl)tetrahydro-2H-pyran-3,4,5-triol | 0.79 | 26.8 |
| E006 | 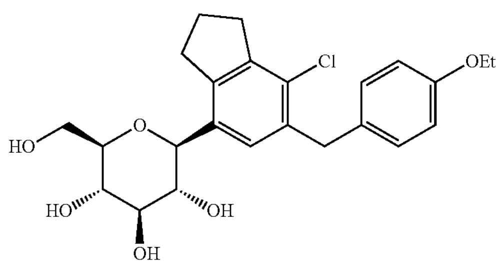 | (2S,3R,4R,5S,6R)-2-(7-chloro-6-(4-ethoxybenzyl)-2,3-dihydro-1H-inden-4-yl)-6-(hydroxymethyl)tetrahydro-2H-pyran-3,4,5-triol | 0.55 | 116 |
| E007 | 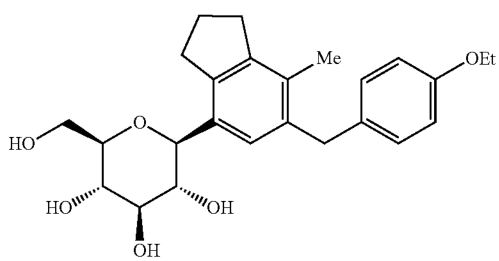 [SMILES: CCOc1ccc(Cc2cc([C@@H]3O[C@H](CO)[C@@H](O)[C@H](O)[C@H]3O)c3c(c2C)CCC3)cc1] | (2S,3R,4R,5S,6R)-2-(6-(4-ethoxybenzyl)-7-methyl-2,3-dihydro-1H-inden-4-yl)-6-(hydroxymethyl)tetrahydro-2H-pyran-3,4,5-triol | 1.2 | 160 |
| E008 | 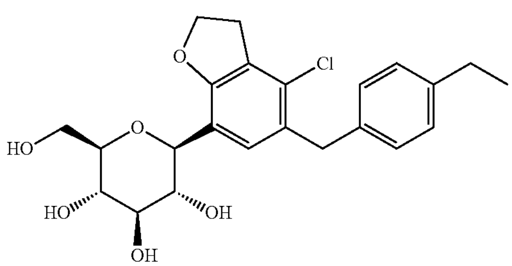 | (2S,3R,4R,5S,6R)-2-(4-chloro-5-(4-ethylbenzyl)-2,3-dihydrobenzofuran-7-yl)-6-(hydroxymethyl)tetrahydro-2H-pyran-3,4,5-triol | 0.88 | 44.0 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E009 | 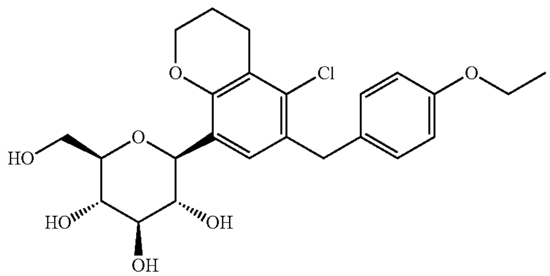 | (2S,3R,4R,5S,6R)-2-(5-chloro-6-(4-ethoxybenzyl)chroman-8-yl)-6-(hydroxymethyl)tetrahydro-2H-pyran-3,4,5-triol | 1.6 | 77.2 |
| E010 | 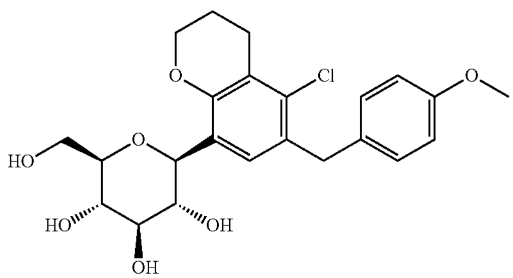 | (2S,3R,4R,5S,6R)-2-(5-chloro-6-(4-methoxybenzyl)chroman-8-yl)-6-(hydroxymethyl)tetrahydro-2H-pyran-3,4,5-triol | 1.6 | 16.9 |
| E011 | 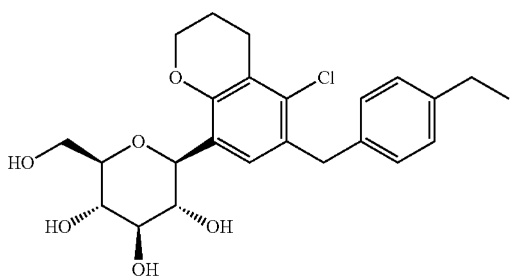 | (2S,3R,4R,5S,6R)-2-(5-chloro-6-(4-ethylbenzyl)chroman-8-yl)-6-(hydroxymethyl)tetrahydro-2H-pyran-3,4,5-triol | 0.85 | 27.0 |
| E012 | 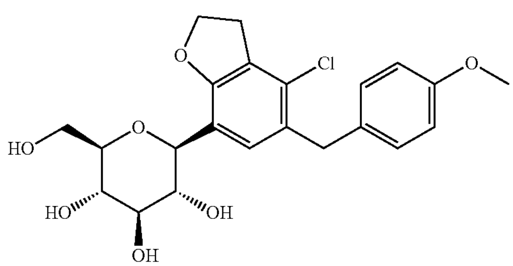 | (2S,3R,4R,5S,6R)-2-(4-chloro-5-(4-methoxybenzyl)-2,3-dihydrobenzofuran-7-yl)-6-(hydroxymethyl)tetrahydro-2H-pyran-3,4,5-triol | 1.7 | 34.4 |
| E013 | 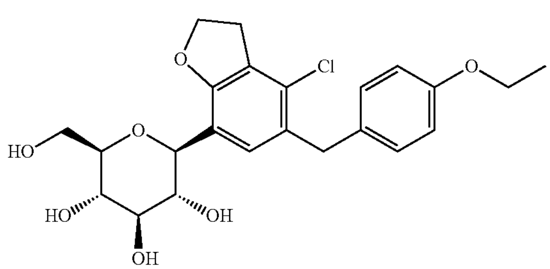 [SMILES: CCOc1ccc(Cc2cc([C@@H]3O[C@H](CO)[C@@H](O)[C@H](O)[C@H]3O)c3c(c2Cl)CCO3)cc1] | (2S,3R,4R,5S,6R)-2-(4-chloro-5-(4-ethoxybenzyl)-2,3-dihydrobenzofuran-7-yl)-6-(hydroxymethyl)tetrahydro-2H-pyran-3,4,5-triol | 0.83 | 105 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E014 | 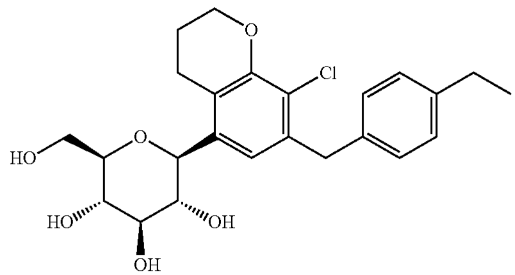 [SMILES: CCc1ccc(Cc2cc([C@@H]3O[C@H](CO)[C@@H](O)[C@H](O)[C@H]3O)c3c(c2Cl)OCCC3)cc1] | (2S,3R,4R,5S,6R)-2-(8-chloro-7-(4-ethylbenzyl)chroman-5-yl)-6-(hydroxymethyl)tetrahydro-2H-pyran-3,4,5-triol | 0.75 | 61.5 |
| E015 | 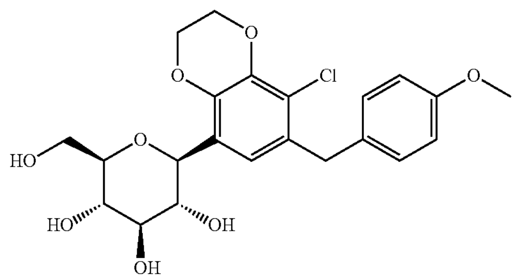 | (2S,3R,4R,5S,6R)-2-(8-chloro-7-(4-methoxybenzyl)-2,3-dihydrobenzo[b][1,4]dioxin-5-yl)-6-(hydroxymethyl)tetrahydro-2H-pyran-3,4,5-triol | 2.0 | 34.0 |
| E016 | 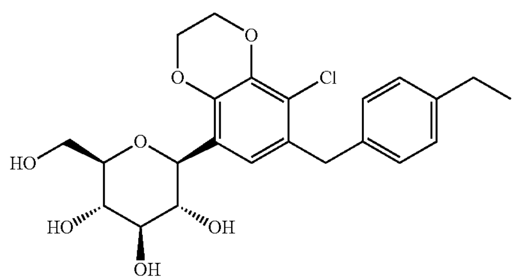 | (2S,3R,4R,5S,6R)-2-(8-chloro-7-(4-ethylbenzyl)-2,3-dihydrobenzo[b][1,4]dioxin-5-yl)-6-(hydroxymethyl)tetrahydro-2H-pyran-3,4,5-triol | 0.92 | 83.0 |
| E017 | 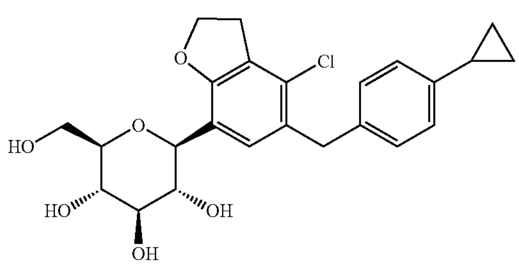 [SMILES: OC[C@H]1O[C@@H](c2cc(Cc3ccc(C4CC4)cc3)c(Cl)c3c2OCC3)[C@H](O)[C@@H](O)[C@@H]1O] | (2S,3R,4R,5S,6R)-2-(4-Chloro-5-(4-cyclopropylbenzyl)-2,3-dihydrobenzofuran-7-yl)-6-(hydroxymethyl)tetrahydro-2H-pyran-3,4,5-triol | 1.1 | 52.2 |
| E018 | 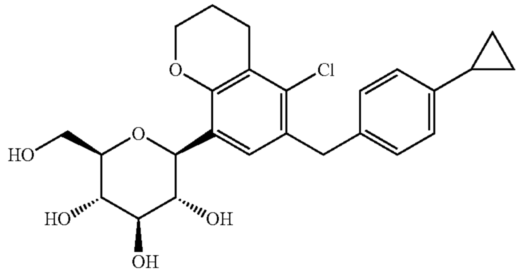 [SMILES: OC[C@H]1O[C@@H](c2cc(Cc3ccc(C4CC4)cc3)c(Cl)c3c2OCCC3)[C@H](O)[C@@H](O)[C@@H]1O] | ((2S,3R,4R,5S,6R)-2-(5-Chloro-6-(4-cyclopropylbenzyl)chroman-8-yl)-6-(hydroxymethyl)tetrahydro-2H-pyran-3,4,5-triol | 0.85 | 26.6 |

TABLE 1-continued hSGLT2 and hSGLT1 Inhibitory Activities

| Compound | Name | SGLT2 IC$_{50}$ (nM) | SGLT1 IC$_{50}$ (nM) |
|---|---|---|---|
| E019 | (2S,3R,4R,5S,6R)-2-(4-chloro-5-(4-ethylbenzyl)-2-methyl-2,3-dihydrobenzo[b]thiophen-7-yl)-6-(hydroxymethyl)tetrahydro-2H-pyran-3,4,5-triol | 0.98 | 111 |
| E020 | (2S,3R,4R,5S,6R)-2-(4-chloro-5-(4-ethoxybenzyl)-2-methyl-2,3-dihydrobenzofuran-7-yl)-6-(methylthio)tetrahydro-2H-pyran-3,4,5-triol | 0.69 | 115 |
| E021 | (2S,3R,4R,5S,6R)-2-(8-chloro-7-(4-ethoxybenzyl)-2,3-dihydrobenzo[b][1,4]dioxin-5-yl)-6-(methylthio)tetrahydro-2H-pyran-3,4,5-triol | 0.71 | 166 |
| E022 | (2S,3R,4R,5S,6R)-2-(8-chloro-7-(4-cyclopropylbenzyl)chroman-5-yl)-6-(hydroxymethyl)tetrahydro-2H-pyran-3,4,5-triol | 0.88 | 50.0 |
| E023 | (2S,3R,4R,5S,6R)-2-(8-chloro-7-(4-methoxybenzyl)chroman-5-yl)-6-(hydroxymethyl)tetrahydro-2H-pyran-3,4,5-triol | 2.1 | 78.1 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E024 | 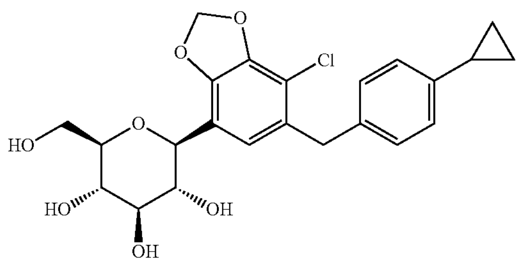 | (2S,3R,4R,5S,6R)-2-(7-chloro-6-(4-cyclopropylbenzyl)benzo[d][1,3]dioxol-4-yl)-6-(hydroxymethyl)tetrahydro-2H-pyran-3,4,5-triol | 0.37 | 53.0 |
| E025 | 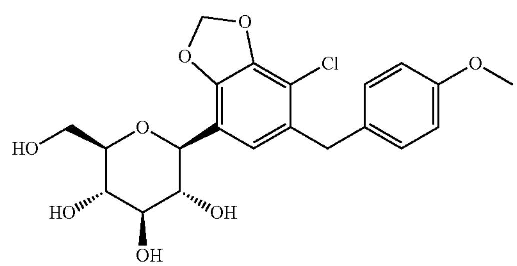 [SMILES: COc1ccc(Cc2cc([C@@H]3O[C@H](CO)[C@@H](O)[C@H](O)[C@H]3O)c3c(c2Cl)OCO3)cc1] | (2S,3R,4R,5S,6R)-2-(7-chloro-6-(4-methoxybenzyl)benzo[d][1,3]dioxol-4-yl)-6-(hydroxymethyl)tetrahydro-2H-pyran-3,4,5-triol | 1.2 | 89.4 |
| E026 | 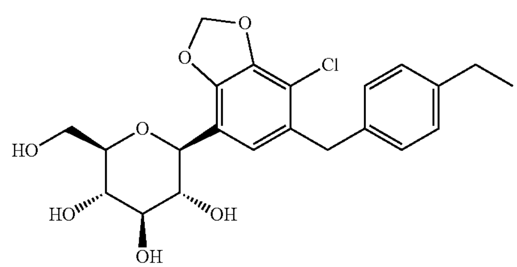 [SMILES: CCc1ccc(Cc2cc([C@@H]3O[C@H](CO)[C@@H](O)[C@H](O)[C@H]3O)c3c(c2Cl)OCO3)cc1] | (2S,3R,4R,5S,6R)-2-(7-chloro-6-(4-ethylbenzyl)benzo[d][1,3]dioxol-4-yl)-6-(hydroxymethyl)tetrahydro-2H-pyran-3,4,5-triol | 0.40 | 86.9 |
| E027 | 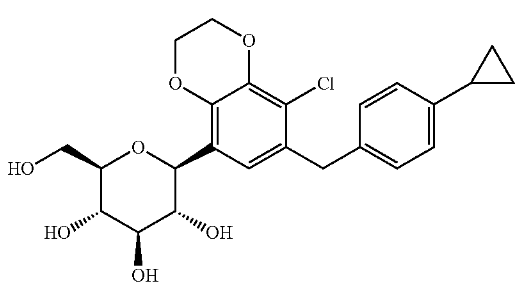 | (2S,3R,4R,5S,6R)-2-(8-chloro-7-(4-cyclopropylbenzyl)-2,3-dihydrobenzo[b][1,4]dioxin-5-yl)-6-(hydroxymethyl)tetrahydro-2H-pyran-3,4,5-triol | 0.65 | 41.9 |
| E028 | 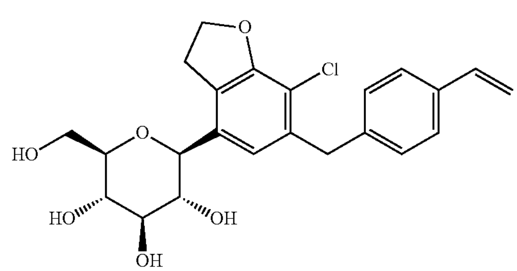 [SMILES: C=Cc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-vinylbenzyl)-2,3-dihydrobenzofuran-4-yl)-6-(hydroxymethyl)tetrahydro-2H-pyran-3,4,5-triol | 0.37 | 163 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E029 | 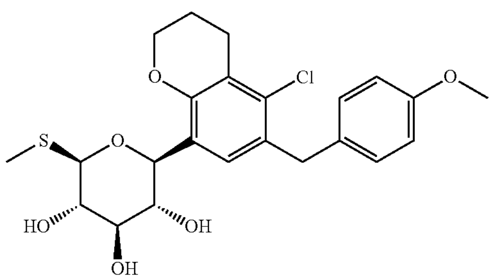 | (2S,3R,4R,5S,6R)-2-(5-chloro-6-(4-methoxybenzyl)chroman-8-yl)-6-(methylthio)tetrahydro-2H-pyran-3,4,5-triol | 0.47 | 21.1 |
| E030 | 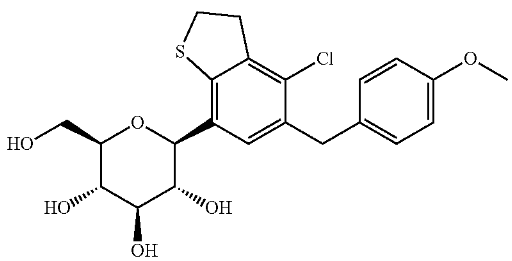 | (2S,3R,4R,5S,6R)-2-(4-chloro-5-(4-methoxybenzyl)-2,3-dihydrobenzo[b]thiophen-7-yl)-6-(hydroxymethyl)tetrahydro-2H-pyran-3,4,5-triol | 2.3 | 171 |
| E031 | 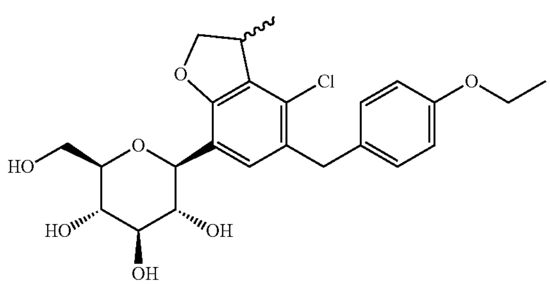 [SMILES: CCOc1ccc(Cc2cc([C@@H]3O[C@H](CO)[C@@H](O)[C@H](O)[C@H]3O)c3c(c2Cl)C(C)CO3)cc1] | (2S,3R,4R,5S,6R)-2-(4-Chloro-5-(4-ethoxybenzyl)-3-methyl-2,3-dihydrobenzofuran-7-yl)-6-(hydroxymethyl)-tetrahydro-2H-pyran-3,4,5-triol | 2.0 | 196 |
| E032 | 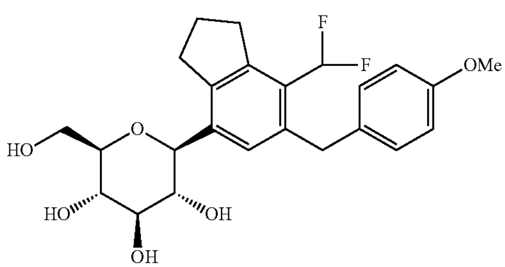 [SMILES: COc1ccc(Cc2cc([C@@H]3O[C@H](CO)[C@@H](O)[C@H](O)[C@H]3O)c3c(c2C(F)F)CCC3)cc1] | (2S,3R,4R,5S,6R)-2-(7-(difluoromethyl)-6-(4-methoxybenzyl)-2,3-dihydro-1H-inden-4-yl)-6-(hydroxymethyl)tetrahydro-2H-pyran-3,4,5-triol | 0.73 | 16.5 |
| E033 | 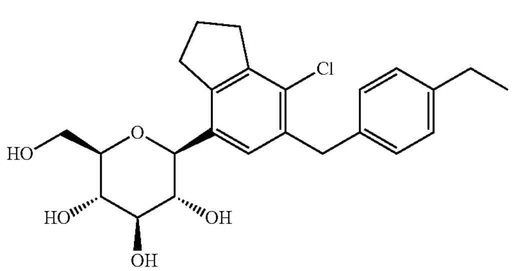 | (2S,3R,4R,5S,6R)-2-(7-chloro-6-(4-ethylbenzyl)-2,3-dihydro-1H-inden-4-yl)-6-(hydroxymethyl)tetrahydro-2H-pyran-3,4,5-triol | 0.63 | 57.2 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E034 | 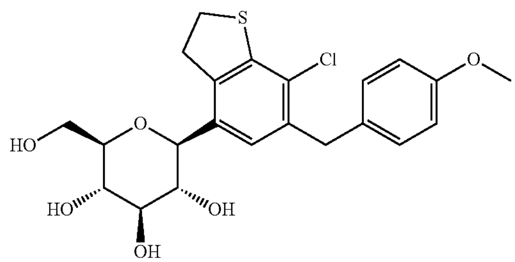 [SMILES: COc1ccc(Cc2cc([C@@H]3O[C@H](CO)[C@@H](O)[C@H](O)[C@H]3O)c3c(c2Cl)SCC3)cc1] | (2S,3R,4R,5S,6R)-2-(7-chloro-6-(4-methoxybenzyl)-2,3-dihydrobenzo[b]thiophen-4-yl)-6-(hydroxymethyl)tetrahydro-2H-pyran-3,4,5-triol | 0.90 | 27.6 |
| E035 | 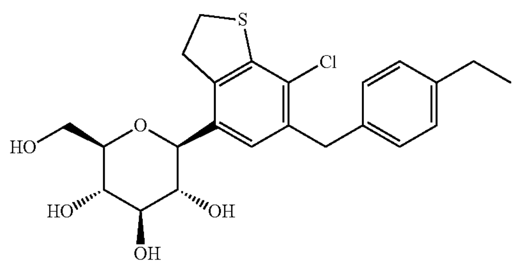 [SMILES: CCc1ccc(Cc2cc([C@@H]3O[C@H](CO)[C@@H](O)[C@H](O)[C@H]3O)c3c(c2Cl)SCC3)cc1] | (2S,3R,4R,5S,6R)-2-(7-chloro-6-(4-ethylbenzyl)-2,3-dihydrobenzo[b]thiophen-4-yl)-6-(hydroxymethyl)tetrahydro-2H-pyran-3,4,5-triol | 0.87 | 53.0 |
| E036 | 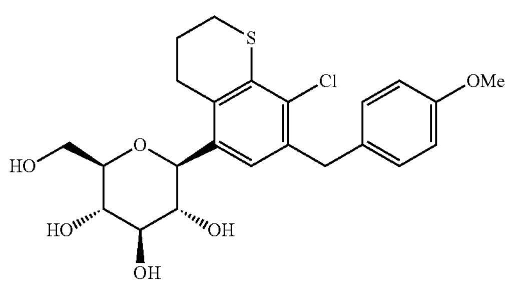 [SMILES: COc1ccc(Cc2cc([C@@H]3O[C@H](CO)[C@@H](O)[C@H](O)[C@H]3O)c3c(c2Cl)SCCC3)cc1] | (2S,3R,4R,5S,6R)-2-(8-chloro-7-(4-methoxybenzyl)thiochroman-5-yl)-6-(hydroxymethyl)tetrahydro-2H-pyran-3,4,5-triol | 0.55 | 10.7 |
| E037 | 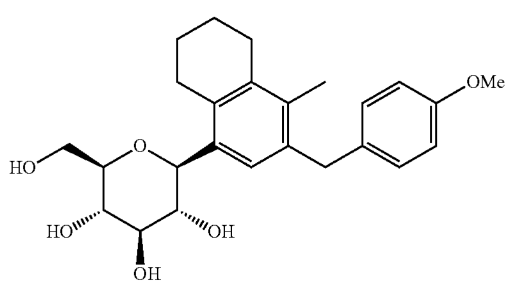 [SMILES: COc1ccc(Cc2cc([C@@H]3O[C@H](CO)[C@@H](O)[C@H](O)[C@H]3O)c3c(c2C)CCCC3)cc1] | (2R,3S,4R,5R,6S)-2-(hydroxymethyl)-6-(3-(4-methoxybenzyl)-4-methyl-5,6,7,8-tetrahydronaphthalen-1-yl)tetrahydro-2H-pyran-3,4,5-triol | 0.86 | 10.5 |
| E038 | 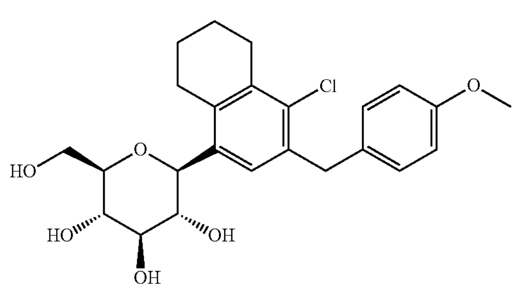 [SMILES: COc1ccc(Cc2cc([C@@H]3O[C@H](CO)[C@@H](O)[C@H](O)[C@H]3O)c3c(c2Cl)CCCC3)cc1] | (2S,3R,4R,5S,6R)-2-(4-chloro-3-(4-methoxybenzyl)-5,6,7,8-tetrahydronaphthalen-1-yl)-6-(hydroxymethyl)tetrahydro-2H-pyran-3,4,5-triol | 0.60 | 9.6 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E039 | 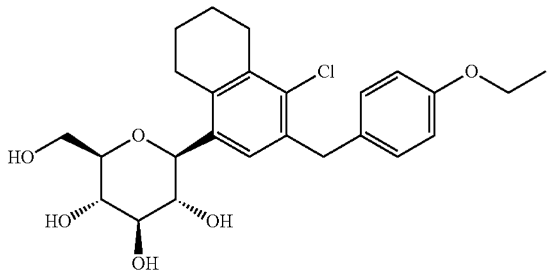 | (2S,3R,4R,5S,6R)-2-(4-chloro-3-(4-ethoxybenzyl)-5,6,7,8-tetrahydronaphthalen-1-yl)-6-(hydroxymethyl)tetrahydro-2H-pyran-3,4,5-triol | 0.62 | 33.2 |
| E040 | 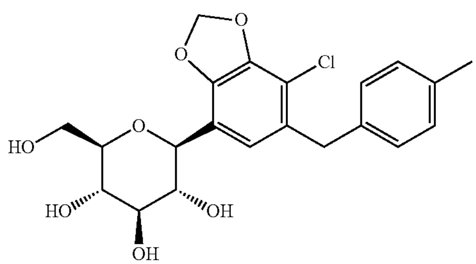 [SMILES: Cc1ccc(Cc2cc([C@@H]3O[C@H](CO)[C@@H](O)[C@H](O)[C@H]3O)c3c(c2Cl)OCO3)cc1] | (2S,3R,4R,5S,6R)-2-(7-chloro-6-(4-methylbenzyl)benzo[d][1,3]dioxol-4-yl)-6-(hydroxymethyl)tetrahydro-2H-pyran-3,4,5-triol | 1.0 | 94.6 |
| E041 | 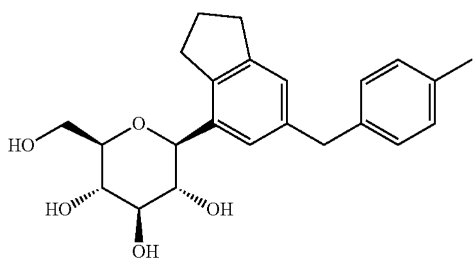 [SMILES: Cc1ccc(Cc2cc3c(c([C@@H]4O[C@H](CO)[C@@H](O)[C@H](O)[C@H]4O)c2)CCC3)cc1] | (2R,3S,4R,5R,6S)-2-(hydroxymethyl)-6-(6-(4-methylbenzyl)-2,3-dihydro-1H-inden-4-yl)tetrahydro-2H-pyran-3,4,5-triol | 8.0 | 91.0 |
| E042 | 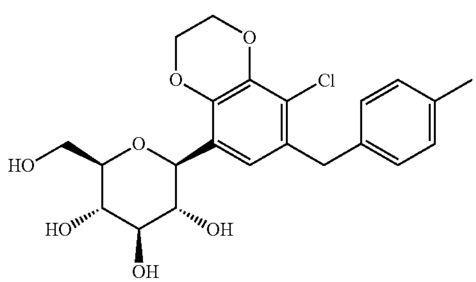 | (2S,3R,4R,5S,6R)-2-(8-chloro-7-(4-methylbenzyl)-2,3-dihydrobenzo[b][1,4]dioxin-5-yl)-6-(hydroxymethyl)tetrahydro-2H-pyran-3,4,5-triol | 1.0 | 9.2 |
| E043 | 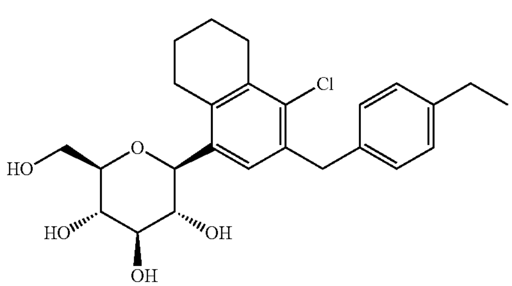 | (2S,3R,4R,5S,6R)-2-(4-chloro-3-(4-ethylbenzyl)-5,6,7,8-tetrahydronaphthalen-1-yl)-6-(hydroxymethyl)tetrahydro-2H-pyran-3,4,5-triol | 0.49 | 32.6 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E044 | 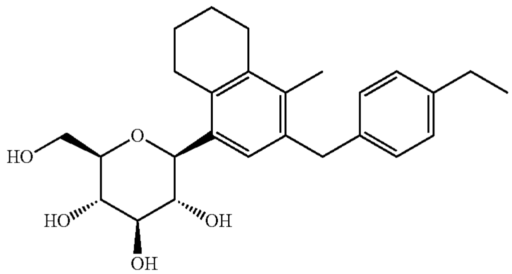 [SMILES: CCc1ccc(Cc2cc([C@@H]3O[C@H](CO)[C@@H](O)[C@H](O)[C@H]3O)c3c(c2C)CCCC3)cc1] | (2S,3R,4R,5S,6R)-2-(3-(4-ethylbenzyl)-4-methyl-5,6,7,8-tetrahydronaphthalen-1-yl)-6-(hydroxymethyl)tetrahydro-2H-pyran-3,4,5-triol | 0.59 | 10.4 |
| E045 | 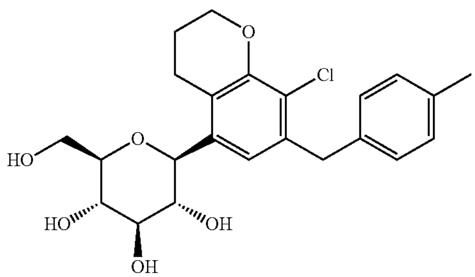 | (2S,3R,4R,5S,6R)-2-(8-chloro-7-(4-methylbenzyl)chroman-5-yl)-6-(hydroxymethyl)tetrahydro-2H-pyran-3,4,5-triol | 1.9 | 36.7 |
| E046 | 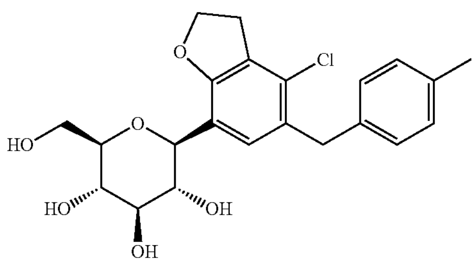 [SMILES: Cc1ccc(Cc2cc([C@@H]3O[C@H](CO)[C@@H](O)[C@H](O)[C@H]3O)c3c(c2Cl)CCO3)cc1] | (2S,3R,4R,5S,6R)-2-(4-chloro-5-(4-methylbenzyl)-2,3-dihydrobenzofuran-7-yl)-6-(hydroxymethyl)tetrahydro-2H-pyran-3,4,5-triol | 1.4 | 29.9 |
| E047 | 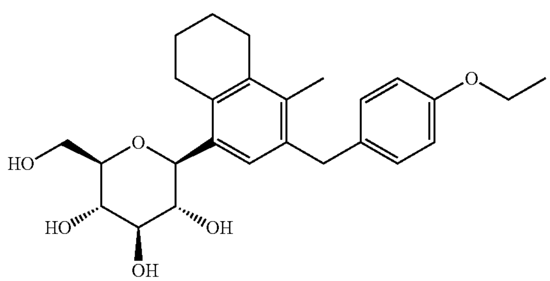 [SMILES: CCOc1ccc(Cc2cc([C@@H]3O[C@H](CO)[C@@H](O)[C@H](O)[C@H]3O)c3c(c2C)CCCC3)cc1] | (2S,3R,4R,5S,6R)-2-(3-(4-ethoxybenzyl)-4-methyl-5,6,7,8-tetrahydronaphthalen-1-yl)-6-(hydroxymethyl)tetrahydro-2H-pyran-3,4,5-triol | 1.3 | 27.1 |
| E048 | 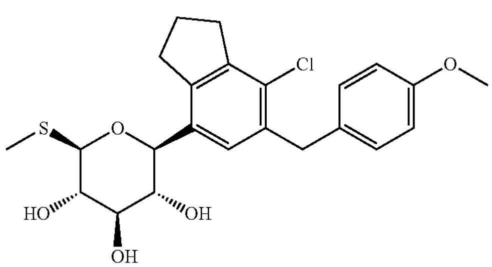 | (2S,3R,4R,5S,6R)-2-(7-chloro-6-(4-methoxybenzyl)-2,3-dihydro-1H-inden-4-yl)-6-(methylthio)tetrahydro-2H-pyran-3,4,5-triol | 0.50 | 33.7 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E049 | 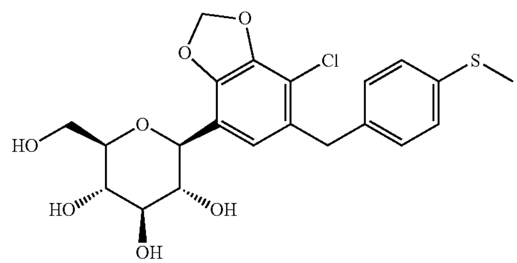 [SMILES: CSc1ccc(Cc2cc([C@@H]3O[C@H](CO)[C@@H](O)[C@H](O)[C@H]3O)c3c(c2Cl)OCO3)cc1] | (2S,3R,4R,5S,6R)-2-(7-chloro-6-(4-(methylthio)benzyl)benzo[d][1,3]dioxol-4-yl)-6-(hydroxymethyl)tetrahydro-2H-pyran-3,4,5-triol | 0.80 | 50.3 |
| E050 | 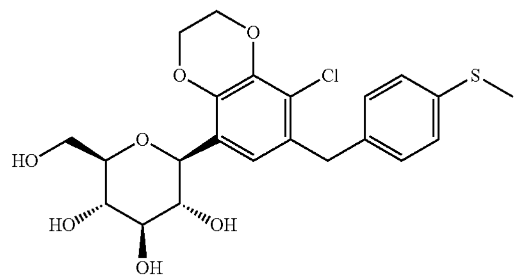 [SMILES: CSc1ccc(Cc2cc([C@@H]3O[C@H](CO)[C@@H](O)[C@H](O)[C@H]3O)c3c(c2Cl)OCCO3)cc1] | (2S,3R,4R,5S,6R)-2-(8-chloro-7-(4-(methylthio)benzyl)-2,3-dihydrobenzo[b][1,4]dioxin-5-yl)-6-(hydroxymethyl)tetrahydro-2H-pyran-3,4,5-triol | 0.85 | 23.2 |
| E051 | 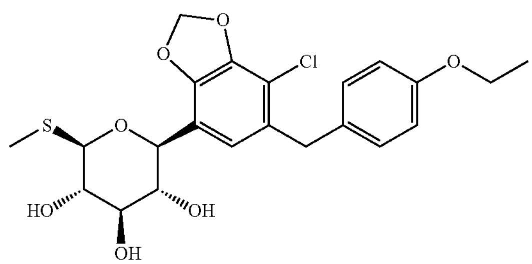 [SMILES: CCOc1ccc(Cc2cc([C@@H]3O[C@H](SC)[C@@H](O)[C@H](O)[C@H]3O)c3c(c2Cl)OCO3)cc1] | (2S,3R,4R,5S,6R)-2-(7-chloro-6-(4-ethoxybenzyl)benzo[d][1,3]dioxol-4-yl)-6-(methylthio)tetrahydro-2H-pyran-3,4,5-triol | 0.49 | 62.4 |
| E052 | 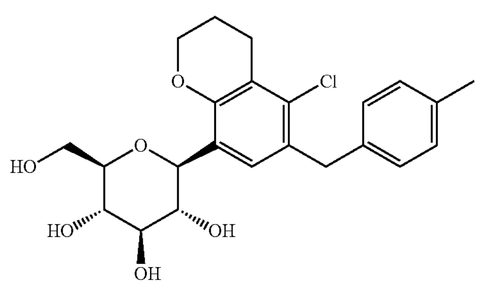 | (2S,3R,4R,5S,6R)-2-(5-chloro-6-(4-methylbenzyl)chroman-8-yl)-6-(hydroxymethyl)tetrahydro-2H-pyran-3,4,5-triol | 1.1 | 9.2 |
| E053 | 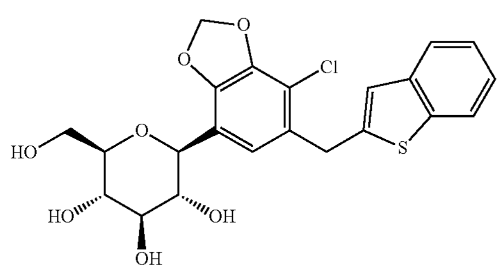 [SMILES: OC[C@H]1O[C@@H](c2cc(Cc3cc4ccccc4s3)c(Cl)c3c2OCO3)[C@H](O)[C@@H](O)[C@@H]1O] | (2S,3R,4R,5S,6R)-2-(6-(benzo[b]thiophen-2-ylmethyl)-7-chlorobenzo[d][1,3]dioxol-4-yl)-6-(hydroxymethyl)tetrahydro-2H-pyran-3,4,5-triol | 1.5 | 41.0 |

TABLE 1-continued hSGLT2 and hSGLT1 Inhibitory Activities

| Compound | Name | SGLT2 IC$_{50}$ (nM) | SGLT1 IC$_{50}$ (nM) |
|---|---|---|---|
| E054 | (2S,3R,4R,5S,6R)-2-(8-chloro-7-((5-(4-fluorophenyl)thiophen-2-yl)methyl)-2,3-dihydrobenzo[b][1,4]dioxin-5-yl)-6-(hydroxymethyl)tetrahydro-2H-pyran-3,4,5-triol | 1.1 | 125 |
| E055 | (2S,3R,4R,5S,6R)-2-(6-(benzo[b]thiophen-2-ylmethyl)-7-chloro-2,3-dihydrobenzofuran-4-yl)-6-(hydroxymethyl)tetrahydro-2H-pyran-3,4,5-triol | 1.4 | 148 |
| E056 | (2S,3R,4R,5S,6R)-2-(7-(benzo[b]thiophen-2-ylmethyl)-8-chloro-2,3-dihydrobenzo[b][1,4]dioxin-5-yl)-6-(hydroxymethyl)tetrahydro-2H-pyran-3,4,5-triol | 2.2 | 14.0 |
| E057 | (2S,3R,4R,5S,6R)-2-(4-bromo-3-(4-ethylbenzyl)-5,6,7,8-tetrahydronaphthalen-1-yl)-6-(hydroxymethyl)tetrahydro-2H-pyran-3,4,5-triol | 0.86 | 11.0 |
| E058 | (2S,3R,4R,5S,6R)-2-(4-bromo-3-(4-ethoxybenzyl)-5,6,7,8-tetrahydronaphthalen-1-yl)-6-(hydroxymethyl)tetrahydro-2H-pyran-3,4,5-triol | 0.87 | 17.1 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E059 | 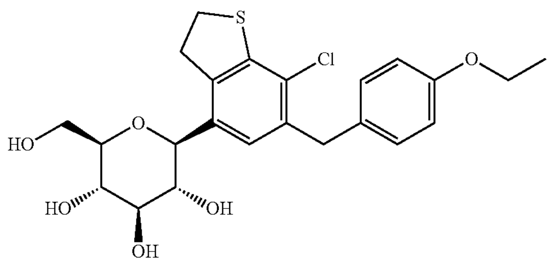 [SMILES: CCOc1ccc(Cc2cc([C@@H]3O[C@H](CO)[C@@H](O)[C@H](O)[C@H]3O)c3c(c2Cl)SCC3)cc1] | (2S,3R,4R,5S,6R)-2-(7-chloro-6-(4-ethoxybenzyl)-2,3-dihydrobenzo[b]thiophen-4-yl)-6-(hydroxymethyl)tetrahydro-2H-pyran-3,4,5-triol | 1.1 | 95.1 |
| E060 | 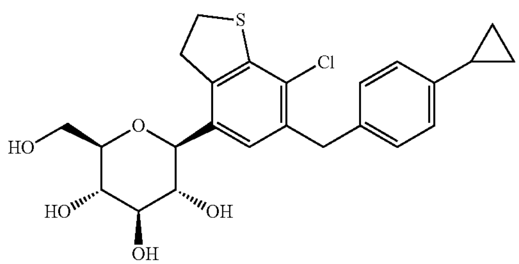 [SMILES: OC[C@H]1O[C@@H](c2cc(Cc3ccc(C4CC4)cc3)c(Cl)c3c2CCS3)[C@H](O)[C@@H](O)[C@@H]1O] | (2S,3R,4R,5S,6R)-2-(7-chloro-6-(4-cyclopropylbenzyl)-2,3-dihydrobenzo[b]thiophen-4-yl)-6-(hydroxymethyl)tetrahydro-2H-pyran-3,4,5-triol | 0.67 | 40.9 |
| E061 | 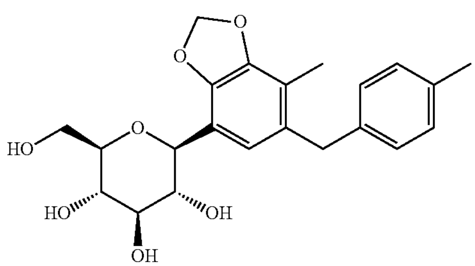 [SMILES: Cc1ccc(Cc2cc([C@@H]3O[C@H](CO)[C@@H](O)[C@H](O)[C@H]3O)c3c(c2C)OCO3)cc1] | (2R,3S,4R,5R,6S)-2-(hydroxymethyl)-6-(7-methyl-6-(4-methylbenzyl)benzo[d][1,3]dioxol-4-yl)tetrahydro-2H-pyran-3,4,5-triol | 1.7 | 27.0 |
| E062 | 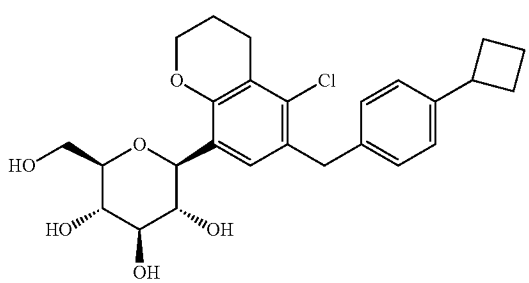 [SMILES: OC[C@H]1O[C@@H](c2cc(Cc3ccc(C4CCC4)cc3)c(Cl)c3c2OCCC3)[C@H](O)[C@@H](O)[C@@H]1O] | (2S,3R,4R,5S,6R)-2-(5-chloro-6-(4-cyclobutylbenzyl)chroman-8-yl)-6-(hydroxymethyl)tetrahydro-2H-pyran-3,4,5-triol | 1.1 | 163 |
| E063 | 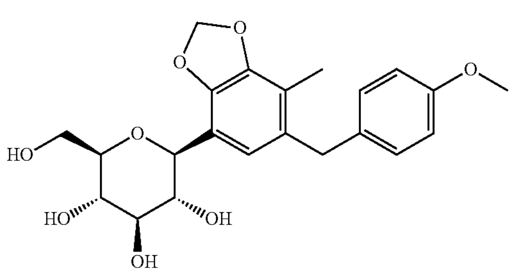 [SMILES: COc1ccc(Cc2cc([C@@H]3O[C@H](CO)[C@@H](O)[C@H](O)[C@H]3O)c3c(c2C)OCO3)cc1] | (2R,3S,4R,5R,6S)-2-(hydroxymethyl)-6-(6-(4-methoxybenzyl)-7-methylbenzo[d][1,3]dioxol-4-yl)tetrahydro-2H-pyran-3,4,5-triol | 1.6 | 66.2 |

TABLE 1-continued hSGLT2 and hSGLT1 Inhibitory Activities

| Compound | Structure | Name | SGLT2 IC$_{50}$ (nM) | SGLT1 IC$_{50}$ (nM) |
|---|---|---|---|---|
| E064 | 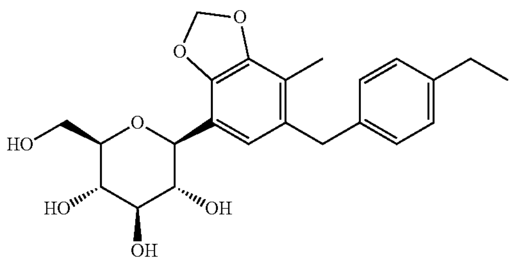 [SMILES: CCc1ccc(Cc2cc([C@@H]3O[C@H](CO)[C@@H](O)[C@H](O)[C@H]3O)c3c(c2C)OCO3)cc1] | (2S,3R,4R,5S,6R)-2-(6-(4-ethylbenzyl)-7-methylbenzo[d][1,3]dioxol-4-yl)-6-(hydroxymethyl)tetrahydro-2H-pyran-3,4,5-triol | 1.1 | 38.3 |
| E065 | 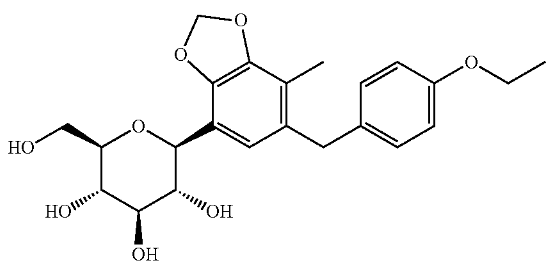 | (2S,3R,4R,5S,6R)-2-(6-(4-ethoxybenzyl)-7-methylbenzo[d][1,3]dioxol-4-yl)-6-(hydroxymethyl)tetrahydro-2H-pyran-3,4,5-triol | 1.6 | 155 |

*Reference compound dapagliflozin IC$_{50}$ = 1.35 ± 0.15 nM (in-house assay)????.
**These data were obtained by single determinations.

As shown above, the compounds of formula I exhibited inhibitory activities against sodium-dependent glucose cotransporter 1 (SGLT1) and sodium-dependent glucose cotransporter 2 (SGLT2) and are thus effective as SGLT1 and SGLT2 dual inhibitors.

What is claimed is:

1. A method for dual inhibition of sodium-dependent glucose cotransporter 1 and sodium-dependent glucose cotransporter 2 in a mammal, which comprises administering the compound of formula I or a pharmaceutically acceptable salt or a prodrug thereof to the mammal:

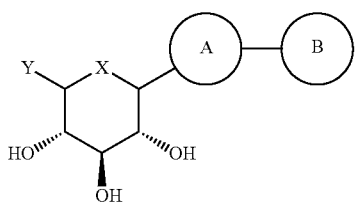

I wherein,

X is oxygen or sulfur;

Y is C$_{1-7}$ alkyl, C$_{2-7}$ alkenyl, C$_{2-7}$ alkynyl, C$_{1-7}$ alkoxy, C$_{1-7}$ alkoxy-C$_{1-7}$ alkyl, C$_{1-7}$ alkylsulfinyl, C$_{1-7}$ alkylsulfonyl, or C$_{1-7}$ alkylthio;

ring A is

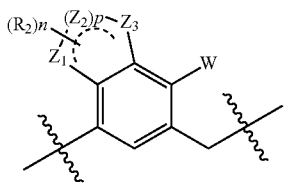

said R$_1$ and W being each independently halogen, hydroxy, C$_{1-7}$ alkyl, or C$_{1-7}$ alkoxy, said n being an integer of 0 to 3, said Z$_1$, Z$_2$, and Z$_3$ being each independently —CH$_2$—, —CH=, —(CO)—, —O—, —S—, —NH—, or —N=, and said p being an integer of 1 to 3;

ring B is

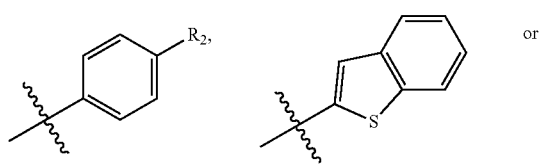

-continued

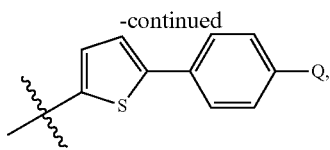

wherein,
said Q is halogen, and
said $R_2$ being selected from the group consisting of hydrogen, halogen, hydroxy, mercapto, cyano, nitro, amino, carboxy, oxo, $C_{1-7}$ alkyl, $C_{1-7}$ alkylthio, $C_{2-7}$ alkenyl, $C_{2-7}$ alkynyl, $C_{1-7}$alkoxy, $C_{1-7}$ alkoxy-$C_{1-7}$ alkyl, $C_{2-7}$ alkenyl-$C_{1-7}$alkyloxy, $C_{2-7}$ alkynyl-$C_{1-7}$ alkyloxy, $C_{3-10}$ cycloalkyl, $C_{3-7}$ cycloalkylthio, $C_{5-10}$ cycloalkenyl, $C_{3-10}$ cycloalkyloxy, $C_{3-10}$ cycloalkyloxy-$C_{1-7}$ alkoxy, phenyl-$C_{1-7}$ alkyl, $C_{1-7}$ alkylthio-phenyl, phenyl-$C_{1-7}$ alkoxy, mono- or di-$C_{1-7}$ alkylamino, mono- or di-$C_{1-7}$ alkylamino-$C_{1-7}$ alkyl, $C_{1-7}$ alkanoyl, $C_{1-7}$ alkanoylamino, $C_{1-7}$ alkylcarbonyl, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfinyl, $C_{6-14}$ arylsulfanyl, $C_{6-14}$ arylsulfonyl, $C_{6-14}$ aryl, 5 to 13-membered heteroaryl, 5 to 10-membered heterocycloalkyl, 5 to 10-membered heterocycloalkyl-$C_{1-7}$ alkyl, or 5 to 10-membered heterocycloalkyl-$C_{1-7}$ alkoxy
said alkyl, alkenyl, alkynyl, or alkoxy is optionally substituted with at least one substituent selected from the group consisting of halogen, hydroxy, cyano, nitro, amino, mercapto, $C_{1-7}$ alkyl, and $C_{2-7}$ alkynyl; and
said cycloalkyl, cycloalkenyl, aryl, heteroaryl, or heterocycloalkyl is optionally substituted with at least one substituent selected from the group consisting of halogen, hydroxy, cyano, nitro, amino, mercapto, $C_{1-4}$ alkyl, and $C_{1-4}$ alkoxy.

2. The method of claim 1, wherein said ring A is selected from the group consisting of:

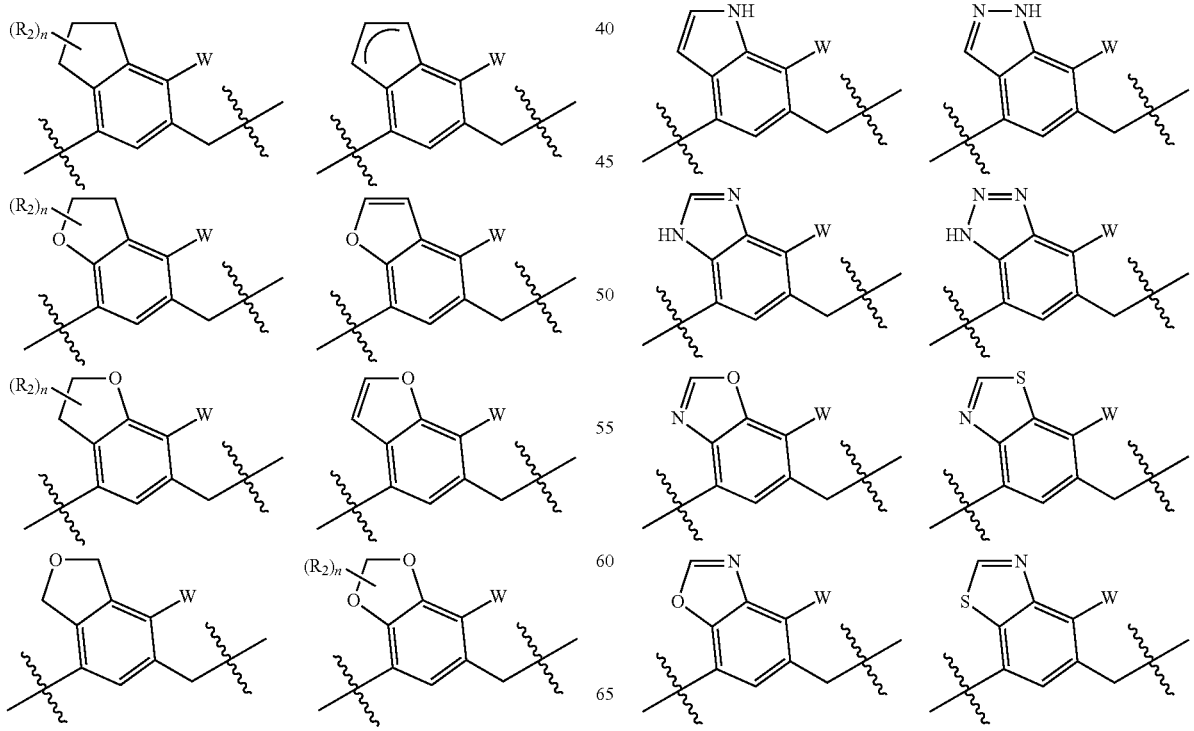
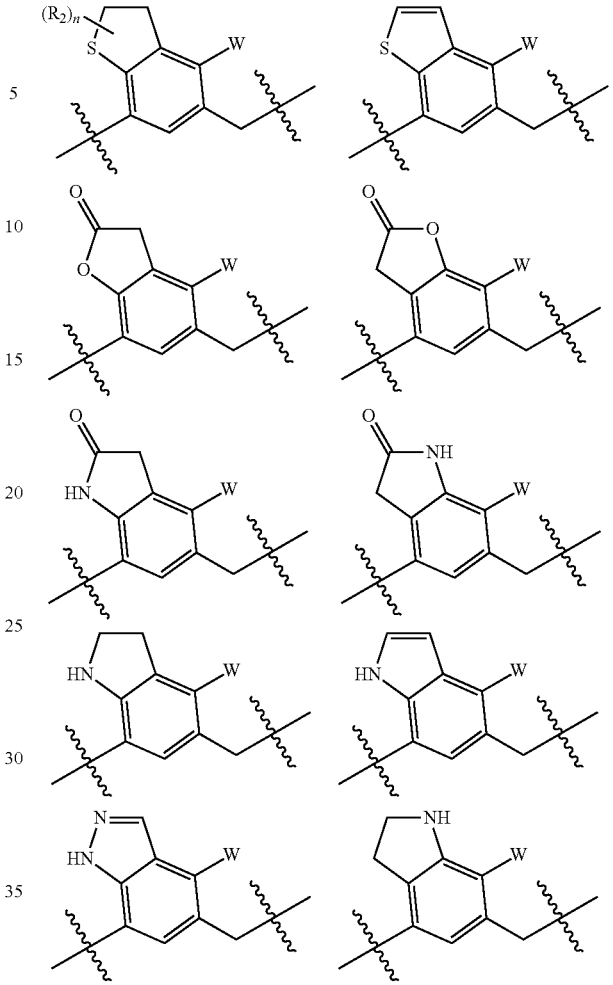

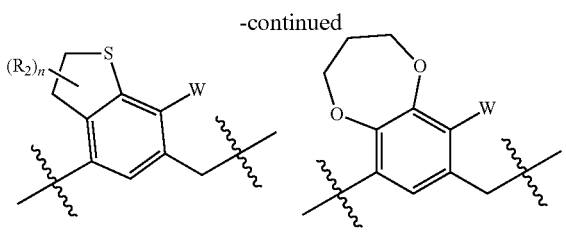

3. The method of claim 1, wherein said ring B is selected from the group consisting of:

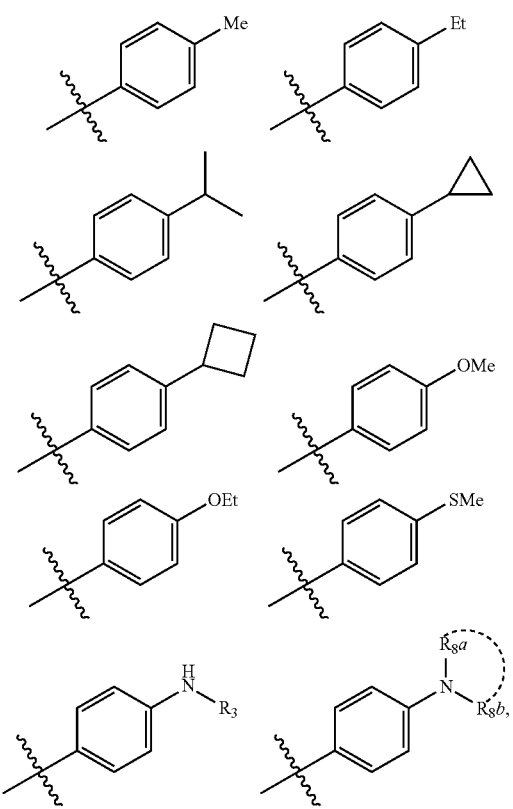

in which $R_3$ is hydrogen, or $C_{1-7}$ alkyl, and $R_{4a}$ and $R_{4b}$ are each independently $C_{1-7}$ alkyl, or $R_{4a}$ and $R_{4b}$ are connected to form a 5 to 10-membered heterocycloalkyl.

4. The method of claim 1, wherein said ring A is an indane, indene, dihydrobenzofuran, dihydroisobenzofuran, benzofuran, dihydrobenzothiophene, benzothiophene, tetrahydronaphthalene, dihydronaphthalene, chroman, chromene, isochroman, isochromene, benzodioxole, benzodioxane, benzooxazine, tetrahydroquinoline, tetrahydroquinoxaline, tetrahydroisoquinoline, indazole, indole, indoline, benzoimidazole, benzooxazole, benzothiazole, benzotriazole, quinazoline, quinoxaline, cinnoline, phthalazine, or benzotriazine ring, which is optionally substituted with a substituent as defined in claim 1.

5. The method of claim 1, wherein the compound of formula I is selected from the group consisting of:

(1) (2S,3R,4R,5S,6R)-2-(7-bromo-6-(4-methoxybenzyl)-2,3-dihydro-1H-inden-4-yl)-6-(hydroxymethyl)tetrahydro-2H-pyran-3,4,5-triol;

(2) (2S,3R,4R,5S,6R)-2-(7-bromo-6-(4-ethoxybenzyl)-2,3-dihydro-1H-inden-4-yl)-6-(hydroxymethyl)tetrahydro-2H-pyran-3,4,5-triol;

(3) (2S,3R,4R,5S,6R)-2-(7-bromo-6-(4-ethylbenzyl)-2,3-dihydro-1H-inden-4-yl)-6-(hydroxymethyl)tetrahydro-2H-pyran-3,4,5-triol;

(4) (2S,3R,4R,5S,6R)-2-(7-chloro-6-(4-methoxybenzyl)-2,3-dihydro-1H-inden-4-yl)-6-(hydroxymethyl)tetrahydro-2H-pyran-3,4,5-triol;

(5) (2R,3S,4R,5R,6S)-2-(hydroxymethyl) -6-(6-(4-methoxybenzyl)-7-methyl-2,3-dihydro-1H-inden-4-yl)tetrahydro-2H-pyran-3,4,5-triol;

(6) (2S,3R,4R,5S,6R)-2-(7-chloro-6-(4-ethoxybenzyl)-2,3-dihydro-1H-inden-4-yl)-6-(hydroxymethyl)tetrahydro-2H-pyran-3,4,5-triol;

(7) (2S,3R,4R,5S,6R)-2-(6-(4-ethoxybenzyl)-7-methyl-2,3-dihydro-1H-inden-4-yl)-6-(hydroxymethyl)tetrahydro-2H-pyran-3,4,5-triol;

(8) (2S,3R,4R,5S,6R)-2-(4-chloro-5-(4-ethylbenzyl)-2,3-dihydrobenzofuran-7-yl)-6-(hydroxymethyl)tetrahydro-2H-pyran-3,4,5-triol;

(9) (2S,3R,4R,5S,6R)-2-(5-chloro-6-(4-ethoxybenzyl)chroman-8-yl)-6-(hydroxymethyl)tetrahydro-2H-pyran-3,4,5-triol;

(10) (2S,3R,4R,5S,6R)-2-(5-chloro-6-(4-methoxybenzyl)chroman-8-yl)-6-(hydroxymethyl)tetrahydro-2H-pyran-3,4,5-triol;

(11) (2S,3R,4R,5S,6R)-2-(5-chloro-6-(4-ethylbenzyl)chroman-8-yl)-6-(hydroxymethyl)tetrahydro-2H-pyran-3,4,5-triol;

(12) (2S,3R,4R,5S,6R)-2-(4-chloro-5-(4-methoxybenzyl)-2,3-dihydrobenzofuran-7-yl)-6-(hydroxymethyl)tetrahydro-2H-pyran-3,4,5-triol;

(13) (2S,3R,4R,5S,6R)-2-(4-chloro-5-(4-ethoxybenzyl)-2,3-dihydrobenzofuran-7-yl)-6-(hydroxymethyl)tetrahydro-2H-pyran-3,4,5-triol;

(14) (2S,3R,4R,5S,6R)-2-(8-chloro-7-(4-ethylbenzyl)chroman-5-yl)-6-(hydroxymethyl)tetrahydro-2H-pyran-3,4,5-triol;

(15) (2S,3R,4R,5S,6R)-2-(8-chloro-7-(4-methoxybenzyl)-2,3-dihydrobenzo[b][1,4]dioxin-5-yl)-6-(hydroxymethyl)tetrahydro-2H-pyran-3,4,5-triol;

(16) (2S,3R,4R,5S,6R)-2-(8-chloro-7-(4-ethylbenzyl)-2,3-dihydrobenzo[b][1,4]dioxin-5-yl)-6-(hydroxymethyl)tetrahydro-2H-pyran-3,4,5-triol;

(17) (2S,3R,4R,5S,6R)-2-(4-chloro-5-(4-cyclopropylbenzyl)-2,3-dihydrobenzofuran-7-yl)-6-(hydroxymethyl)tetrahydro-2H-pyran-3,4,5-triol;

(18) (2S,3R,4R,5S,6R)-2-(5-chloro-6-(4-cyclopropylbenzyl)chroman-8-yl)-6-(hydroxymethyl)tetrahydro-2H-pyran-3,4,5-triol;

(19) (2S,3R,4R,5S,6R)-2-(4-chloro-5-(4-ethylbenzyl)-2-methyl-2,3-dihydrobenzo[b]thiophen-7-yl)-6-(hydroxymethyl)tetrahydro-2H-pyran-3,4,5-triol;

(20) (2S,3R,4R,5S,6R)-2-(4-chloro-5-(4-ethoxybenzyl)-2-methyl-2,3-dihydrobenzofuran-7-yl)-6-(methylthio)tetrahydro-2H-pyran-3,4,5-triol;

(21) (2S,3R,4R,5S,6R)-2-(8-chloro-7-(4-ethoxybenzyl)-2,3-dihydrobenzo[b][1,4]dioxin-5-yl)-6-(methylthio)tetrahydro-2H-pyran-3,4,5-triol;

(22) (2S,3R,4R,5S,6R)-2-(8-chloro-7-(4-cyclopropylbenzyl)chroman-5-yl)-6-(hydroxymethyl)tetrahydro-2H-pyran-3,4,5-triol;

(23) (2S,3R,4R,5S,6R)-2-(8-chloro-7-(4-methoxybenzyl)chroman-5-yl)-6-(hydroxymethyl)tetrahydro-2H-pyran-3,4,5-triol;

(24) (2S,3R,4R,5S,6R)-2-(7-chloro-6-(4-cyclopropylbenzyl) benzo[d][1,3]dioxol-4-yl)-6-(hydroxymethyl)tetrahydro-2H-pyran-3,4,5-triol;

(25) (2S,3R,4R,5S,6R)-2-(7-chloro-6-(4-methoxybenzyl)benzo[d][1,3]dioxol-4-yl)-6-(hydroxymethyl)tetrahydro-2H-pyran-3,4,5-triol;

(26) (2S,3R,4R,5S,6R)-2-(7-chloro-6-(4-ethylbenzyl)benzo[d][1,3]dioxol-4-yl)-6-(hydroxymethyl)tetrahydro-2H-pyran-3,4,5-triol;

(27) (2S,3R,4R,5S,6R)-2-(8-chloro-7-(4-cyclopropylbenzyl)-2,3-dihydrobenzo[b][1,4]dioxin-5-yl)-6-(hydroxymethyl)tetrahydro-2H-pyran-3,4,5-triol;

(28) (2S,3R,4R,5S,6R)-2-(7-chloro-6-(4-vinylbenzyl)-2,3-dihydrobenzofuran-4-yl)-6-(hydroxymethyl)tetrahydro-2H-pyran-3,4,5-triol;

(29) (2S,3R,4R,5S,6R)-2-(5-chloro-6-(4-methoxybenzyl)chroman-8-yl)-6-(methylthio)tetrahydro-2H-pyran-3,4,5-triol;

(30) (2S,3R,4R,5S,6R)-2-(4-chloro-5-(4-methoxybenzyl)-2,3-dihydrobenzo[b]thiophen-7-yl)-6-(hydroxymethyl)tetrahydro-2H-pyran-3,4,5-triol;

(31) (2S,3R,4R,5S,6R)-2-(4-chloro-5-(4-ethoxybenzyl)-3-methyl-2,3-dihydrobenzofuran-7-yl)-6-(hydroxymethyl)tetrahydro-2H-pyran-3,4,5-triol;

(32) (2S,3R,4R,5S,6R)-2-(7-(difluoromethyl)-6-(4-methoxybenzyl)-2,3-dihydro-1H-inden-4-yl)-6-(hydroxymethyl)tetrahydro-2H-pyran-3,4,5-triol;

(33) (2S,3R,4R,5S,6R)-2-(7-bromo-6-(4-ethylbenzyl)-2,3-dihydro-1H-inden-4-yl)-6-(hydroxymethyl)tetrahydro-2H-pyran-3,4,5-triol;

(34) (2S,3R,4R,5S,6R)-2-(7-chloro-6-(4-methoxybenzyl)-2,3-dihydrobenzo[b]thiophen-4-yl)-6-(hydroxymethyl)tetrahydro-2H-pyran-3,4,5-triol;

(35) (2S,3R,4R,5S,6R)-2-(7-chloro-6-(4-ethylbenzyl)-2,3-dihydrobenzo[b]thiophen-4-yl)-6-(hydroxymethyl)tetrahydro-2H-pyran-3,4,5-triol;

(36) (2S,3R,4R,5S,6R)-2-(8-chloro-7-(4-methoxybenzyl)thiochroman-5-yl)-6-(hydroxymethyl)tetrahydro-2H-pyran-3,4,5-triol;

(37) (2R,3S,4R,5R,6S)-2-(hydroxymethyl)-6-(3-(4-methoxybenzyl)-4-methyl-5,6,7,8-tetrahydronaphthalen-1-yl)tetrahydro-2H-pyran-3,4,5-triol;

(38) (2S,3R,4R,5S,6R)-2-(4-chloro-3-(4-methoxybenzyl)-5,6,7,8-tetrahydronaphthalen-1-yl)-6-(hydroxymethyl)tetrahydro-2H-pyran-3,4,5-triol;

(39) (2S,3R,4R,5S,6R)-2-(4-chloro-3-(4-ethoxybenzyl)-5,6,7,8-tetrahydronaphthalen-1-yl)-6-(hydroxymethyl)tetrahydro-2H-pyran-3,4,5-triol;

(40) (2S,3R,4R,5S,6R)-2-(7-chloro-6-(4-methylbenzyl)benzo[d][1,3]dioxol-4-yl)-6-(hydroxymethyl)tetrahydro-2H-pyran-3,4,5-triol;

(41) (2R,3S,4R,5R,6S)-2-(hydroxymethyl)6-(6-(4-methylbenzyl)-2,3-dihydro-1H-inden-4-yl)tetrahydro-2H-pyran-3,4,5-triol;

(42) (2S,3R,4R,5S,6R)-2-(8-chloro-7-(4-methylbenzyl)-2,3-dihydrobenzo[b][1,4]dioxin-5-yl)-6-(hydroxymethyl)tetrahydro-2H-pyran-3,4,5-triol;

(43) (2S,3R,4R,5S,6R)-2-(4-chloro-3-(4-ethylbenzyl)-5,6,7,8-tetrahydronaphthalen-1-yl)-6-(hydroxymethyl)tetrahydro-2H-pyran-3,4,5-triol;

(44) (2S,3R,4R,5S,6R)-2-(3-(4-ethylbenzyl)-4-methyl-5,6,7,8-tetrahydronaphthalen-1-yl)-6-(hydroxymethyl)tetrahydro-2H-pyran-3,4,5-triol;

(45) (2S,3R,4R,5S,6R)-2-(8-chloro-7-(4-methylbenzyl)chroman-5-yl)-6-(hydroxymethyl)tetrahydro-2H-pyran-3,4,5-triol;

(46) (2S,3R,4R,5S,6R)-2-(4-chloro-5-(4-methylbenzyl)-2,3-dihydrobenzofuran-7-yl)-6-(hydroxymethyl)tetrahydro-2H-pyran-3,4,5-triol;

(47) (2S,3R,4R,5S,6R)-2-(3-(4-ethoxybenzyl)-4-methyl-5,6,7,8-tetrahydronaphthalen-1-yl)-6-(hydroxymethyl)tetrahydro-2H-pyran-3,4,5-triol;

(48) (2S,3R,4R,5S,6R)-2-(7-chloro-6-(4-methoxybenzyl)-2,3-dihydro-1H-inden-4-yl)6-(methylthio)tetrahydro-2H-pyran-3,4,5-triol;

(49) (2S,3R,4R,5S,6R)-2-(7-chloro-6-(4-(methylthio)benzyl)benzo[d][1,3]dioxol-4-yl)-6-(hydroxymethyl)tetrahydro-2H-pyran-3,4,5-triol;

(50) (2S,3R,4R,5S,6R)-2-(8-chloro-7-(4-(methylthio)benzyl)-2,3-dihydrobenzo[b][1,4]dioxin-5-yl)-6-(hydroxymethyl)tetrahydro-2H-pyran-3,4,5-triol;

(51) (2S,3R,4R,5S,6R)-2-(7-chloro-6-(4-ethoxybenzyl)benzo[d][1,3]dioxol-4-yl)-6-(methylthio)tetrahydro-2H-pyran-3,4,5-triol;

(52) (2S,3R,4R,5S,6R)-2-(5-chloro-6-(4-methylbenzyl)chroman-8-yl)-6-(hydroxymethyl)tetrahydro-2H-pyran-3,4,5-triol;

(53) (2S,3R,4R,5S,6R)-2-(6-(benzo[b]thiophen-2-ylmethyl)-7-chlorobenzo[d][1,3]dioxol-4-yl)-6-(hydroxymethyl)tetrahydro-2H-pyran-3,4,5-triol;

(54) (2S,3R,4R,5S,6R)-2-(8-chloro-7-((5-(4-fluorophenyl)thiophen-2-yl)methyl)-2,3-dihydrobenzo[b][1,4]dioxin-5-yl)-6-(hydroxymethyl)tetrahydro-2H-pyran-3,4,5-triol;

(55) (2S,3R,4R,5S,6R)-2-(6-(benzo[b]thiophen-2-ylmethyl)-7-chloro-2,3-dihydrobenzofuran-4-yl)-6-(hydroxymethyl)tetrahydro-2H-pyran-3,4,5-triol;

(56) (2S,3R,4R,5S,6R)-2-(7-(benzo[b]thiophen-2-ylmethyl)-8-chloro-2,3-dihydrobenzo[b][1,4]dioxin-5-yl)-6-(hydroxymethyl)tetrahydro-2H-pyran-3,4,5-triol;

(57) (2S,3R,4R,5S,6R)-2-(4-bromo-3-(4-ethylbenzyl)-5,6,7,8-tetrahydronaphthalen-1-yl)-6-(hydroxymethyl)tetrahydro-2H-pyran-3,4,5-triol;

(58) (2S,3R,4R,5S,6R)-2-(4-bromo-3-(4-ethoxybenzyl)-5,6,7,8-tetrahydronaphthalen-1-yl)-6-(hydroxymethyl)tetrahydro-2H-pyran-3,4,5-triol;

(59) (2S,3R,4R,5S,6R)-2-(7-chloro-6-(4-ethoxybenzyl)-2,3-dihydrobenzo[b]thiophen-4-yl)-6-(hydroxymethyl)tetrahydro-2H-pyran-3,4,5-triol;

(60) (2S,3R,4R,5S,6R)-2-(7-chloro-6-(4-cyclopropylbenzyl)-2,3-dihydrobenzo[b]thiophen-4-yl)-6-(hydroxymethyl)tetrahydro-2H-pyran-3,4,5-triol;

(61) (2R,3S,4R,5R,6S)-2-((hydroxymethyl)-6-(7-methyl-6-(4-methylbenzyl)benzo[d][1,3]dioxol-4-yl)tetrahydro-2H-pyran-3,4,5-triol;

(62) (2S,3R,4R,5S,6R)-2-(5-chloro-6-(4-cyclobutylbenzyl)chroman-8-yl)-6-(hydroxymethyl)tetrahydro-2H-pyran-3,4,5-triol;

(63) (2R,3S,4R,5R,6S)-2-((hydroxymethyl)-6-(6-(4-methoxybenzyl)-7-methylbenzo[d][1,3]dioxol-4-yl)tetrahydro-2H-pyran-3,4,5-triol;

(64) (2S,3R,4R,5S,6R)-2-(6-(4-ethylbenzyl)-7-methylbenzo[d][1,3]dioxol-4-yl)-6-(hydroxymethyl)tetrahydro-2H-pyran-3,4,5-triol; and

(65) (2S,3R,4R,5S,6R)-2-(6-(4-ethoxybenzyl)-7-methylbenzo[d][1,3]dioxol-4-yl)-6-(hydroxymethyl)tetrahydro-2H-pyran-3,4,5-triol.

\* \* \* \* \*